US012653792B2

(12) United States Patent
Xu et al.

(10) Patent No.: US 12,653,792 B2
(45) Date of Patent: Jun. 16, 2026

(54) SYNTHETIC LIPIDS FOR MRNA DELIVERY

(71) Applicant: Trustees of Tufts College, Medford, MA (US)

(72) Inventors: Qiaobing Xu, Lexington, MA (US); Ming Wang, Beijing (CN)

(73) Assignee: Trustees of Tufts College, Medford, MA (US)

( * ) Notice: Subject to any disclaimer, the term of this patent is extended or adjusted under 35 U.S.C. 154(b) by 1033 days.

(21) Appl. No.: 17/543,173

(22) Filed: Dec. 6, 2021

(65) Prior Publication Data

US 2022/0168231 A1 Jun. 2, 2022

Related U.S. Application Data

(63) Continuation of application No. PCT/US2020/036085, filed on Jun. 4, 2020.

(60) Provisional application No. 62/857,111, filed on Jun. 4, 2019.

(51) Int. Cl.

| | |
|---|---|
| ***A61K 9/51*** | (2006.01) |
| ***A61K 31/7088*** | (2006.01) |
| ***A61K 38/46*** | (2006.01) |
| ***A61K 48/00*** | (2006.01) |
| ***A61P 3/06*** | (2006.01) |
| ***A61P 9/00*** | (2006.01) |
| ***C07C 323/12*** | (2006.01) |
| ***C12N 9/22*** | (2006.01) |
| ***C12N 15/11*** | (2006.01) |

(52) U.S. Cl.

CPC ........ *A61K 9/5123* (2013.01); *A61K 31/7088* (2013.01); *A61K 38/465* (2013.01); *A61K 48/0041* (2013.01); *A61P 3/06* (2018.01); *A61P 9/00* (2018.01); *C07C 323/12* (2013.01); *C12N 9/22* (2013.01); *C12N 15/11* (2013.01); *C12N 2310/20* (2017.05); *C12N 2320/32* (2013.01); *C12N 2800/80* (2013.01)

(58) Field of Classification Search

None

See application file for complete search history.

(56) References Cited

U.S. PATENT DOCUMENTS

| | | | |
|---|---|---|---|
| 2011/0052673 A1 | 3/2011 | Tzianabos et al. | |
| 2016/0129120 A1 | 5/2016 | Xu et al. | |

FOREIGN PATENT DOCUMENTS

| | | | |
|---|---|---|---|
| CN | 101835498 A | 9/2010 | |
| EP | 3315125 A1 * | 5/2018 | ......... A61K 31/7088 |
| WO | WO-2007/134161 A2 | 11/2007 | |
| WO | WO-2014/134445 A1 | 9/2014 | |
| WO | WO-2018/191750 A2 | 10/2018 | |
| WO | WO-2020/247604 A1 | 12/2020 | |

OTHER PUBLICATIONS

Dron, J.S et al., Genetics of lipid and lipoprotein disorders and traits, Cardiovascular Genetics, 2016, vol. 4, 130-141 (Year: 2016).*

Anonymous, Cardiovascular diseases, World Health Organization, 2021, https://www.who.int/news-room/fact-sheets/detail/cardiovascular-diseases-(cvds), Accessed Feb. 18, 2025 (Year: 2021).*

Chadwick, A.C. et al., Reduced blood lipid levels with in vivo CRISPR-Cas9 base editing of ANGPTL3, Circulation, Feb. 27, 2018, vol. 137, 975-977 (Year: 2018).*

Wang, M. et al., Efficient delivery of genome-editing proteins using bioreducible lipid nanoparticles, PNAS, Feb. 5, 2016, vol. 113, 2868-2873 (Year: 2016).*

Sago, C.D. et al., High-throughput in vivo screen of functional mRNA delivery identifies nanoparticles for endothelial cell gene editing, PNAS, Oct. 1, 2018, vol. 115, E9944-E9952 (Year: 2018).*

Sago et al., "High-throughput in vivo screen of functional mRNA delivery identifies nanoparticles for endothelial cell gene editing," PNAS 115(42): pp. 9944-9952 (2018).

Wang et al., "Combinatorially Designed Lipid-like Nanoparticles for Intracellular Delivery of Cytotoxic Protein for Cancer Therapy," Angew. Chem. Int. Ed. 53: pp. 2893-2898 (2014).

Okazaki, "Potential new treatment for dyslipidemia," Journal of the Japanese Society of Internal Medicine, 106.4 (2017): 735-741.

Chadwick et al., "Reduced blood lipid levels with in vivo CRISPR-Cas9 base editing of ANGPTL3." Circulation 137.9, pp. 975-977 (2018).

Gaudet et al., "ANGPTL3 inhibition in homozygous familial hypercholesterolemia." New England Journal of Medicine 377.3, pp. 296-297. (2017).

Liu et al., "Fast and efficient CRISPR/Cas9 genome editing in vivo enabled by bioreducible lipid and messenger RNA nanoparticles." Advanced Materials 31.33 (2019).

Invitation to Pay Additional Fees for International Application No. PCT/US2020/036085 dated Sep. 18, 2020.

International Search Report and Written Opinion for International Application No. PCT/US2020/036085 mailed Nov. 4, 2020.

Extended European Search Report for EP Application No. 20817914.3 dated May 19, 2023.

Lupo et al., "Angiopoietin-Like 3 (ANGPTL3) and Atherosclerosis: Lipid and Non-Lipid Related Effects" J. Cardiovasc. Dev. Dis. 5(3): 13 pages (2018).

* cited by examiner

*Primary Examiner* — Bethany P Barham
*Assistant Examiner* — Paul Hoerner
(74) *Attorney, Agent, or Firm* — Foley Hoag LLP; Dana M. Gordon; Alexander J. J. Chatterley D.

(57) ABSTRACT

Provided are methods of treating a human lipoprotein metabolism disorder or a cardiovascular disease, comprising administering to a subject in need thereof a lipidoid nanoparticle, comprising a lipid, a CRISPR/Cas9 mRNA, and a single guide RNA (sgRNA).

20 Claims, 32 Drawing Sheets

Specification includes a Sequence Listing.

BAMEA-O16B

BAMEA-O16 lane 1: RFP mRNA
lane 2: RFP mRNA + BAMEA-O16B
lane 3: RFP mRNA + BAMEA-O16B + GSH
lane 4: RFP mRNA + BAMEA-O16
lane 5: RFP mRNA + BAMEA-O16 + GSH
lane 6: RFP mRNA + GSH Amine head Acrylate tail Lipidoid Head

113

304

400

200

306

401

Tail:

O16B

O14B

O12B

O10B

DSPC

DOPE

DOPC

Merged eFluor660 tdTomato DAPI

Fig. 19B

| Edited ANGPTL3 sequence | Mutation type | frequency in best 306-O12B mouse (%) | frequency in best MC-3 mouse (%) | frequency in control mouse (%) |
|---|---|---|---|---|
| CGTTTTTAACTTGTAGTGTA | wild-type | | | |
| CGTTTT_AACTTGTAGTGTA | 1nt deletion | 31.0 | 20.0 | 0.19 |
| CGTTTTT\|AACTTGTAGTGTA<br>T | 1nt insertion | 12.0 | 8.0 | 0 |
| CGTTT__AACTTGTAGTGTA | 2nt deletion | 2.0 | 1.0 | 0 |
| other edits | | 3.4 | 0.9 | 0.11 |
| total edited alleles | | 48.4 | 29.9 | 0.3 |

Fig. 19C

| Potential off-target site | Location | frequency in best 306-O12B mouse (%) | frequency in best MC-3 mouse (%) | frequency in control mouse (%) |
|---|---|---|---|---|
| aACACTACAA-TTAAAAACGTGG | chr17: 67139471 | 0.06 | 0.04 | 0.06 |
| TACACTAaAA-TTAAAAACGTGG | chr10: 96372376 | 0.03 | 0.05 | 0.05 |
| TtCACTACAAGTTAGAAAACaGGG | chr3: 96010269 | 0.03 | 0.03 | 0.03 |
| TACACTACGAAaTTAAAAcCGAGG | chr14: 113652925 | 0.04 | 0.04 | 0.02 |
| TACACTACAAGTTCAAAtACaTGG | chr9: 20240345 | 0.02 | 0.04 | 0.02 |
| TACACTA-AAGaTAAAAACaTGG | chr8: 57778609 | 0.04 | 0.04 | 0.04 |
| TACAgT-CAAGTTAAAAACcAGG | chr12: 53110237 | 0.09 | 0.09 | 0.09 |
| T-CACTACtAGaTAAAAACGTGG | chr3: 65249939 | 0.04 | 0.04 | 0.03 |
| cACACTACAAG-TAAAAACaGGG | chr3: 38440103 | 0.04 | 0.05 | 0.04 |

SYNTHETIC LIPIDS FOR MRNA DELIVERY

RELATED APPLICATIONS

This application is a continuation of PCT Application PCT/US20/36085, filed Jun. 4, 2020; which claims the benefit of priority to U.S. Provisional Application Ser. No. 62/857,111, filed Jun. 4, 2019; the contents of which are incorporated herein by reference in their entirety.

GOVERNMENT SUPPORT

This invention was made with government support under grant numbers EB024041 and TR002636 awarded by the National Institutes of Health. The government has certain rights in the invention.

SEQUENCE LISTING

The instant application contains a Sequence Listing which has been submitted electronically in ASCII format and is hereby incorporated by reference in its entirety. Said ASCII copy, created on Jul. 16, 2020, is named TUV-13925_SL.txt and is 8,728 bytes in size.

BACKGROUND

Angiopoietin-like 3 (ANGPTL3) is an enzyme which serves to regulate plasma lipoprotein levels. There are humans with ANGPTL3 deficiency, resulting from naturally-occurring loss-of-function mutations in the ANGPTL3 gene. These patients show lowered blood triglycerides (TG) and low density lipoprotein cholesterol (LDL-C), without any apparent clinical risks or complications resulting from this loss. Recent genetic and pharmacologic studies have validated this finding and indicated that ANGPTL3 knockdown may confer some protective benefits, making ANGPTL3 an attractive therapeutic target for the treatment of human lipoprotein metabolism disorders. Two different therapeutic inhibition strategies against ANGPTL3 have recently been validated. In one clinical trial, an ANGPTL3 targeting monoclonal antibody, evinacumab, has proven effective reduction in LDL-C and TG levels in healthy human volunteers. These results are in line with a study that found administration of an antisense oligonucleotides (ASO) targeting ANGPTL3 messenger RNA (mRNA) achieved reduced lipids levels, as well as decreased progression of atherosclerosis in mice. Furthermore, lowered levels of atherogenic lipoproteins in humans was also observed and no serious adverse events were documented in their phase I randomized clinical trial. These observations strongly demonstrated that therapeutic antagonism of ANGPTL3 is effective and safe in reducing levels of lipids and incidence of atherosclerotic cardiovascular disease.

The CRISPR/Cas9 (clustered regularly interspaced short palindromic repeats [CRISPR]/CRISPR-associated protein 9) system is one of the most revolutionary genome editing tools. CRISPR/Cas9 introduces DNA double-strand breaks (DSBs) in a targeted (i.e. sequence-specific) fashion, followed by repair of the DSBs either by nonhomologous end-joining (NHEJ) or homology directed repair (HDR). As compared with conventional ASO or antibody therapies which are transient, the CRISPR/Cas9 system can induce permanent loss-of-function target gene mutations which result in long-term therapeutic effects in the edited cells, making CRISPR/Cas9 a promising candidate for the treatment of human diseases. However, the safe, efficient, and specific delivery of the CRISPR/Cas9 machineries has remained a tremendous technical challenge, which has limited the therapeutic application of this technology. The use of viral vectors (such as adenovirus or adeno-associated virus) often afford a very high editing efficiency, but also carry significant safety risks regarding the undesired insertional mutagenesis and potential biosafety concerns which have limited their application. In comparison, non-viral nanoparticles, such as lipid nanoparticles (LNPs), gold nanoparticles, and polymeric nanoparticles, with better safety profile have been developed for the delivery of CRISPR plasmid DNA, messenger RNA (mRNA), and ribonucleoproteins (RNPs), typically at the cost of reduced delivery efficiency. While CRISPR delivery in each of the DNA, mRNA, and RNP formats has potential strengths, mRNA delivery may be particularly promising for in vivo genome editing applications.

SUMMARY

In one aspect, the present disclosure provides methods of treating a human lipoprotein metabolism disorder or a cardiovascular disease, comprising administering to a subject in need thereof a lipidoid nanoparticle, which comprises a lipid, a CRISPR/Cas9 mRNA, and a single guide RNA (sgRNA), wherein the sgRNA is single guide Angiopoietin-like 3 (sgANGPTL3) or single guide proprotein convertase subtilisin/kexin type 9 (sgPCSK9);

the lipid is represented by formula I:

$$R^{Head}—R^{Lipid} \quad (I),$$

or a pharmaceutically acceptable salt thereof, wherein $R^{Head}$ is

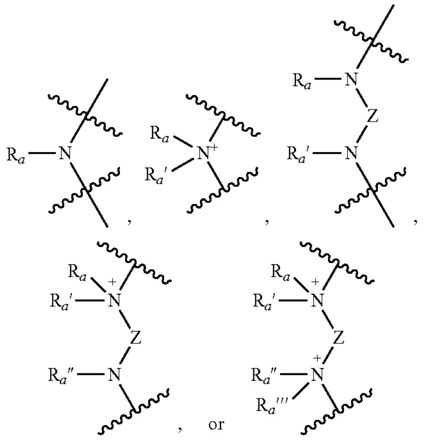

$R^a$, $R^{a'}$, $R^{a''}$, and $R^{a'''}$ each independently is $R^{Lipid}$, H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl, wherein $R^a$ and $R^{a'}$ or $R^{a''}$ and $R^{a'''}$ are not both $R^{Lipid}$;

Z is a $C_1$-$C_{20}$ bivalent aliphatic radical, a $C_1$-$C_{20}$ bivalent heteroaliphatic radical, a bivalent aryl radical, or a bivalent heteroaryl radical; and $R^{Lipid}$ each independently is

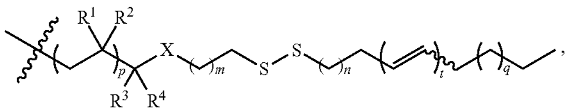

wherein:

$R^1$ and $R^2$ are H, OH, $NHR^{30}$, or SH;

$R^3$ and $R^4$ are both H; or $R^3$ and $R^4$ are taken together to form an oxo (=O) group;

X is $CH_2$, O, $NR^{30}$, or S;

$R^{30}$ is H, $C_{1-6}$ alkyl, $C_{1-6}$ alkenyl, or $C_{1-6}$ alkynyl;

m is an integer selected from 1-3;

n is an integer selected from 1-14;

p is 0 or 1;

q is an integer selected from 1-10; and t is 0, 1, or 2.

In another aspect, the present disclosure provides lipids selected from the group consisting of

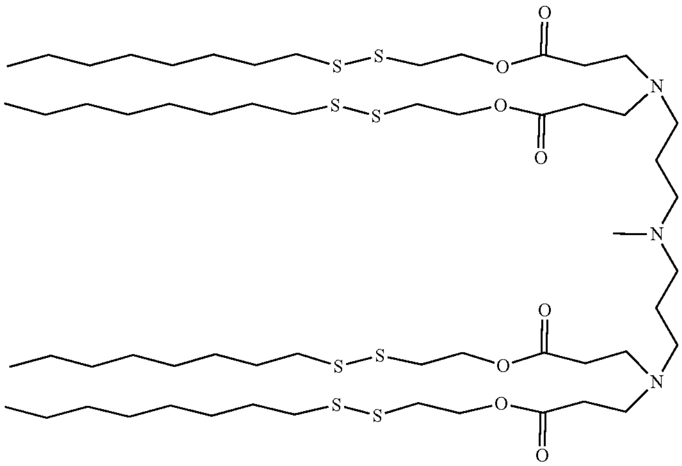

,

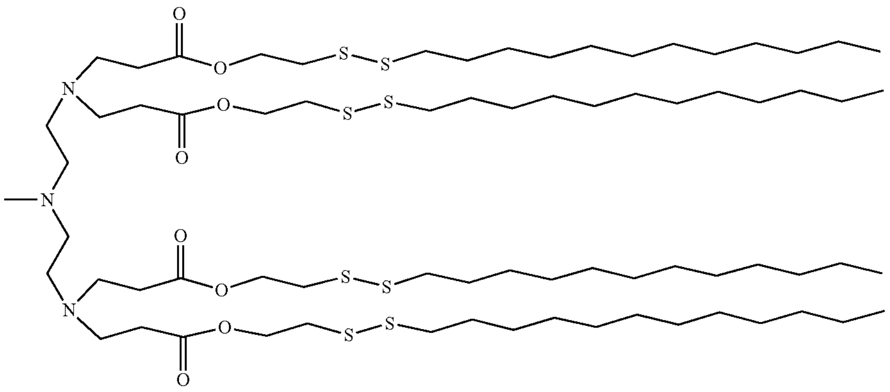

, and

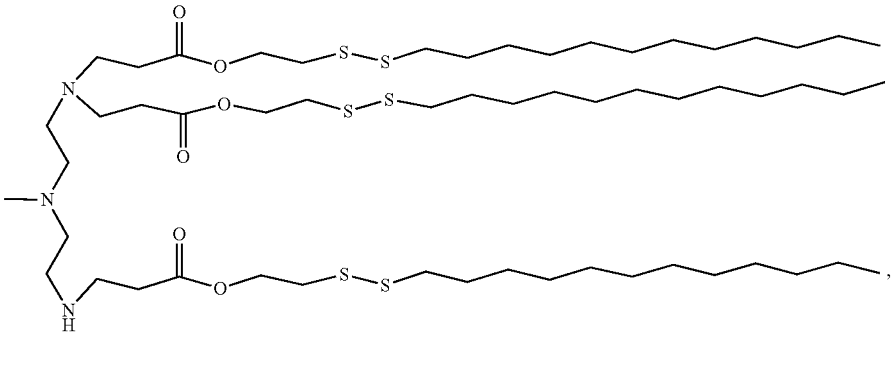

,

BRIEF DESCRIPTION OF THE DRAWINGS

FIG. 19B depicts the editing frequencies of specific edited alleles in most-edited mouse in each treatment group. FIG. 19B discloses SEQ ID NOS 29-32, respectively, in order of appearance.

FIG. 19C depicts the editing frequencies at 9-top predicted off-target sites. FIG. 19C discloses SEQ ID NOS 33-41, respectively, in order of appearance.

DETAILED DESCRIPTION

Figure 1A:
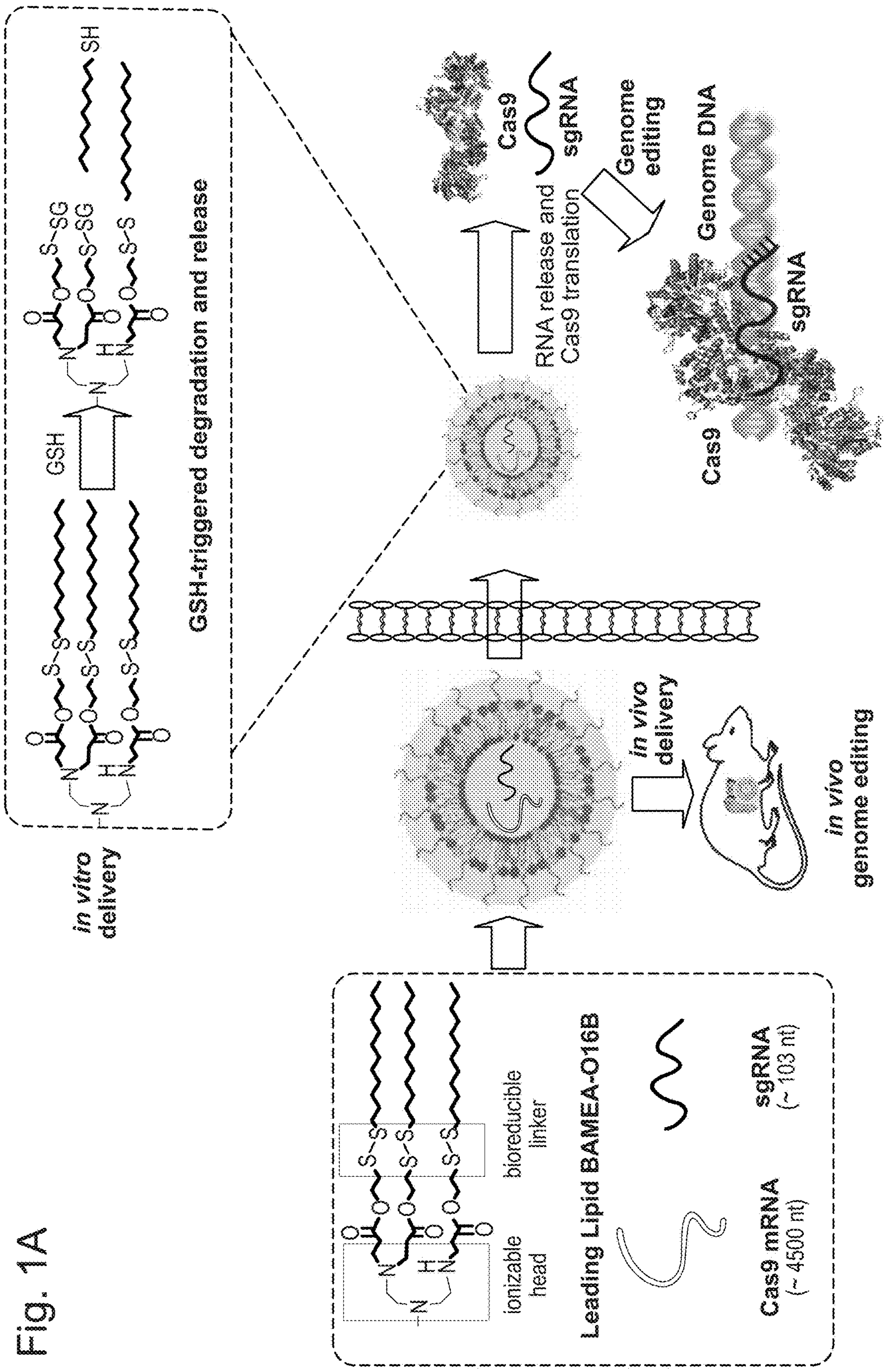
FIG. 1A is a schematic diagram of Cas9 mRNA delivery in vitro and in vivo illustrating formulating bioreducible lipid/Cas9 mRNA/sgRNA nanoparticle for CRISPR/Cas9 genome editing delivery in vitro and in vivo.
Figure 1B:
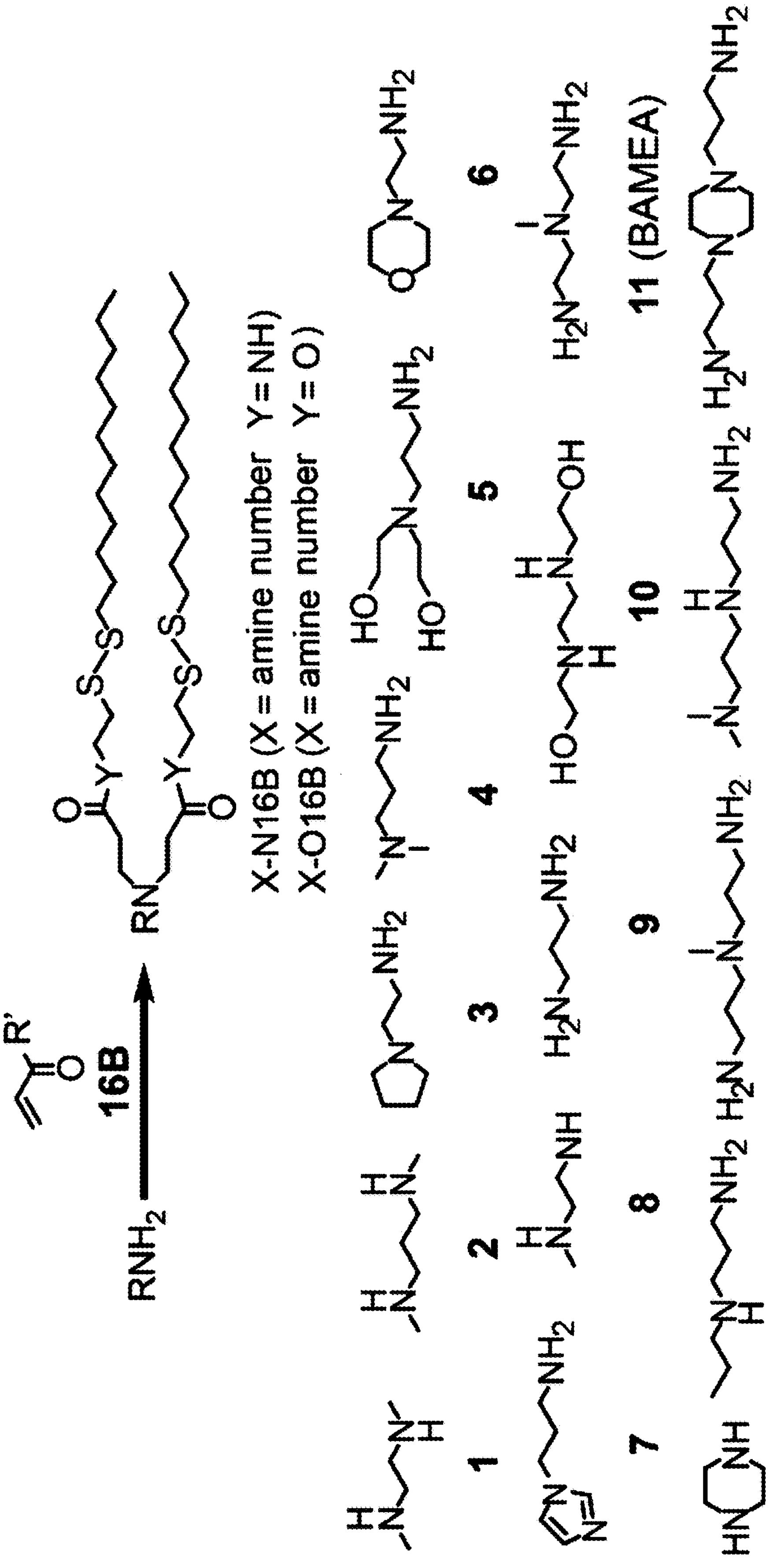
FIG. 1B is a schematic diagram depicting the synthesis route, lipid nomenclature and chemical structure of amines used for lipid synthesis.

Disclosed are new approaches for systematic delivery of CRISPR/Cas9 by encapsulating Cas9 mRNA and sgRNA simultaneously into bioreducible lipid nanoparticle for efficient and very fast genome editing in vitro and in vivo. Also disclosed are bioreducible lipid nanoparticles composed of disulfide bond-containing hydrophobic tails for mRNA delivery and CRISPR/Cas9 genome editing (FIG. 1A and FIG. 1B).

In this disclosure, bioreducible lipids are identified to deliver reporter mRNA and Cas9 mRNA/sgRNA complex both in vitro and in vivo via a screening and optimization approach. The bioreducible lipids can encapsulate mRNA via electrostatic interaction to assemble nanoparticle, while releasing mRNA intracellularly in response to the reductive chemical signals through a disulfide bond exchange mechanism (FIG. 1A).

Simultaneous delivery of Cas9 mRNA/sgRNA knocks out GFP expression of human embryonic kidney (HEK) cells with high efficiency, and an effective gene knockout was observed even rapidly post Cas9 mRNA delivery, which is a significant enhancement compared to Cas9/sgRNA RNPs delivery in terms of in vitro genome editing efficiency. Intravenous injection of bioreducible lipid nanoparticles effectively knocked mouse serum proprotein convertase subtilisin/kexin type 9 (PCSK9) down to very low level compared to non-treated mouse. The bioreducible lipid represents one of the most efficient non-viral CRISPR/Cas9 genome editing delivery reported so far.

In one aspect, the present disclosure provides methods of treating a human lipoprotein metabolism disorder or a cardiovascular disease, comprising administering to a subject in need thereof a lipidoid nanoparticle, which comprises a lipid, a CRISPR/Cas9 mRNA, and a single guide RNA (sgRNA), wherein the sgRNA is single guide Angiopoietin-like 3 (sgANGPTL3) or single guide proprotein convertase subtilisin/kexin type 9 (sgPCSK9);

the lipid is represented by formula I:

$$R^{Head}—R^{Lipid} \quad (I),$$

or a pharmaceutically acceptable salt thereof, wherein $R^{Head}$ is

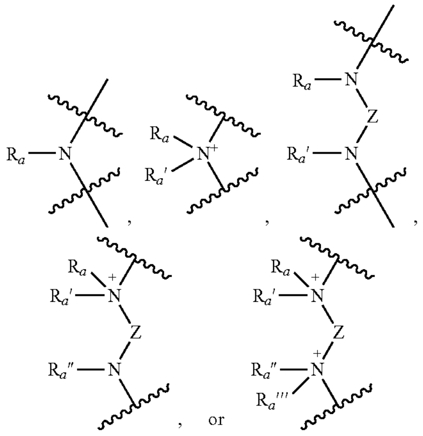

, or $R^a$, $R^{a'}$, $R^{a''}$, and $R^{a'''}$ each independently is $R^{Lipid}$, H, $C_1$-$C_{20}$ alkyl, $C_2$-$C_{20}$ alkenyl, $C_2$-$C_{20}$ alkynyl, $C_3$-$C_{20}$ cycloalkyl, $C_1$-$C_{20}$ heteroalkyl, $C_1$-$C_{20}$ heterocycloalkyl, aryl, or heteroaryl, wherein $R^a$ and $R^{a'}$ or $R^{a''}$ and $R^{a'''}$ are not both $R^{Lipid}$;

Z is a $C_1$-$C_{20}$ bivalent aliphatic radical, a $C_1$-$C_{20}$ bivalent heteroaliphatic radical, a bivalent aryl radical, or a bivalent heteroaryl radical; and $R^{Lipid}$ each independently is

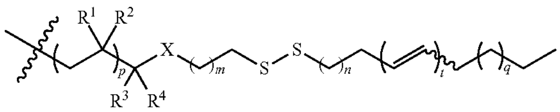

wherein:

$R^1$ and $R^2$ are H, OH, $NHR^{30}$, or SH;

$R^3$ and $R^4$ are both H; or $R^3$ and $R^4$ are taken together to form an oxo (=O) group;

X is $CH_2$, O, $NR^{30}$, or S;

$R^{30}$ is H, $C_{1-6}$ alkyl, $C_{1-6}$ alkenyl, or $C_{1-6}$ alkynyl;

m is an integer selected from 1-3;

n is an integer selected from 1-14;

p is 0 or 1;

q is an integer selected from 1-10; and t is 0, 1, or 2.

In certain embodiments, $R^{Head}$ is

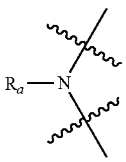

or

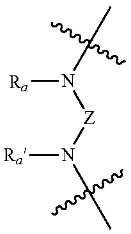

.

In certain embodiments, $R^a$ and $R^{a'}$ are $R^{Lipid}$, H, or $C_1$-$C_{20}$ alkyl.

In certain embodiments, $R^{Head}$ is derived from a compound selected from the group consisting of

113

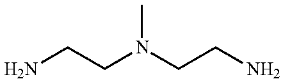

-continued

200

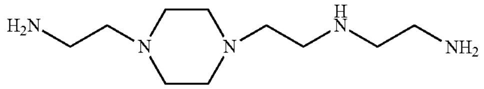

304

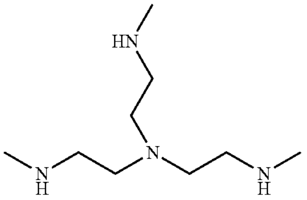

306

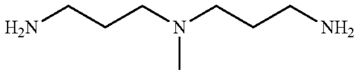

400

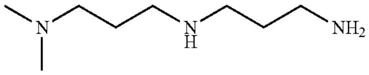

401

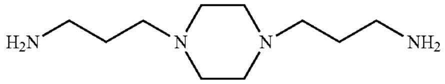

In certain embodiments, $R^1$ and $R^2$ are H. In certain embodiments, $R^1$ is H; and $R^2$ is OH.

In certain embodiments, $R^3$ and $R^4$ are H. In certain embodiments, $R^3$ and $R^4$ are taken together to form an oxo (=O) group.

In certain embodiments, Z is $CH_2$, O, or $NR^{30}$. In certain embodiments, Z is $CH_2$. In certain embodiments, Z is O. In certain embodiments, Z is $NR^{30}$.

In certain embodiments, m is 1 or 2.

In certain embodiments, n is an integer selected from 4-12. In certain embodiments, n is an integer selected from 6-10.

In certain embodiments, p is 0. In certain embodiments, p is 1.

In certain embodiments, q is an integer selected from 2-8. In certain embodiments, q is an integer selected from 4-8.

In certain embodiments, t is 0. In certain embodiments, t is 1.

In certain embodiments, $R^{Lipid}$ each independently is selected from the group consisting of

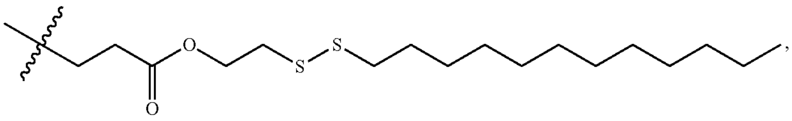

,

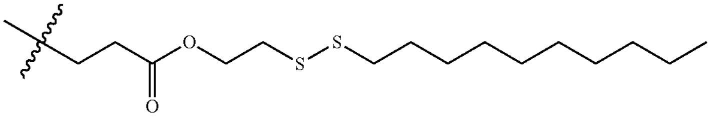

,

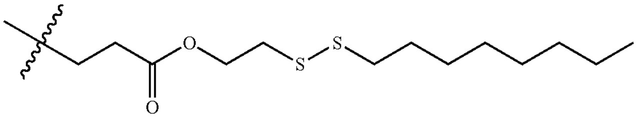

,

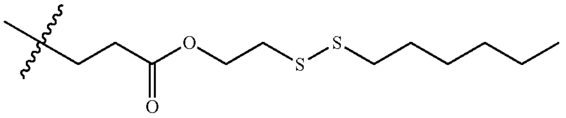

,

-continued
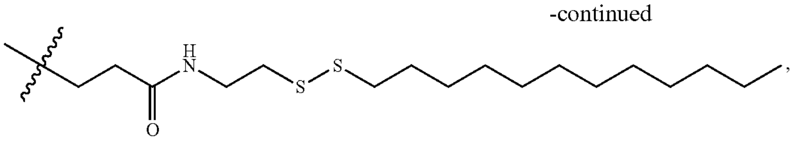,
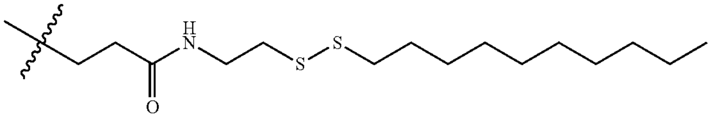,
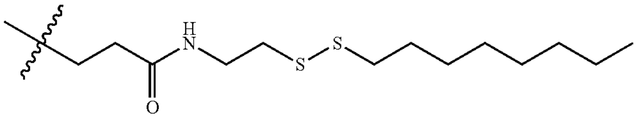,
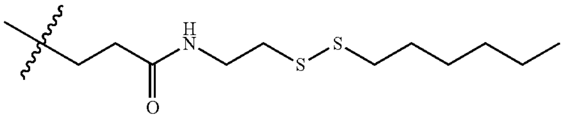,
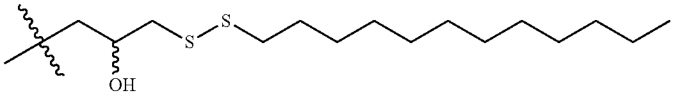,
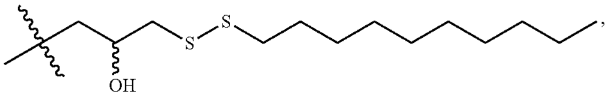, 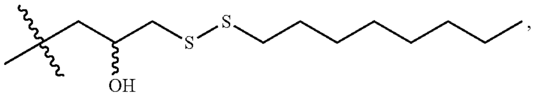, and
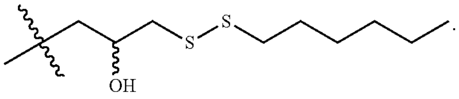.
In certain embodiments, the lipid is selected from the group consisting of
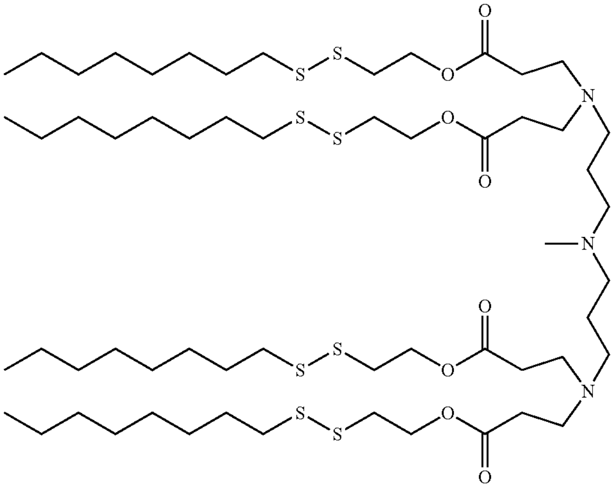, -continued

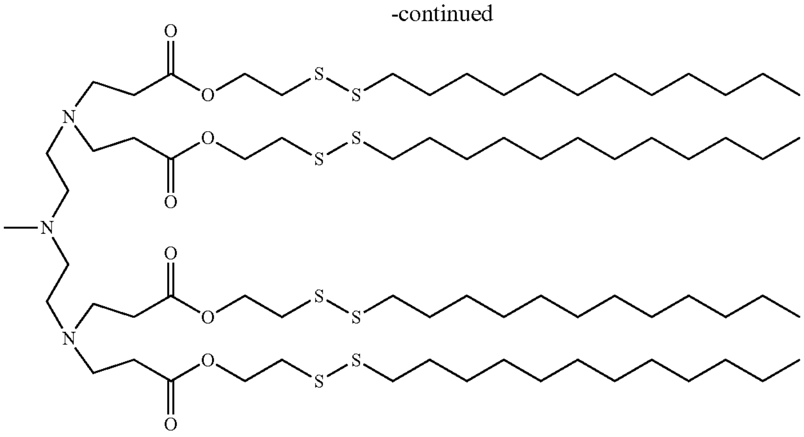

, and

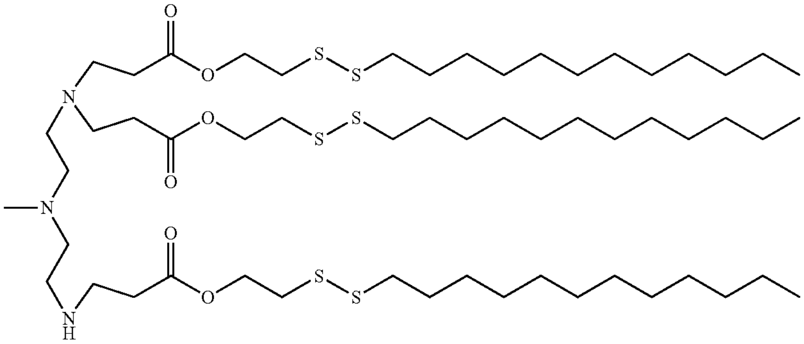

.

In certain embodiments, the ratio of the lipid to the CRISPR/Cas9 mRNA is about 3:1 to about 15:1. In certain embodiments, the ratio of the lipid to the CRISPR/Cas9 mRNA is about 7.5:1.

In certain embodiments, the lipidoid nanoparticle further comprises cholesterol.

In certain embodiments, the ratio of the lipid to the cholesterol is about 1:1 to about 2:1.

In certain embodiments, the lipidoid nanoparticle further comprising DOPE, DSPC, or DOPC, and DMG-PEG2K, wherein DSPC has the structure:

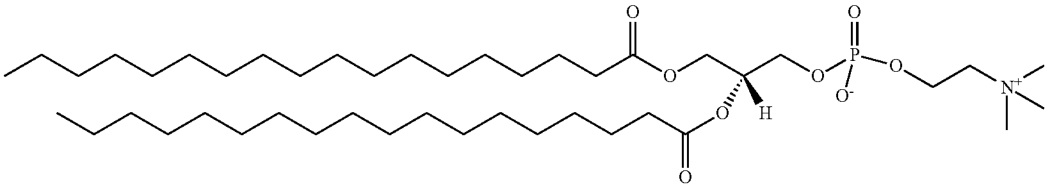

;

DOPE has the structure:

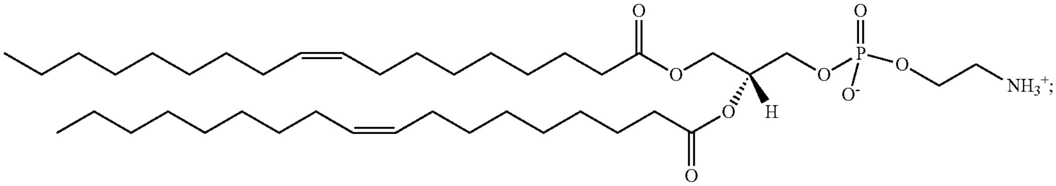

;

DOPC has the structure:

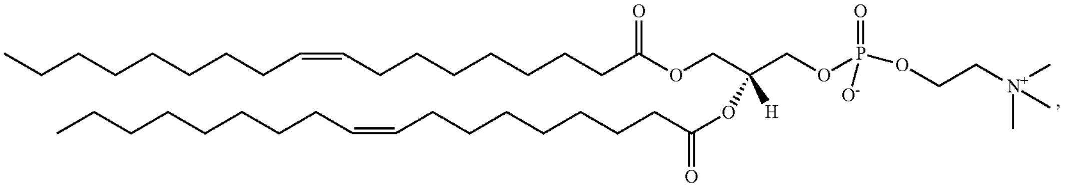 [SMILES: CCCCCCCC/C=C\CCCCCCCC(=O)OC[C@H](COP(=O)([O-])OCC[N+](C)(C)C)OC(=O)CCCCCCC/C=C\CCCCCCCC]

and DMG-PEG2K has the structure:

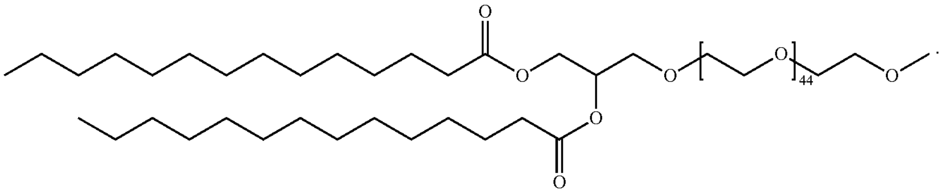

In certain embodiments, the lipidoid nanoparticle further comprising DOPC and DMG-PEG2K.

In certain embodiments, the ratio of the lipid to the DOPC is about 4:1 to about 6:1 and the ratio of the lipid to the DMG-PEG2K is about 4:1 to about 100:1 to about 4:1 to about 20:1.

In certain embodiments, the lipidoid nanoparticle has a particle size of about 25 nm to about 1000 nm. In certain embodiments, the lipidoid nanoparticle has a particle size of about 50 nm to about 500 nm.

In certain embodiments, the human lipoprotein metabolism disorder is associated with loss-of-function mutations in ANGPTL3 gene.

In certain embodiments, the cardiovascular disease is associated with proprotein convertase subtilisin/kexin type 9 gene (PCSK9).

In certain embodiments, the human lipoprotein metabolism disorder is associated with reduction of plasma high density lipoprotein cholesterol, serum low density lipoprotein cholesterol, or triglycerides level.

In certain embodiments, the human lipoprotein metabolism disorder is associated with low levels of plasma high density lipoprotein cholesterol, high levels of serum low density lipoprotein cholesterol, or high levels of triglycerides.

In certain embodiments, the cardiovascular disease is selected from the group consisting of homozygous familial hypercholesterolemia, and hypercholesterolemia.

In another aspect, the present disclosure provides lipids selected from the group consisting of

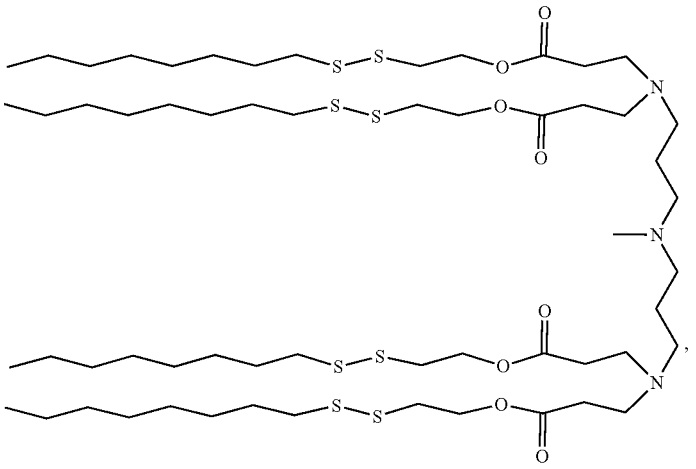

-continued

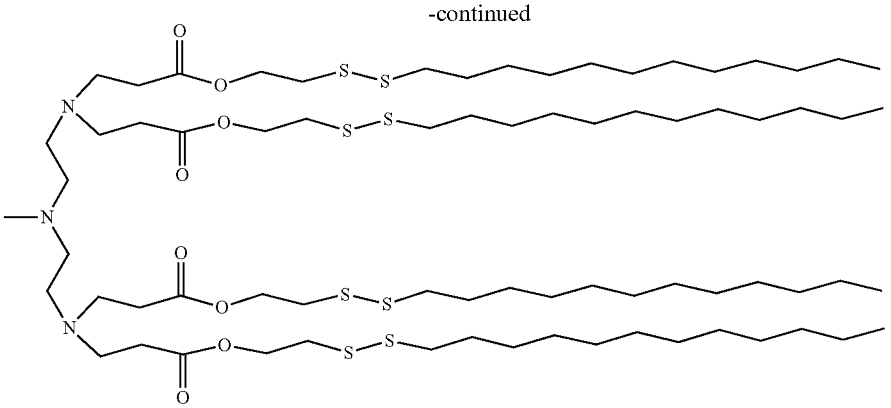

, and

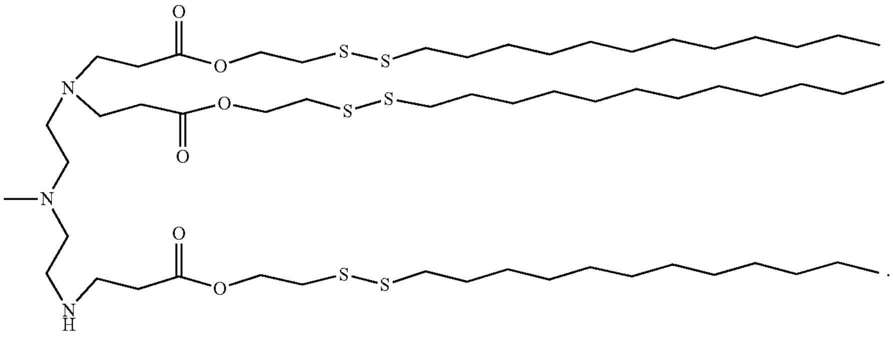

.

Definitions

Unless otherwise defined herein, scientific and technical terms used in this application shall have the meanings that are commonly understood by those of ordinary skill in the art. Generally, nomenclature used in connection with, and techniques of, chemistry, cell and tissue culture, molecular biology, cell and cancer biology, neurobiology, neurochemistry, virology, immunology, microbiology, pharmacology, genetics and protein and nucleic acid chemistry, described herein, are those well-known and commonly used in the art.

The methods and techniques of the present disclosure are generally performed, unless otherwise indicated, according to conventional methods well known in the art and as described in various general and more specific references that are cited and discussed throughout this specification. See, e.g. "Principles of Neural Science", McGraw-Hill Medical, New York, N.Y. (2000); Motulsky, "Intuitive Biostatistics", Oxford University Press, Inc. (1995); Lodish et al., "Molecular Cell Biology, 4th ed.", W. H. Freeman & Co., New York (2000); Griffiths et al., "Introduction to Genetic Analysis, 7th ed.", W. H. Freeman & Co., N.Y. (1999); and Gilbert et al., "Developmental Biology, 6th ed.", Sinauer Associates, Inc., Sunderland, MA (2000).

Chemistry terms used herein, unless otherwise defined herein, are used according to conventional usage in the art, as exemplified by "The McGraw-Hill Dictionary of Chemical Terms", Parker S., Ed., McGraw-Hill, San Francisco, C.A. (1985).

As used herein, the terms "optional" or "optionally" mean that the subsequently described event or circumstance may occur or may not occur, and that the description includes instances where the event or circumstance occurs as well as instances in which it does not. For example, "optionally substituted alkyl" refers to the alkyl may be substituted as well as where the alkyl is not substituted.

It is understood that substituents and substitution patterns on the compounds of the present invention can be selected by one of ordinary skilled person in the art to result chemically stable compounds which can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

As used herein, the term "optionally substituted" refers to the replacement of one to six hydrogen radicals in a given structure with the radical of a specified substituent including, but not limited to: hydroxyl, hydroxyalkyl, alkoxy, halogen, alkyl, nitro, silyl, acyl, acyloxy, aryl, cycloalkyl, heterocyclyl, amino, aminoalkyl, cyano, haloalkyl, haloalkoxy, —OCO—$CH_2$—O-alkyl, —OP(O)(O-alkyl)$_2$ or —$CH_2$—OP(O)(O-alkyl)$_2$. Preferably, "optionally substituted" refers to the replacement of one to four hydrogen radicals in a given structure with the substituents mentioned above. More preferably, one to three hydrogen radicals are replaced by the substituents as mentioned above. It is understood that the substituent can be further substituted.

Articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

As used herein, the term "alkyl" refers to saturated aliphatic groups, including but not limited to $C_1$-$C_{10}$ straight-chain alkyl groups or $C_1$-$C_{10}$ branched-chain alkyl groups. Preferably, the "alkyl" group refers to $C_1$-$C_6$ straight-chain alkyl groups or $C_1$-$C_6$ branched-chain alkyl groups. Most preferably, the "alkyl" group refers to $C_1$-$C_4$ straight-chain alkyl groups or $C_1$-$C_4$ branched-chain alkyl groups. Examples of "alkyl" include, but are not limited to, methyl, ethyl, 1-propyl, 2-propyl, n-butyl, sec-butyl, tert-butyl, 1-pentyl, 2-pentyl, 3-pentyl, neo-pentyl, 1-hexyl, 2-hexyl, 3-hexyl, 1-heptyl, 2-heptyl, 3-heptyl, 4-heptyl, 1-octyl, 2-octyl, 3-octyl or 4-octyl and the like. The "alkyl" group may be optionally substituted.

The term "acyl" is art-recognized and refers to a group represented by the general formula hydrocarbylC(O)—, preferably alkylC(O)—.

The term "acylamino" is art-recognized and refers to an amino group substituted with an acyl group and may be represented, for example, by the formula hydrocarbylC(O)NH—.

The term "acyloxy" is art-recognized and refers to a group represented by the general formula hydrocarbylC(O)O—, preferably alkylC(O)O—.

The term "alkoxy" refers to an alkyl group having an oxygen attached thereto. Representative alkoxy groups include methoxy, ethoxy, propoxy, tert-butoxy and the like.

The term "alkoxyalkyl" refers to an alkyl group substituted with an alkoxy group and may be represented by the general formula alkyl-O-alkyl.

The term "alkyl" refers to saturated aliphatic groups, including straight-chain alkyl groups, branched-chain alkyl groups, cycloalkyl (alicyclic) groups, alkyl-substituted cycloalkyl groups, and cycloalkyl-substituted alkyl groups. In preferred embodiments, a straight chain or branched chain alkyl has 30 or fewer carbon atoms in its backbone (e.g., $C_{1-30}$ for straight chains, $C_{3-30}$ for branched chains), and more preferably 20 or fewer.

Moreover, the term "alkyl" as used throughout the specification, examples, and claims is intended to include both unsubstituted and substituted alkyl groups, the latter of which refers to alkyl moieties having substituents replacing a hydrogen on one or more carbons of the hydrocarbon backbone, including haloalkyl groups such as trifluoromethyl and 2,2,2-trifluoroethyl, etc.

The term "$C_{x-y}$" or "$C_{x-Cy}$", when used in conjunction with a chemical moiety, such as, acyl, acyloxy, alkyl, alkenyl, alkynyl, or alkoxy is meant to include groups that contain from x to y carbons in the chain. $C_0$alkyl indicates a hydrogen where the group is in a terminal position, a bond if internal. A $C_{1-6}$ alkyl group, for example, contains from one to six carbon atoms in the chain.

The term "alkylamino", as used herein, refers to an amino group substituted with at least one alkyl group.

The term "alkylthio", as used herein, refers to a thiol group substituted with an alkyl group and may be represented by the general formula alkylS—.

The term "amide", as used herein, refers to a group

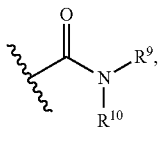

wherein $R^9$ and $R^{10}$ each independently represent a hydrogen or hydrocarbyl group, or $R^9$ and $R^{10}$ taken together with the N atom to which they are attached complete a heterocycle having from 4 to 8 atoms in the ring structure.

The terms "amine" and "amino" are art-recognized and refer to both unsubstituted and substituted amines and salts thereof, e.g., a moiety that can be represented by

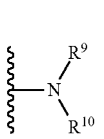 or 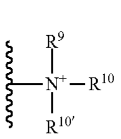 , wherein $R^9$, $R^{10}$, and $R^{10'}$ each independently represent a hydrogen or a hydrocarbyl group, or $R^9$ and $R^{10}$ taken together with the N atom to which they are attached complete a heterocycle having from 4 to 8 atoms in the ring structure.

The term "aminoalkyl", as used herein, refers to an alkyl group substituted with an amino group.

The term "aralkyl", as used herein, refers to an alkyl group substituted with an aryl group.

The term "aryl" as used herein include substituted or unsubstituted single-ring aromatic groups in which each atom of the ring is carbon. Preferably the ring is a 5- to 7-membered ring, more preferably a 6-membered ring. The term "aryl" also includes polycyclic ring systems having two or more cyclic rings in which two or more carbons are common to two adjoining rings wherein at least one of the rings is aromatic, e.g., the other cyclic rings can be cycloalkyls, cycloalkenyls, cycloalkynyls, aryls, heteroaryls, and/or heterocyclyls. Aryl groups include benzene, naphthalene, phenanthrene, phenol, aniline, and the like.

The term "carbamate" is art-recognized and refers to a group

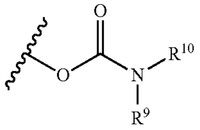 or 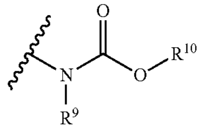 , wherein $R^9$ and $R^{10}$ independently represent hydrogen or a hydrocarbyl group.

The term "carbocyclylalkyl", as used herein, refers to an alkyl group substituted with a carbocycle group.

The term "carbocycle" includes 5-7 membered monocyclic and 8-12 membered bicyclic rings. Each ring of a bicyclic carbocycle may be selected from saturated, unsaturated and aromatic rings. Carbocycle includes bicyclic molecules in which one, two or three or more atoms are shared between the two rings. The term "fused carbocycle" refers to a bicyclic carbocycle in which each of the rings shares two adjacent atoms with the other ring. Each ring of a fused carbocycle may be selected from saturated, unsaturated and aromatic rings. In an exemplary embodiment, an aromatic ring, e.g., phenyl, may be fused to a saturated or unsaturated ring, e.g., cyclohexane, cyclopentane, or cyclohexene. Any combination of saturated, unsaturated and aromatic bicyclic rings, as valence permits, is included in the definition of carbocyclic. Exemplary "carbocycles" include cyclopentane, cyclohexane, bicyclo[2.2.1]heptane, 1,5-cyclooctadiene, 1,2,3,4-tetrahydronaphthalene, bicyclo[4.2.0]oct-3-ene, naphthalene and adamantane. Exemplary fused carbocycles include decalin, naphthalene, 1,2,3,4-tetrahydronaphthalene, bicyclo[4.2.0]octane, 4,5,6,7-tetrahydro-1H-indene and bicyclo[4.1.0]hept-3-ene. "Carbocycles" may be substituted at any one or more positions capable of bearing a hydrogen atom.

The term "carbocyclylalkyl", as used herein, refers to an alkyl group substituted with a carbocycle group.

The term "carbonate" is art-recognized and refers to a group $—OCO_2—$.

The term "carboxy", as used herein, refers to a group represented by the formula $—CO_2H$.

The term "ester", as used herein, refers to a group $—C(O)OR^9$ wherein $R^9$ represents a hydrocarbyl group.

The term "ether", as used herein, refers to a hydrocarbyl group linked through an oxygen to another hydrocarbyl group. Accordingly, an ether substituent of a hydrocarbyl group may be hydrocarbyl-O—. Ethers may be either symmetrical or unsymmetrical. Examples of ethers include, but are not limited to, heterocycle-O-heterocycle and aryl-O—heterocycle. Ethers include "alkoxyalkyl" groups, which may be represented by the general formula alkyl-O-alkyl.

The terms "halo" and "halogen" as used herein means halogen and includes chloro, fluoro, bromo, and iodo.

The terms "hetaralkyl" and "heteroaralkyl", as used herein, refers to an alkyl group substituted with a hetaryl group.

The terms "heteroaryl" and "hetaryl" include substituted or unsubstituted aromatic single ring structures, preferably 5- to 7-membered rings, more preferably 5- to 6-membered rings, whose ring structures include at least one heteroatom, preferably one to four heteroatoms, more preferably one or two heteroatoms. The terms "heteroaryl" and "hetaryl" also include polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Heteroaryl groups include, for example, pyrrole, furan, thiophene, imidazole, oxazole, thiazole, pyrazole, pyridine, pyrazine, pyridazine, and pyrimidine, and the like.

The term "heteroatom" as used herein means an atom of any element other than carbon or hydrogen. Preferred heteroatoms are nitrogen, oxygen, and sulfur.

The term "heterocyclylalkyl", as used herein, refers to an alkyl group substituted with a heterocycle group.

The terms "heterocyclyl", "heterocycle", and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The terms "heterocyclyl" and "heterocyclic" also include polycyclic ring systems having two or more cyclic rings in which two or more carbons are common to two adjoining rings wherein at least one of the rings is heterocyclic, e.g., the other cyclic rings can be cycloalkyls, cycloalkenyls, cycloalkynyls, aryls, heteroaryls, and/or heterocyclyls. Heterocyclyl groups include, for example, piperidine, piperazine, pyrrolidine, morpholine, lactones, lactams, and the like.

The term "hydrocarbyl", as used herein, refers to a group that is bonded through a carbon atom that does not have a =O or =S substituent, and typically has at least one carbon-hydrogen bond and a primarily carbon backbone, but may optionally include heteroatoms. Thus, groups like methyl, ethoxyethyl, 2-pyridyl, and even trifluoromethyl are considered to be hydrocarbyl for the purposes of this application, but substituents such as acetyl (which has a =O substituent on the linking carbon) and ethoxy (which is linked through oxygen, not carbon) are not. Hydrocarbyl groups include, but are not limited to aryl, heteroaryl, carbocycle, heterocycle, alkyl, alkenyl, alkynyl, and combinations thereof.

The term "hydroxyalkyl", as used herein, refers to an alkyl group substituted with a hydroxy group.

The term "lower" when used in conjunction with a chemical moiety, such as, acyl, acyloxy, alkyl, alkenyl, alkynyl, or alkoxy is meant to include groups where there are ten or fewer atoms in the substituent, preferably six or fewer. A "lower alkyl", for example, refers to an alkyl group that contains ten or fewer carbon atoms, preferably six or fewer. In certain embodiments, acyl, acyloxy, alkyl, alkenyl, alkynyl, or alkoxy substituents defined herein are respectively lower acyl, lower acyloxy, lower alkyl, lower alkenyl, lower alkynyl, or lower alkoxy, whether they appear alone or in combination with other substituents, such as in the recitations hydroxyalkyl and aralkyl (in which case, for example, the atoms within the aryl group are not counted when counting the carbon atoms in the alkyl substituent).

The terms "polycyclyl", "polycycle", and "polycyclic" refer to two or more rings (e.g., cycloalkyls, cycloalkenyls, cycloalkynyls, aryls, heteroaryls, and/or heterocyclyls) in which two or more atoms are common to two adjoining rings, e.g., the rings are "fused rings". Each of the rings of the polycycle can be substituted or unsubstituted. In certain embodiments, each ring of the polycycle contains from 3 to 10 atoms in the ring, preferably from 5 to 7.

The term "sulfate" is art-recognized and refers to the group $—OSO_3H$, or a pharmaceutically acceptable salt thereof.

The term "sulfonamide" is art-recognized and refers to the group represented by the general formulae

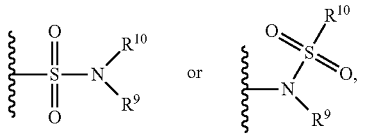

or wherein $R^9$ and $R^{10}$ independently represents hydrogen or hydrocarbyl.

The term "sulfoxide" is art-recognized and refers to the group —S(O)—.

The term "sulfonate" is art-recognized and refers to the group $SO_3H$, or a pharmaceutically acceptable salt thereof.

The term "sulfone" is art-recognized and refers to the group $—S(O)_2—$.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of this invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, a phosphoryl, a phosphate, a phosphonate, a phosphinate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety. It will be understood by those skilled in the art that the moieties substituted on the hydrocarbon chain can themselves be substituted, if appropriate.

The term "thioalkyl", as used herein, refers to an alkyl group substituted with a thiol group.

The term "thioester", as used herein, refers to a group —C(O)S$R^9$ or —SC(O)$R^9$ wherein $R^9$ represents a hydrocarbyl.

The term "thioether", as used herein, is equivalent to an ether, wherein the oxygen is replaced with a sulfur.

The term "urea" is art-recognized and may be represented by the general formula

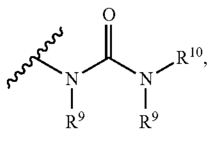

wherein $R^9$ and $R^{10}$ independently represent hydrogen or a hydrocarbyl.

The term "modulate" as used herein includes the inhibition or suppression of a function or activity (such as cell proliferation) as well as the enhancement of a function or activity.

The phrase "pharmaceutically acceptable" is art-recognized. In certain embodiments, the term includes compositions, excipients, adjuvants, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Salt" is used herein to refer to an acid addition salt or a basic addition salt.

Many of the compounds useful in the methods and compositions of this disclosure have at least one stereogenic center in their structure. This stereogenic center may be present in a R or a S configuration, said R and S notation is used in correspondence with the rules described in Pure Appl. Chem. (1976), 45, 11-30. The disclosure contemplates all stereoisomeric forms such as enantiomeric and diastereoisomeric forms of the compounds, salts, prodrugs or mixtures thereof (including all possible mixtures of stereoisomers). See, e.g., WO 01/062726.

Furthermore, certain compounds which contain alkenyl groups may exist as Z (zusammen) or E (entgegen) isomers. In each instance, the disclosure includes both mixture and separate individual isomers.

Some of the compounds may also exist in tautomeric forms. Such forms, although not explicitly indicated in the formulae described herein, are intended to be included within the scope of the present disclosure.

"Pharmaceutically acceptable" means approved or approvable by a regulatory agency of the Federal or a state government or the corresponding agency in countries other than the United States, or that is listed in the U.S. Pharmacopoeia or other generally recognized pharmacopoeia for use in animals, and more particularly, in humans.

"Pharmaceutically acceptable salt" refers to a salt of a compound of the invention that is pharmaceutically acceptable and that possesses the desired pharmacological activity of the parent compound. In particular, such salts are nontoxic may be inorganic or organic acid addition salts and base addition salts. Specifically, such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethanedisulfonic acid, 2-hydroxyethanesulfonic acid, benzenesulfonic acid, chlorobenzenesulfonic acid, 2-naphthalenesulfonic acid, 4-toluenesulfonic acid, camphorsulfonic acid, 4-methylbicyclo [2.2.2]-oct-2-ene-1-carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, N-methylglucamine and the like. Salts further include, by way of example only, sodium potassium, calcium, magnesium, ammonium, tetraalkylammonium, and the like; and when the compound contains a basic functionality, salts of nontoxic organic or inorganic acids, such as hydrochloride, hydrobromide, tartrate, mesylate, acetate, maleate, oxalate and the like.

The term "pharmaceutically acceptable cation" refers to an acceptable cationic counterion of an acidic functional group. Such cations are exemplified by sodium, potassium, calcium, magnesium, ammonium, tetraalkylammonium cations, and the like (see, e.g., Berge, et al., J. Pharm. Sci. 66 (1):1-79 (January 77).

"Pharmaceutically acceptable vehicle" refers to a diluent, adjuvant, excipient or carrier with which a compound of the invention is administered.

"Pharmaceutically acceptable metabolically cleavable group" refers to a group which is cleaved in vivo to yield the parent molecule of the structural formula indicated herein. Examples of metabolically cleavable groups include —COR, —COOR, —CONRR and —$CH_2$OR radicals, where R is selected independently at each occurrence from alkyl, trialkylsilyl, carbocyclic aryl or carbocyclic aryl substituted with one or more of alkyl, halogen, hydroxy or alkoxy. Specific examples of representative metabolically cleavable groups include acetyl, methoxycarbonyl, benzoyl, methoxymethyl and trimethylsilyl groups.

"Prodrugs" refers to compounds, including derivatives of the compounds of the invention, which have cleavable groups and become by solvolysis or under physiological conditions the compounds of the invention which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, H., Design of Prodrugs, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides and anhydrides derived from acidic groups pendant on the compounds of this invention are particular prodrugs. In some cases it is desirable to prepare double ester type prodrugs such as (acyloxy)alkylesters or (alkoxycarbonyl)oxy)alkylesters. Particularly the $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of the invention.

"Solvate" refers to forms of the compound that are associated with a solvent or water (also referred to as "hydrate"), usually by a solvolysis reaction. This physical association includes hydrogen bonding. Conventional solvents include water, ethanol, acetic acid and the like. The compounds of the invention may be prepared e.g., in crystalline form and may be solvated or hydrated. Suitable solvates include pharmaceutically acceptable solvates, such as hydrates, and further include both stoichiometric solvates and non-stoichiometric solvates. In certain instances, the solvate will be capable of isolation, for example when one or more solvent molecules are incorporated in the crystal lattice of the crystalline solid. "Solvate" encompasses both solution-phase and isolable solvates. Representative solvates include hydrates, ethanolates and methanolates.

A "subject" to which administration is contemplated includes, but is not limited to, humans (i.e., a male or female of any age group, e.g., a pediatric subject (e.g., infant, child, adolescent) or adult subject (e.g., young adult, middle aged adult or senior adult) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human," "patient," and "subject" are used interchangeably herein.

An "effective amount" means the amount of a compound that, when administered to a subject for treating or preventing a disease, is sufficient to effect such treatment or prevention. The "effective amount" can vary depending on the compound, the disease and its severity, and the age, weight, etc., of the subject to be treated. A "therapeutically effective amount" refers to the effective amount for therapeutic treatment. A "prophylatically effective amount" refers to the effective amount for prophylactic treatment.

"Preventing" or "prevention" or "prophylactic treatment" refers to a reduction in risk of acquiring or developing a disease or disorder (i.e., causing at least one of the clinical symptoms of the disease not to develop in a subject not yet exposed to a disease-causing agent, or predisposed to the disease in advance of disease onset.

The term "prophylaxis" is related to "prevention," and refers to a measure or procedure the purpose of which is to prevent, rather than to treat or cure a disease. Non limiting examples of prophylactic measures may include the administration of vaccines; the administration of low molecular weight heparin to hospital patients at risk for thrombosis due, for example, to immobilization, and the administration of an anti-malarial agent such as chloroquine, in advance of a visit to a geographical region where malaria is endemic or the risk of contracting malaria is high.

"Treating" or "treatment" or "therapeutic treatment" of any disease or disorder refers, in one embodiment, to ameliorating the disease or disorder (i.e., arresting the disease or reducing the manifestation, extent or severity of at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In a further embodiment, "treating" or "treatment" relates to slowing the progression of the disease.

As used herein, the term "isotopic variant" refers to a compound that contains unnatural proportions of isotopes at one or more of the atoms that constitute such compound. For example, an "isotopic variant" of a compound can contain one or more non-radioactive isotopes, such as for example, deuterium ($^2$H or D), carbon-13 ($^{13}$C), nitrogen-15 ($^{15}$N), or the like. It will be understood that, in a compound where such isotopic substitution is made, the following atoms, where present, may vary, so that for example, any hydrogen may be "$^2$H/D, any carbon may be $^{13}$C, or any nitrogen may be $^{15}$N, and that the presence and placement of such atoms may be determined within the skill of the art. Likewise, the invention may include the preparation of isotopic variants with radioisotopes, in the instance for example, where the resulting compounds may be used for drug and/or substrate tissue distribution studies. The radio-active isotopes tritium, i.e., $^3$H, and carbon-14, i.e., $^{14}$C, are particularly useful for this purpose in view of their ease of incorporation and ready means of detection. Further, compounds may be prepared that are substituted with positron emitting isotopes, such as $^{11}$C, $^{18}$F, $^{15}$O and $^{13}$N, and would be useful in Positron Emission Topography (PET) studies for examining substrate receptor occupancy. All isotopic variants of the compounds provided herein, radioactive or not, are intended to be encompassed within the scope of the invention.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers."

Stereoisomers that are not mirror images of one another are termed "diastereomers" and those that are non-superimposable mirror images of each other are termed "enantiomers." When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+)- or (−)-isomers respectively). A chiral compound can exist as either individual enantiomer or as a mixture thereof. A mixture containing equal proportions of the enantiomers is called a "racemic mixture".

"Tautomers" refer to compounds that are interchangeable forms of a particular compound structure, and that vary in the displacement of hydrogen atoms and electrons. Thus, two structures may be in equilibrium through the movement of it electrons and an atom (usually H). For example, enols and ketones are tautomers because they are rapidly interconverted by treatment with either acid or base. Another example of tautomerism is the acid- and nitro-forms of phenylnitromethane, that are likewise formed by treatment with acid or base. Tautomeric forms may be relevant to the attainment of the optimal chemical reactivity and biological activity of a compound of interest.

As used herein a pure enantiomeric compound is substantially free from other enantiomers or stereoisomers of the compound (i.e., in enantiomeric excess). In other words, an "S" form of the compound is substantially free from the "R" form of the compound and is, thus, in enantiomeric excess of the "R" form. The term "enantiomerically pure" or "pure enantiomer" denotes that the compound comprises more than 95% by weight, more than 96% by weight, more than 97% by weight, more than 98% by weight, more than 98.5% by weight, more than 99% by weight, more than 99.2% by weight, more than 99.5% by weight, more than 99.6% by weight, more than 99.7% by weight, more than 99.8% by weight or more than 99.9% by weight, of the enantiomer. In certain embodiments, the weights are based upon total weight of all enantiomers or stereoisomers of the compound.

As used herein and unless otherwise indicated, the term "enantiomerically pure R-compound" refers to at least about 95% by weight R-compound and at most about 5% by weight S-compound, at least about 99% by weight R-compound and at most about 1% by weight S-compound, or at least about 99.9% by weight R-compound and at most about 0.1% by weight S-compound. In certain embodiments, the weights are based upon total weight of compound.

As used herein and unless otherwise indicated, the term "enantiomerically pure 5-compound" or "S-compound" refers to at least about 95% by weight S-compound and at most about 5% by weight R-compound, at least about 99% by weight S-compound and at most about 1% by weight R-compound or at least about 99.9% by weight S-compound and at most about 0.1% by weight R-compound. In certain embodiments, the weights are based upon total weight of compound.

In the compositions provided herein, an enantiomerically pure compound or a pharmaceutically acceptable salt, solvate, hydrate or prodrug thereof can be present with other active or inactive ingredients. For example, a pharmaceutical composition comprising enantiomerically pure R-compound can comprise, for example, about 90% excipient and about 10% enantiomerically pure R-compound. In certain embodiments, the enantiomerically pure R-compound in such compositions can, for example, comprise, at least about 95% by weight R-compound and at most about 5% by weight S-compound, by total weight of the compound. For example, a pharmaceutical composition comprising enantiomerically pure S-compound can comprise, for example, about 90% excipient and about 10% enantiomerically pure S-compound. In certain embodiments, the enantiomerically pure S-compound in such compositions can, for example, comprise, at least about 95% by weight S-compound and at most about 5% by weight R-compound, by total weight of the compound. In certain embodiments, the active ingredient can be formulated with little or no excipient or carrier.

The compounds of this invention may possess one or more asymmetric centers; such compounds can therefore be produced as individual (R)- or (S)-stereoisomers or as mixtures thereof.

Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art.

One having ordinary skill in the art of organic synthesis will recognize that the maximum number of heteroatoms in a stable, chemically feasible heterocyclic ring, whether it is aromatic or non-aromatic, is determined by the size of the ring, the degree of unsaturation and the valence of the heteroatoms. In general, a heterocyclic ring may have one to four heteroatoms so long as the heteroaromatic ring is chemically feasible and stable.

EXAMPLES

In order that the invention described herein may be more fully understood, the following examples are set forth. The examples described in this application are offered to illustrate the compounds, compositions, materials, device, and methods provided herein and are not to be construed in any way as limiting their scope.

I. CRISPR/Cas9 Genome Editing In Vivo Enabled by Bioreducible Lipid and Messenger RNA Nanoparticles

Materials and Methods

All chemicals used for lipid synthesis were purchased from Aladdin, TCI or Sigma-Aldrich and used as received. Firefly luciferase (L-7602) and Cas9 messenger RNA (mRNA) (L-7606) were purchased from Tri-Link Biotechnologies. Mouse serum PCSK9 was determined using a PCSK9 ELISA Kit (Sino Biological, China). Cell viability was determined using Alamar Blue assay or SRB cell proliferation and cytotoxicity assay kit (Yeasen Biotech Co., Ltd. China). Cy3-RNA (43 nt) were purchased from Biosyntech (Suzhou, China). gRNA targeting GFP was prepared according to our previous reports, sgRNA targeting mouse PCSK9 and human HPV18 was prepared using in vitro transcription according to reported methods. RFP-encoding mRNA was prepared using in vitro transcription method with pcDNA3.1-RFP (Yingrun, Changsha, China) as a template using the RiboMAX™ Large Scale RNA Production Systems (Promega, USA). Flow cytometry was performed on Beckman Coulter CytoFLEX. HeLa, A375 and HEK-GFP cells were maintained in DMEM (Sigma-Aldrich) supplemented with 10% FBS (Sigma-Aldrich) and 1% penicillin-streptomycin (Life Technologies). All animal care and experimental procedures were approved by the Institutional Animal Care and Use Committees (IUCAC) at National Center for Nanoscience and Technology of China (NCNTC).

TABLE 1

The information of sgRNA sequences

| SgRNA | SEQ ID NO: | Sequence (5'-3') |
|---|---|---|
| sgGFP | 1 | GGGCACGGGCAGCUUGCCGG |
| sgScr | 2 | GAUAAAUAACGCGCCCAACAC |
| sgHPV18 | 3 | GGGCGCUUUGAGGAUCCAACA |
| sgPCSK9 | 4 | CCCAUGUGGAGUACAUUGGUU |

Lipid Nanoparticle Formulation

The lipids were synthesized by heating amines and acrylate or acrylamide using the methods described according to our previous reports (9), and purified using flash chromatography on silica gel. To make the lipid nanoparticles for mRNA delivery, the purified lipids were mixed with cholesterol, DOPE and DSPE-PEG2000 at a weight/weight ratio of 16:8:4:1 in chloroform in a 2 mL vial, the organic solvent was evaporated under vacuum, the resulted mixtures was further dried overnight to form a thin layer film. The lipid film was hydrated using a mixed solution of ethanol/sodium acetate buffer (200 mM, pH=5.2) and added drop-wise to an aqueous solution of DSPE-PEG2000. The resulted nanoparticles were dialysed against phosphate buffered saline (PBS) to remove excessive ethanol.

Intracellular Delivery of Luciferase and RFP mRNA

To screen effective lipid nanoparticle for luciferase mRNA delivery, A375 cells were seeded in 24-well plate a day before experiment at a density of 50 K per well. At the day of experiment, 160 ng/mL luciferase mRNA was mixed with 3 μg/mL different lipid nanoparticles (all concentrations refer to the final RNA and lipid concentration added to cells) in a sodium acetate buffer (25 mM, pH=5.2), followed by 15 min. of incubation at room temperature. The resulted mRNA lipoplexes were then added to cells, and incubated with cells for additional 6 h before refreshing cell culture medium. The luciferase activity was assayed using a firefly luciferase activity assay kit according to the instruction of manufacturer (Promega, USA).

For the cytotoxicity assay of BAMEA-O16B/luciferase mRNA nanoparticles, HEK cells were treated with 160 ng/mL of luciferase mRNA nanoparticles or different lipids nanoparticles similarly to that of genome editing efficiency study. The cell viability was determined using Alamar Blue or SRB cell proliferation and cytotoxicity assay 24 h post-delivery.

For RFP mRNA delivery, HeLa cells seeded in 48-well plate (25 K cells per well) were treated with BAMEA-O16B/RFP mRNA nanoparticle at the optimized conditions for 8 h before changing fresh cell culture medium. The RFP expression profile was imaged using CLSM on an Olympus FV-IX81 confocal system or quantified by flow cytometry on a Beckman Coulter CytoFLEX 24 h post mRNA delivery.

Cellular Uptake and Endosome Escape Study of BAMEA-O16B/RNA Nanoparticles

To confirm the effectiveness of designing bioreducible lipid nanoparticle to promote RNA release in response to reductive intracellular environment, BAMEA-O16B or BAMEA-O16 was complexed with RFP mRNA at a weight ratio of 15:1 in a sodium acetate buffer (25 mM, pH=5.2), followed by 15 min. of incubation at room temperature. The resulted nanocomplexes were treated with 5 mM GSH for 4 h at 37° C. before agarose gel electrophoresis, and compared to mRNA nanocomplexes without GSH treatment.

For the cellular uptake study of RNA nanoparticles, a 43-nucleotide RNA labeled with Cy3 was mixed with BAMEA-O16B or BAMEA-O16 nanoparticle at a weight ratio of 30:1 before adding to HeLa cells. For the CLSM imaging study, HeLa cells were treated with Cy3-RNA nanoparticles for 8 h, and the endosome was co-stained using LysoTracker Green (ThermoFisher Scientific, USA). For the comparison of the cellular uptake efficiency of BAMEA-O16B or BAMEA-O16/RNA nanoparticles, cells treated with different concentrations of above RNA nanoparticles were analyzed using flow cytometry and quantifying Cy3-positive cells.

Cas9 mRNA/sgRNA Delivery and Genome Editing In Vitro

GFP-stably expressed HEK cells were seeded in 48-well plate a day before experiment at a density of 25 K per well. At the day of experiment, 13 nM GFP-targeting sgRNA was mixed with different doses of Cas9 mRNA and 5 μg/mL BAMEA-O16B (all concentrations refer to the final RNA and lipid concentration added to cells) in a sodium acetate buffer (25 mM, pH=5.2), followed by 15 min. of incubation at room temperature. The BAMEA-O16B/Cas9 mRNA/sgGFP nanoparticle was then added to cells and incubated for 10 h before changing fresh cell culture medium. The GFP expression profile was imaged using CLSM or quantified using flow cytometry analysis at different time points post Cas9 mRNA delivery, and normalized to cells without Cas9 mRNA/sgGFP delivery to determine genome editing efficiency. To further confirm the sequence-specific genome editing of Cas9 mRNA/sgGFP delivery, sgGFP was replaced with a scramble sgRNA, and delivered into HEK-GFP cells similarly to that of Cas9 mRNA/sgGFP delivery.

For the cytotoxicity assay of BAMEA-O16B/Cas9 mRNA/sgGFP nanoparticles, HEK cells were treated with different concentration of Cas9 mRNA nanoparticles similarly to that of genome editing efficiency study. The cell viability was determined using Alamar Blue 48 h post Cas9 mRNA delivery.

To confirm the effectiveness of BAMEA-O16B/Cas9 mRNA delivery to edit endogenous gene for potential gene therapy, HeLa cells seeded in 48-well plate was treated with BAMEA-O16B/Cas9 mRNA alone with sgHPV18 or a scramble RNA sequence similar to that of GFP knock out study, the cell viability was determined using Alamar Blue assay 48 h post Cas9 mRNA delivery.

Cas9 mRNA/sgRNA Delivery and Genome Editing In Vivo

For in vivo luciferase mRNA delivery, female athymic nude mice were injected via tail vein with BAMEA-O16B/Luci-mRNA nanoparticle at a mRNA dose of 0.6 mg/kg or same dose of free mRNA. 24 h post nanoparticle or free mRNA injection, the mice were sacrificed to harvest different tissues for bioluminescence imaging on an IVIS spectrum In Vivo imaging system (Perkin Elmer, USA). To study the delivery of mRNA into hepatocytes, BAMEA-O16B/RFP mRNA nanoparticle was injected to C57BL/6 mouse similarly to luciferase mRNA delivery. 24 h post nanoparticle delivery, the mice were sacrificed to harvest liver for fluorescence imaging study.

For in vivo Cas9 mRNA/Cy3-RNA delivery, female athymic nude mice were injected via tail vein with BAMEA-O16B/Cas9 mRNA/Cy3-RNA nanoparticle at dose of 9 mg/kg BAMEA-O16B, 0.6 mg/kg Cas9 mRNA and 0.8 mg/kg Cy3-RNA or same dose of free mRNA. 6 h post nanoparticle or free mRNA injection, the mice were sacrificed to harvest different tissues for bioluminescence imaging on an IVIS spectrum In Vivo imaging system (Perkin Elmer, USA).

For in vivo Cas9 mRNA delivery and PCSK9 gene editing, C57BL/6 mice were injected via tail vein with BAMEA-O16B/Cas9 mRNA/sgPCSK9 or BAMEA-O16B/Cas9 mRNA/sgRNA with a scramble sgRNA sequence at a dose of 9 mg/kg BAMEA-O16B, 0.6 mg/kg Cas9 mRNA and 0.8 mg/kg sgRNA. Two days after nanoparticle injection, the mice were sacrificed to withdraw mouse serum for PCSK9 and liver toxicity assay. Meanwhile, liver tissues were collected for H&E staining to study the possible liver injury of nanoparticle injections.

Example 1. Synthesis and Screening of Effective Lipids for mRNA Delivery

Figure 2A:
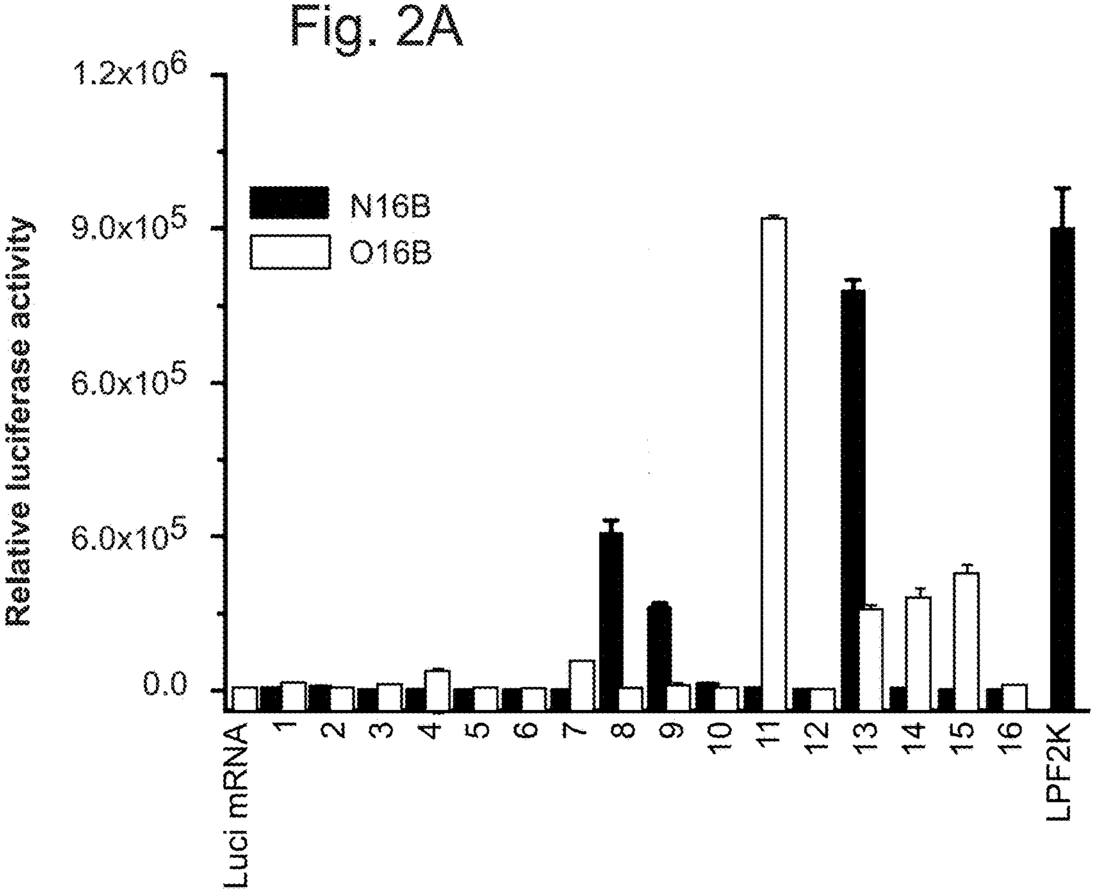
FIG. 2A is a bar graph depicting the Luciferase expression of A375 cells treated with luciferase mRNA alone (160 ng/mL) or in the form of nanocomplexes of different lipid nanoparticles.
Figure 2B:
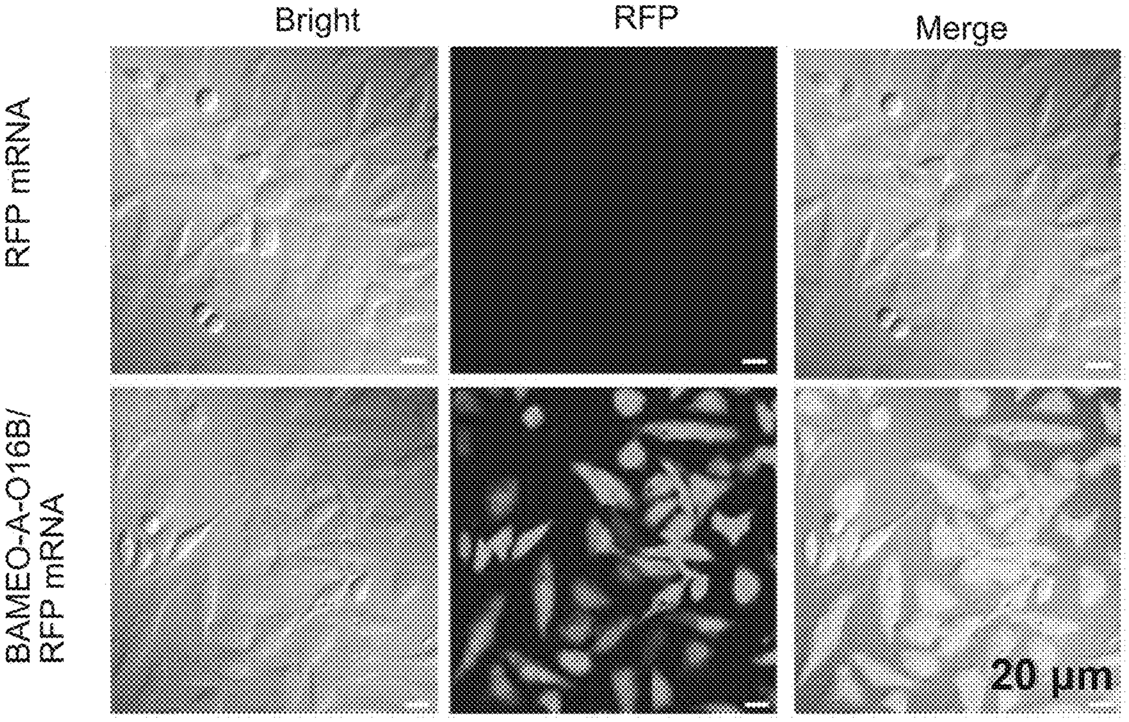
FIG. 2B are CLSM images depicting HeLa cells transfected with RFP mRNA alone (320 ng/mL) or in the form of BAMEA-O16B/RFP mRNA nanoparticles. Scale bars: 20 μm.
Figure 2C:
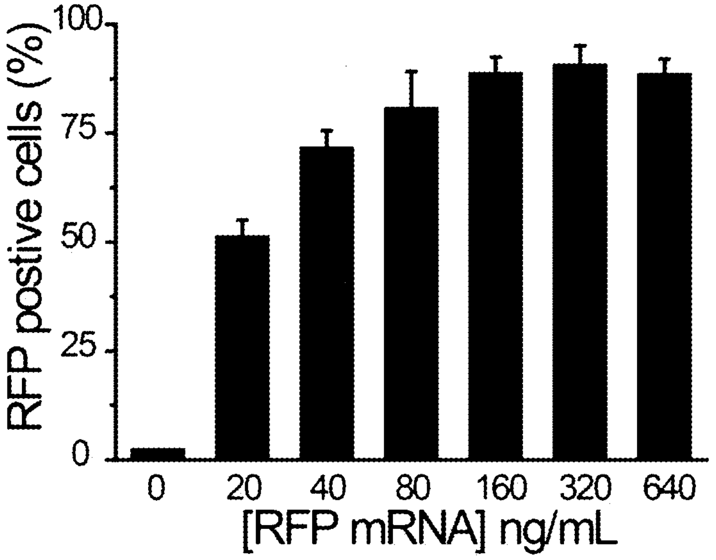
FIG. 2C is a bar graph depicting mRNA dose dependent RFP expression of HeLa cells treated with increased concentration of BAMEA-O16B/RFP mRNA. RFP expression profile was quantified 24 h after mRNA delivery.

FIGS. 2A-2C are graphs and images depicting the intracellular delivery of Luciferase and RFP mRNA.

Figure 6A:
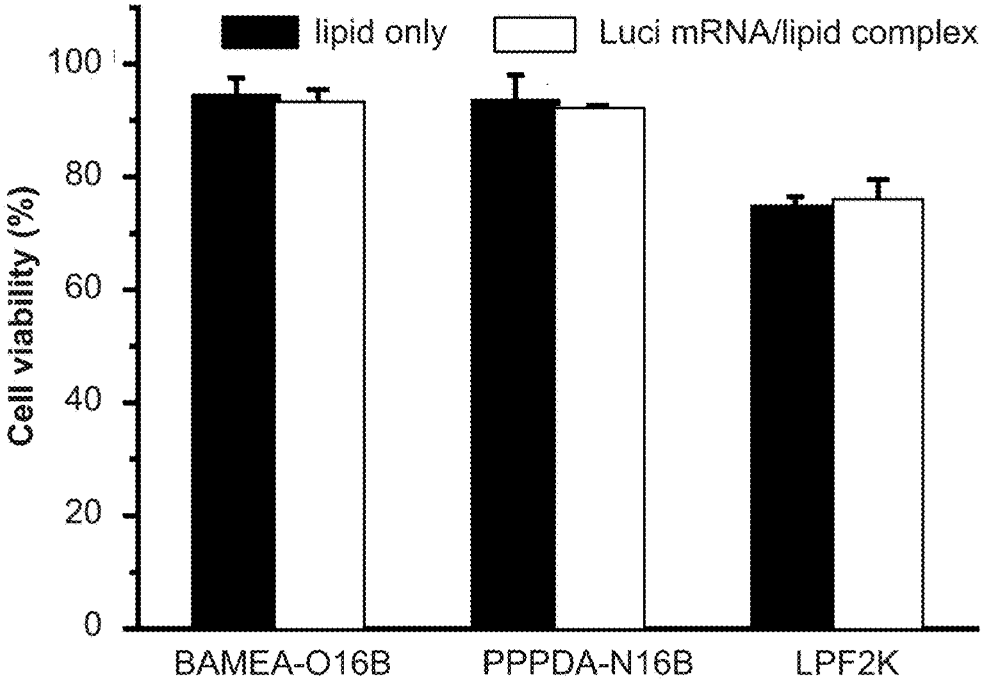
FIG. 6A is a bar graph depicting cytotoxicity assay of BAMEA-O16B, PPPDA-N16B, LPF2K or their mRNA nanocomplexes using Alarmar Blue assay 24 h post-delivery.
Figure 6B:
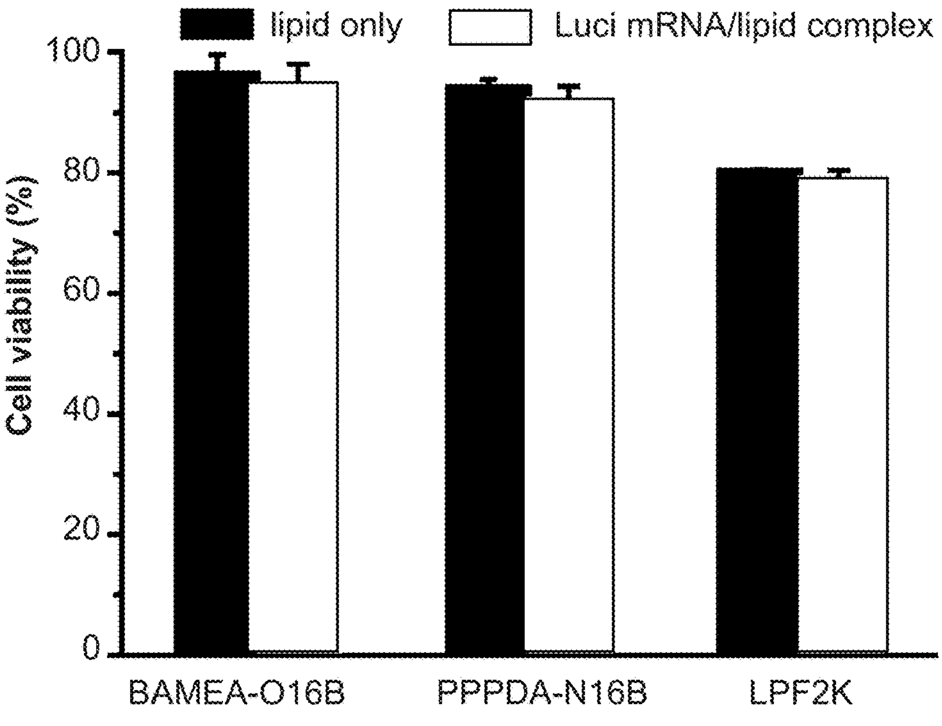
FIG. 6B is a bar graph depicting cytotoxicity assay of BAMEA-O16B, PPPDA-N16B, LPF2K or their mRNA nanocomplexes using sulforhodamine B (SRB) assay 24 h post-delivery.

The bioreducible lipids was synthesized by heating amine and acrylates or acrylamides featuring a disulfide bond according to our previous reports (FIG. 1A). The lipids were named by amine number or name followed by O16B or N16B to discriminate the use of acrylate or acrylamide, respectively (FIG. 1B). The as-purified lipids were formulated with cholesterol, 1, 2-dioleoyl-sn-glycero-3-phosphoethanolamine (DOPE), and DSPE-$PEG_{2000}$ for all cellular delivery experiments in this study (see Materials and Methods for details). To facilitate the screening of effective lipids for mRNA delivery, luciferase-encoding mRNA was assembled with different lipids at weight ratio of 1:15 to transfect A375 human melanoma cells. The luciferase expression of transfected A375 cells was measured and compared to cells treated with luciferase mRNA alone or luciferase mRNA complexed with a commercial transfection lipid, Lipofectamine 2000 (LPF2K). As shown in FIG. 2A, cells treated with mRNA alone did not show detectable luciferase expression, indicating that mRNA alone is not able to enter cells, while cells treated with the complexes of mRNA and lipids shown varied luciferase expression that depends on the amine and tail structure of the lipids. Two bioreducible lipids, BAMEA-O16B (amine 11) and PPPDA-N16B (amine 13) delivered luciferase mRNA in a comparable efficiency to that of LPF2K. A further study of the biocompatibility of the two lipids indicated that the mRNA lipoplexes of BAMEA-O16B and PPPDA-N16B showed a lower cytotoxicity than LPF2K (FIG. 6A and FIG. 6B), highlighting the advantage and necessity of designing combinatorial lipid nanoparticle for discovering efficient yet biocompatible nanocarriers for mRNA delivery. The representative lipid, BAMEA-O16B, is selected for detailed mRNA delivery and CRISPR/Cas9 genome editing studies.

The representative lipid BAMEA-O16B is a general nanocarrier for mRNA delivery, as evidenced by its capability and high efficiency to deliver red fluorescent protein (RFP)-encoding mRNA into HeLa cells. The treatment of human cervical cancer cells (HeLa) with BAMEA-O16B/RFP mRNA nanoparticles resulted in efficient RFP expression (FIG. 2B). Flow cytometry analysis (FIG. 2C) indicated that the RFP-positive cells is dependent on mRNA dose, and the transfection efficiency could be as high as 90% when 160 ng/mL of RFP mRNA was delivered into HeLa cells. Altogether, both luciferase and RFP mRNA delivery demonstrated the effectiveness of BAMEA-O16B nanoparticle for efficient yet safe mRNA delivery.

Example 2. mRNA Delivery Using BAMEA-O16B or BAMEA-O16

FIGS. 3A-3D are graphs and images depicting cellular uptake and endosome escape study of BAMEA-O16B/RNA nanoparticles.

FIGS. 4A-4D CRISPR/Cas9 mRNA delivery and genome editing in cultured cells.

Figure 3A:
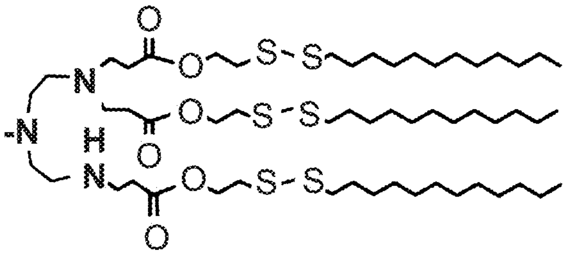
FIG. 3A shows the chemical structures of BAMEA-O16B and BAMEA-O16.
Figure 3A:
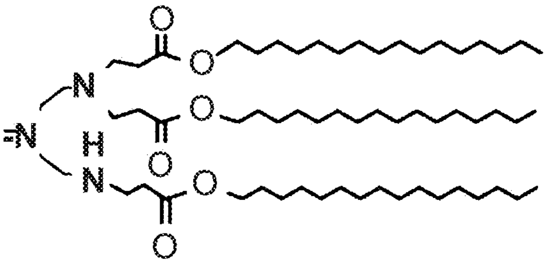
Figure 7:
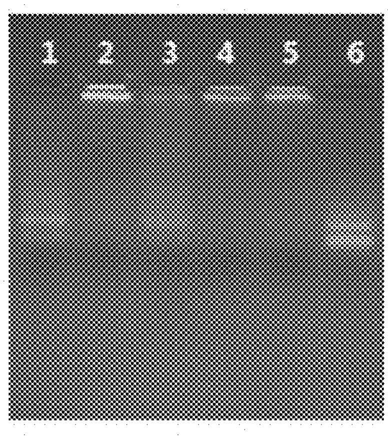
FIG. 7 is an agarose gel electrophoresis image depicting GSH-triggered mRNA release from BAMEA-O16B/mRNA complex.

To further elaborate that the integration of disulfide bonds into BAMEA-O16B promotes intracellular mRNA release to enhance mRNA transfection efficiency, we synthesized a control lipid with a chemical structure similar to BAMEA-O16B, while lacking the disulfide bond, named as BAMEA-O16 (FIG. 3A). Agarose gel electrophoresis study indicated that BAMEA-O16B and BAMEA-O16 showed comparable mRNA encapsulation efficiency (FIG. 7). Interestingly, glutathione (GSH) treatment (5 mM) resulted in the efficient release of mRNA from BAMEA-O16B/mRNA complex, but not from the BAMEA-O16/mRNA complexes. The similar mRNA encapsulation capability was further confirmed by the comparable size and zeta potential of the two mRNA complexes, as revealed by the dynamic light scattering (DLS) analysis (Table 2).

TABLE 2

Size and zeta-potential of representative lipid and lipid/mRNA nanoparticles

| Sample | Size (nm) | Zeta potential (mV) |
|---|---|---|
| BAMEA-O16 | 93.3 ± 2.3 | 26.4 ± 1.3 |
| BAMEA-O16/RFP mRNA | 138.5 ± 1.0 | 18.7 ± 0.8 |
| BAMEA-O16B | 108.7 ± 0.5 | 25.3 ± 0.9 |
| BAMEA-O16B/RFP mRNA | 154.4 ± 0.3 | 18.9 ± 3.8 |
| BAMEA-O16B/Cas9 mRNA/sgRNA | 233.6 ± 2.3 | 10.4 ± 0.6 |

Figure 3B:
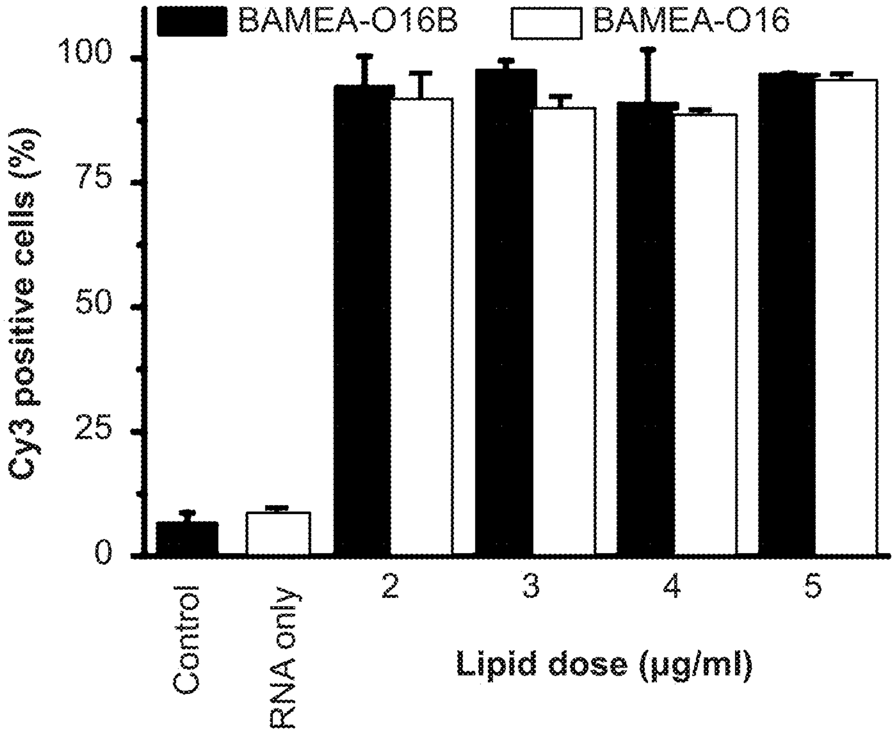
FIG. 3B is a bar graph depicting the cellular uptake efficiency of BAMEA-O16B/RNA nanoparticles.
Figure 3C:
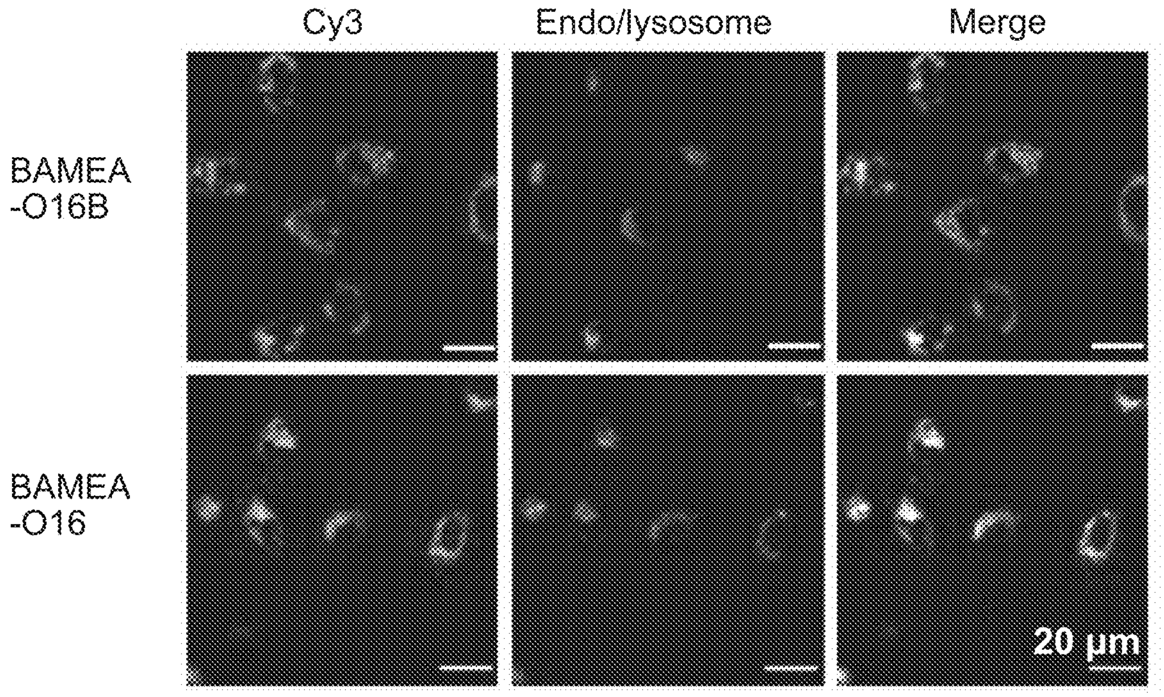
FIG. 3C are CLSM images of HeLa cells treated with BAMEA-O16B/Cy3-RNA OR BAMEA-O16/Cy3-RNA nanoparticles HeLa cells were delivered with 10 nM Cy3-RNA complexed with the lipids at indicated ratios for delivery, the endosome was co-stained using LysoTracker® Green (Scale bars: 20 μm).
Figure 3D:
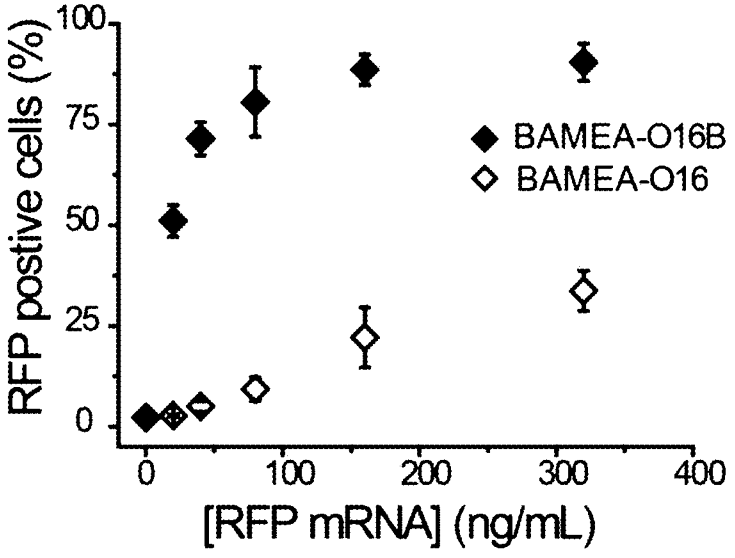
FIG. 3D is a plot depicting BAMEA-O16B/mRNA delivery shown an enhanced RFP expression in HeLa cells than that of BAMEA-O16 nanoparticles.

It is also of note that BAMEA-O16B or BAMEA-O16 showed a comparable RNA delivery efficiency. The treatment of HeLa cells with fluorescent-labeled RNA complexes (10 nM) of BAMEA-O16B or BAMEA-O16 resulted in RNA internalization efficiency higher than 90% at all different lipid and RNA ratios (FIG. 3B). Confocal laser scanning microscopy (CLSM) imaging of HeLa cells, however, indicated that the BAMEA-O16B/RNA treated cells shown a higher endosome escape efficiency than that of BAMEA-O16/RNA treatment (FIG. 3C), this is mostly due to the bioreducible nature of BAMEA-O16B that facilitates the release of RNA more efficiently in response to the reductive intracellular environment. Moreover, RFP mRNA delivery using BAMEA-O16B nanoparticles resulted in a higher RFP expression in HeLa cells than that of BAMEA-O16 facilitated mRNA delivery. For example, the delivery of 160 ng/mL RFP mRNA using BAMEA-O16B resulted in four-time fold enhancement of RFP expression than using BAMEA-O16 nanoparticles (FIG. 3D).

Figure 8:
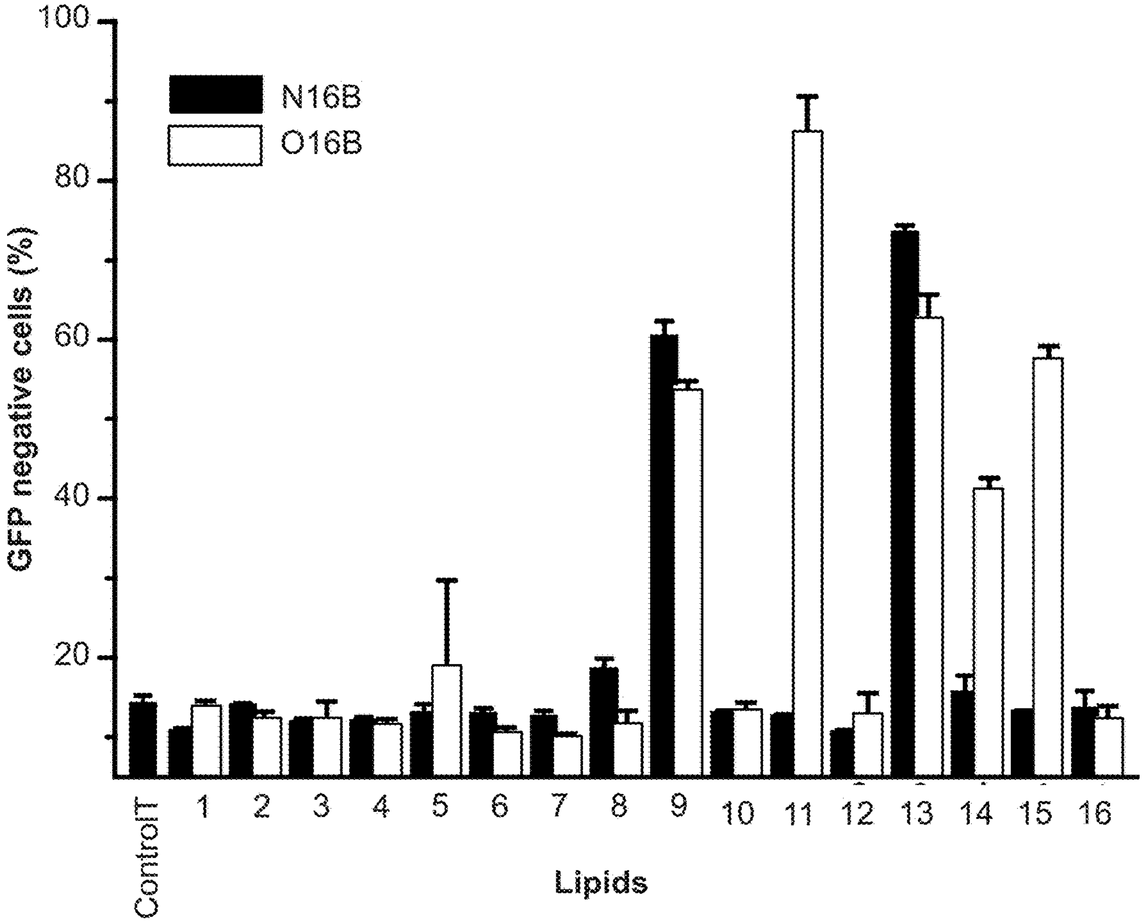
FIG. 8 is a bar graph depicting the GFP silencing after HEK-GFP cells were treated with Cas9 mRNA (160 ng/mL) and sgGFP (13 nM), nanocomplexes of different lipid nanoparticles the GFP expression was quantified at 48 h post mRNA delivery.
Figure 9:
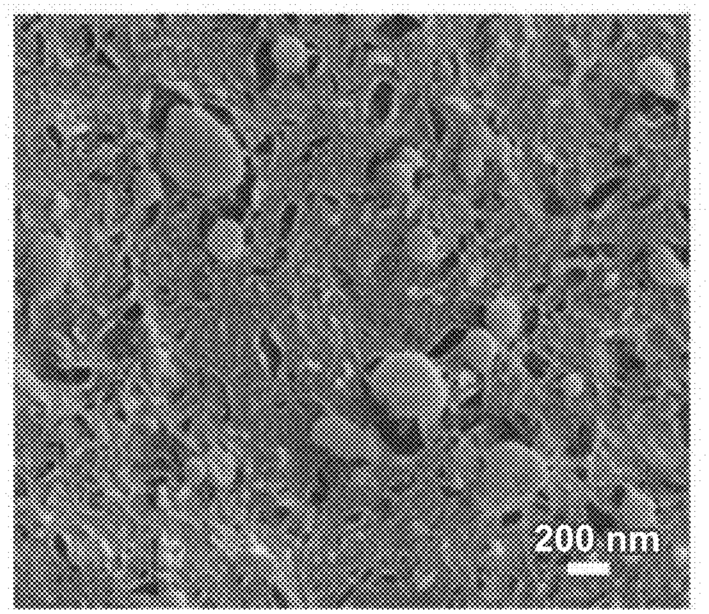
FIG. 9 is a scanning electron microscope image of BAMEA-O16B/Cas9 mRNA/sgRNA nanoparticles. Scale bar: 200 nm.
Figure 10:
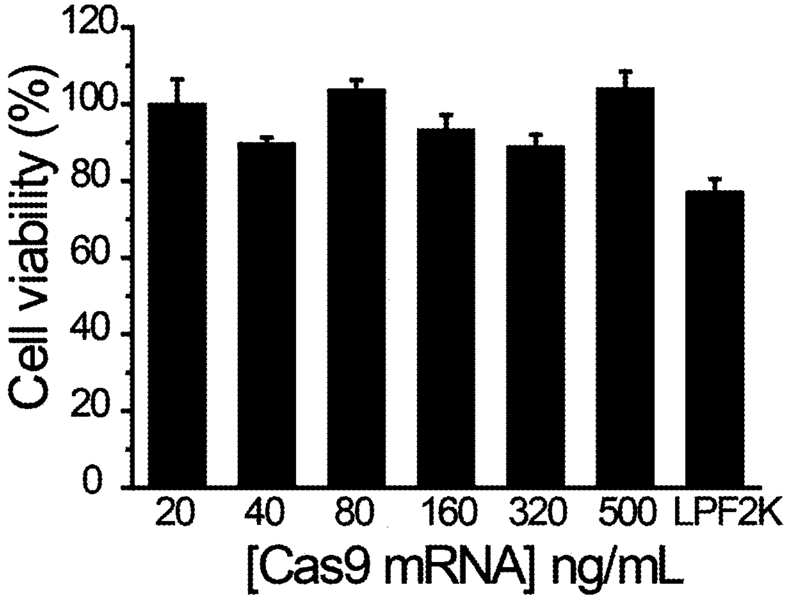
FIG. 10 is a bar graph depicting the cytotoxicity assay of BAMEA-O16B/Cas9 mRNA/sgRNA nanoparticles against HEK cells. HEK cells were treated with the nanocomplex composed of 5 μg/mL lipid and increased concentration of Cas9 mRNA/sgRNA for 10 h, followed by cell viability measurement using Alamar Blue assay.

Having demonstrated the effectiveness of using BAMEA-O16B for reporter mRNA delivery, the capability of BAMEA-O16B to simultaneously deliver Cas9 mRNA and sgRNA for genome editing was examined next. Cas9 mRNA is around 4500 nucleotides in size, it is much longer than luciferase or RFP mRNA (~1000 nt) and therefore much more difficult for intracellular delivery. To further elaborate the efficacy of the library of bioreducible for Cas9 mRNA delivery and genome editing, GFP stably-expressed HEK cells were treated with the lipid nanoparticle encapsulating Cas9 mRNA and GFP-targeting sgRNA, and monitored the GFP expression change before and after mRNA delivery. The on-target GFP genome editing could induce the shift of reading frame of GFP gene, and thereby preventing GFP expression. As shown in FIG. 8, seven of the thirty-two lipids can efficiently deliver Cas9 mRNA and sgRNA to knock down GFP expression of HEK cells, among which lipid BAMEA-O16B showed the highest genome editing and GFP knock out efficiency. It is found that the electrostatic interaction of BAMEA-O16B and Cas9 mRNA/sgRNA assembled well-dispersed nanoparticles around 230 nm in size (Table 2, FIG. 9). Meanwhile, the BAMEA-O16B/Cas9 mRNA nanocomplex is highly biocompatible for genome editing delivery. HEK cells treated with different concentrations of BAMEA-O16B/Cas9 mRNA nanocomplex all remained viability greater than 90%, which is also higher than HEK cells treated with LPF2K/Cas9 mRNA/sgRNA nanocomplex (FIG. 10).

Figure 4A:
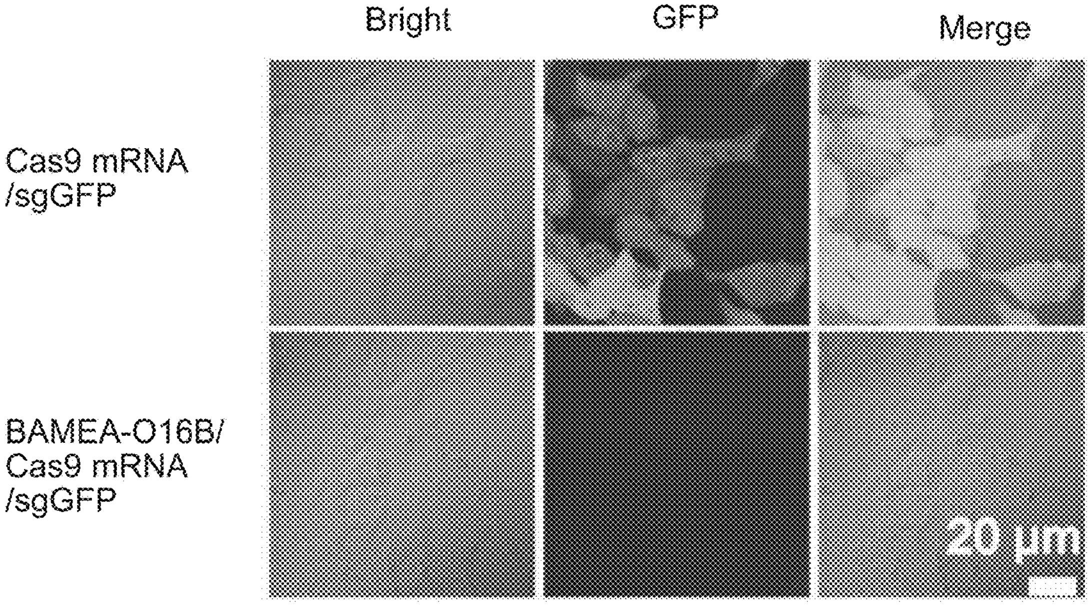
FIG. 4A are CLSM images of HEK-GFP cells treated with Cas9 mRNA/sgGFP alone or BAMEA/Cas9 mRNA/sgGFP nanoparticles. Scale bar: 20 μm.
Figure 4B:
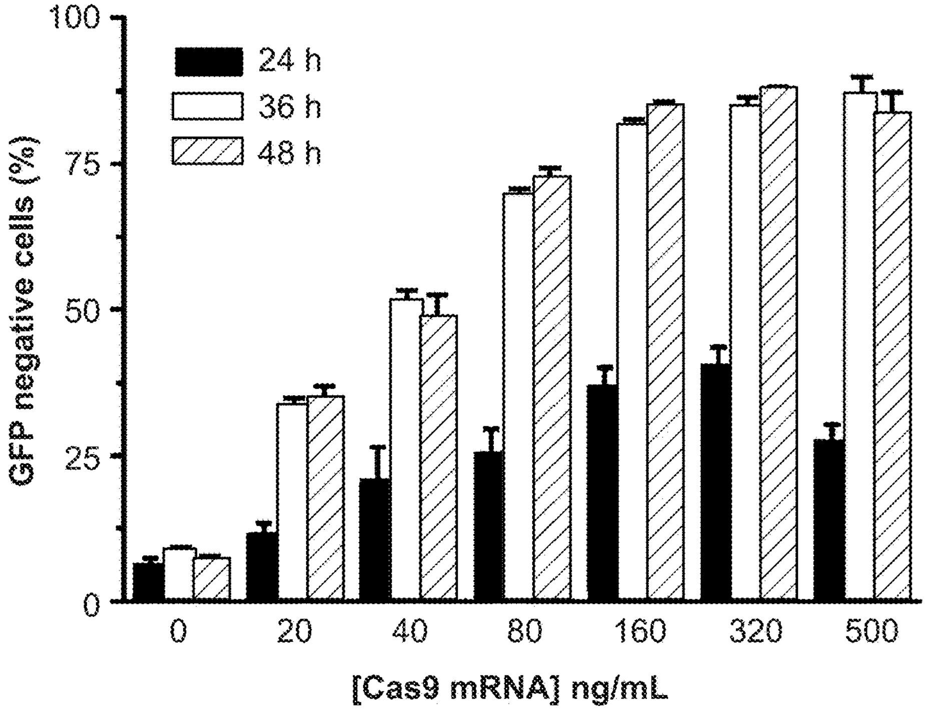
FIG. 4B is a bar graph depicting the delivery of BAMEA/Cas9 mRNA/sgGFP nanoparticles for fast and efficient genome editing. HEK-GFP cells were treated with different dose of Cas9 mRNA and sgGFP (13 nM), the GFP expression was quantified at different time points after delivery.
Figure 4C:
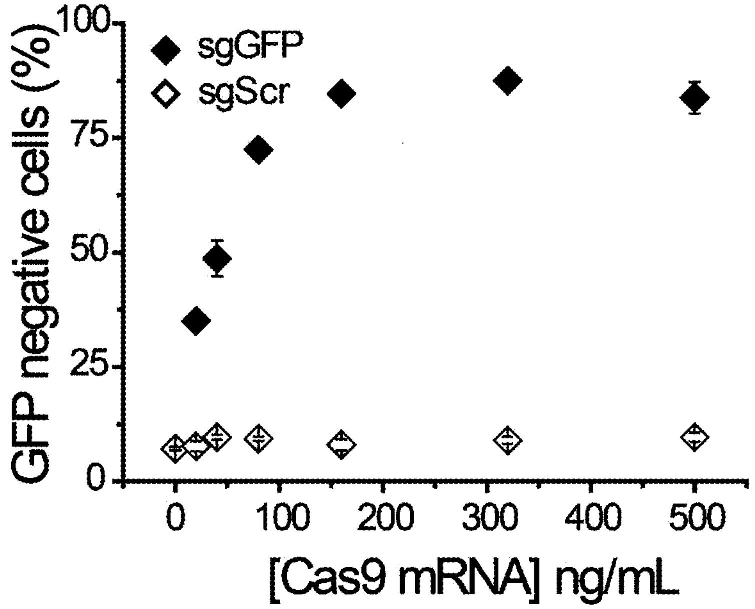
FIG. 4C is a plot depicting the sgRNA sequence specific genome editing and GFP knock out using BAMEA/Cas9 mRNA/sgGFP nanoparticles. GFP-HEK cells were treated with BAMEA/Cas9 mRNA/sgGFP or BAMEA/Cas9 mRNA/scramble sgRNA nanoparticles, and the GFP knock out efficiency was determined 48 h post mRNA delivery.

CLSM imaging indicated that BAMEA-O16B/Cas9 mRNA/sgGFP nanoparticle treatment resulted in a complete loss of the GFP fluorescence of HEK-GFP cells, while free Cas9 mRNA and sgRNA treatment did not shown similar GFP knock out effect (FIG. 4A). Quantitative analysis of GFP expression of HEK-GFP cells showed that with the concentration of Cas9 mRNA delivered to cells increased from 20 ng/mL to 160 ng/mL, the GFP knock out efficiency increased from 35% to higher than 90% accordingly (FIG. 4B). Meanwhile, when the sgGFP was replaced with a scramble sgRNA, an effective genome editing and cellular GFP loss was not observed (FIG. 4C). It is noticeable that BAMEA-O16B/Cas9 mRNA/sgRNA treatment knocked out GFP expression at protein level very fast (FIG. 4B). 40% GFP knock out was observed as early as 24 h post Cas9 mRNA delivery, and this ratio was increased up to 90% 36 h post Cas9 mRNA delivery, though a further extension of delivery time did not increase the genome edit efficiency.

Figure 5A:
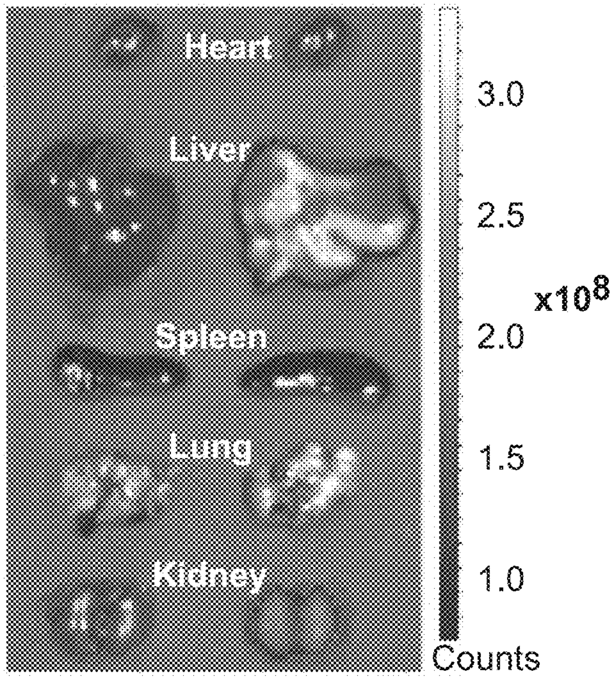
FIG. 5A is a bioluminescence image of the tissues of mice injected with BAMEA-O16B/Cas9 mRNA/Cy3-RNA nanoparticles (right) or Cas9 mRNA/Cy3-RNA (free).
Figure 5B:
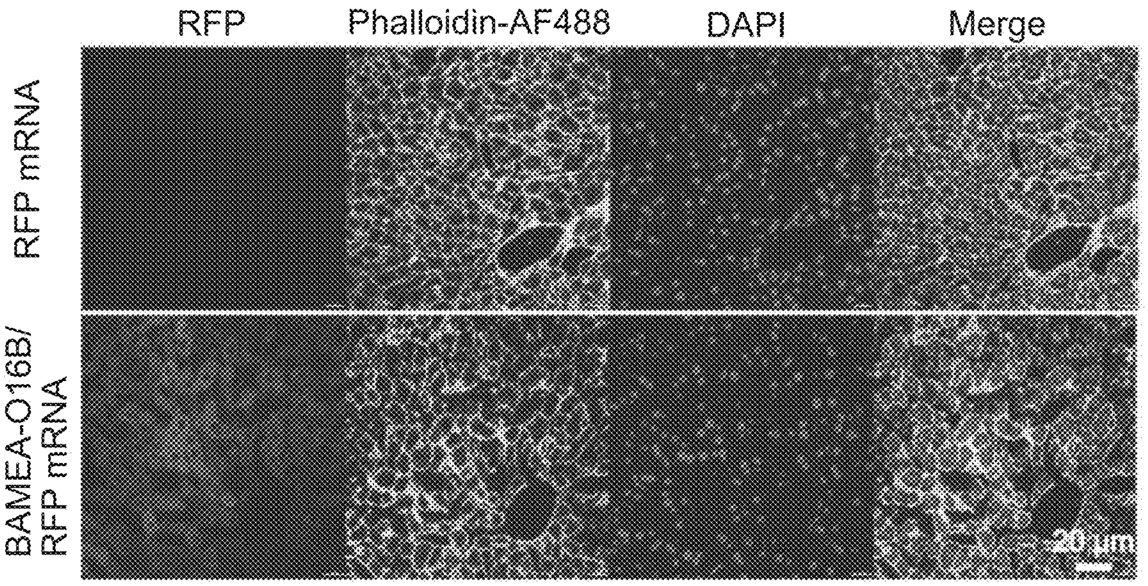
FIG. 5B are fluorescent images of mouse liver injected with BAMEA-O16B/RFP mRNA nanoparticles indicated the efficient delivery of mRNA into hepatocytes; Scale bar: 20 μm.
Figure 5C:
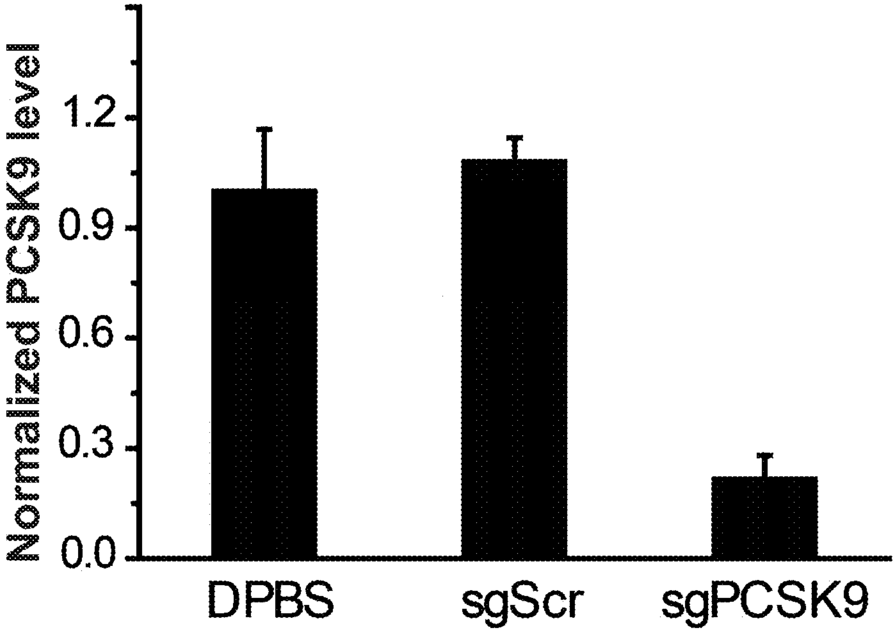
FIG. 5C is a bar graph depicting BAMEA-O16B/Cas9 mRNA/sgPCSK9 nanoparticles treatment effectively decreased mouse serum PCSK9. The serum PCSK9 level of Cas9 mRNA nanoparticle treatment was normalized to that injected with DPBS control.

Example 3. BAMEA-O16B Mediated Cas9 mRNA Delivery is Able to Regulate Endogenous Gene Expression FIGS. 5A-5C are graphs and images depicting Cas9 mRNA/sgRNA delivery and genome editing in vivo.

Figure 4D:
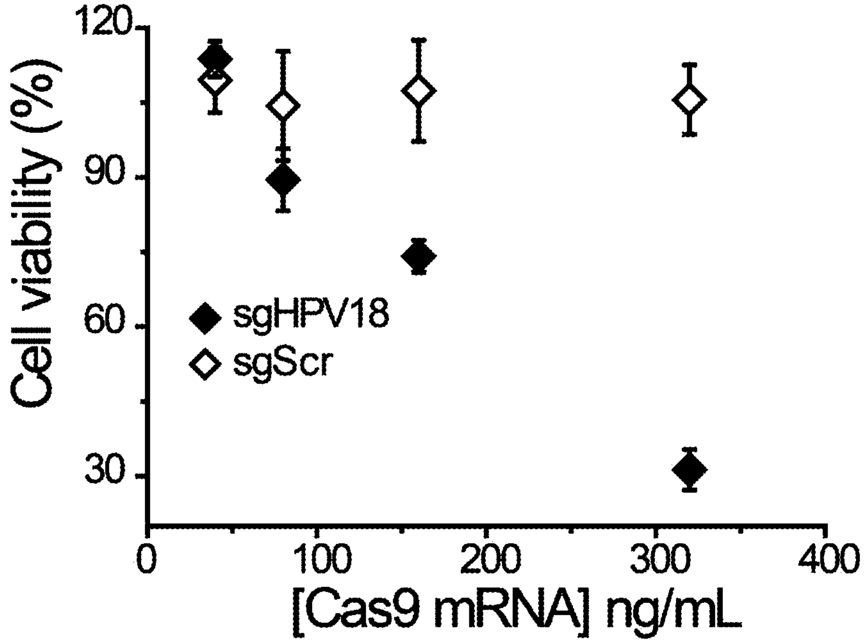
FIG. 4D is a plot depicting the delivery of BAMEA/Cas9 mRNA/sgHPV18 nanoparticles efficiently and selectively prohibited HeLa cell growth.

Further, it is shown that BAMEA-O16B mediated Cas9 mRNA delivery is able to regulate endogenous gene expression, and therefore of great potential for developing new gene therapy. Human papillomavirus type 18 (HPV18), an essential gene that promotes human cervical cancer progression was selected as a target to study. SgRNA that targets HPV18 was delivered into HeLa cells along with Cas9 mRNA using BAMEA-O16B, the viability of HeLa cells followed the treatment was measured and compared to that with scramble sgRNA and Cas9 mRNA treatment. As shown in FIG. 4D, BAMEA-O16B/Cas9 mRNA/sgHPV18 treatment significantly prohibited HeLa growth compared to that of a scramble sgRNA and Cas9 mRNA delivery (FIG. 4D). For example, the delivery of 320 ng/mL Cas9 mRNA and 26 nM sgHPV18 reduced HeLa cell viability down to 30%, while the replacement of sgHPV18 with a scramble sgRNA did not show similar effect on prohibiting HeLa cell growth.

To further demonstrate the potential of BAMEA-O16B nanoparticle for in vivo mRNA delivery and CRISPR/Cas9 genome editing, proprotein convertase subtilisin/kexin type 9 (PCSK9), an enzyme secreted from hepatocytes and involved cholesterol homeostasis was selected as a target to study. PCSK9 plays an important role in lipid metabolism by modulating the density of low-density lipoprotein cholesterol receptors (LDL-R) in liver, genetic studies reveal that the loss of PCSK9 is associated with a reduced risk of cardiovascular disease.

Figure 11:
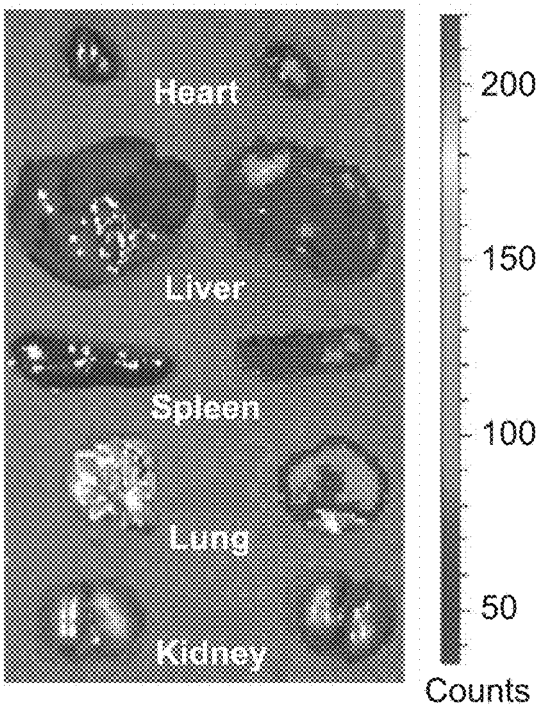
FIG. 11 is bioluminescence imaging of the tissues of mice injected with BAMEA-O16B/Luci mRNA nanoparticles (right) or free mRNA (left).

The biodistribution of BAMEA-O16B nanoparticle for in vivo mRNA delivery was first studied. To this end, BAMEA-O16B/Luciferase mRNA nanoparticle or fluorescently labeled BAMEA-O16B/Cas9 mRNA/Cy3-RNA nanoparticles were formulated and intravenously injected to mice via tail vein at an mRNA dosage of 0.6 mg/kg or 0.8 mg/kg sgRNA, followed by bioluminescence or fluorescence imaging of tissue organs to study the biodistribution of the nanoparticles. As shown in FIG. 11 and FIG. 5A, the injection of BAMEA-O16B/Luciferase mRNA nanoparticle resulted in effective expression of luciferase in mouse liver, while BAMEA-O16B/Cas9 mRNA/Cy3-RNA nanoparticle administration showed effective accumulation of fluorescent signal in mouse liver. A detailed cellular localization study by delivering BAMEA-O16B/RFP mRNA nanoparticles revealed that the BAMEA-O16B/RFP mRNA nanoparticle was mostly accumulated in hepatocytes (FIG. 5B), which could be used for PCSK9 genome editing in hepatocytes, as to be discussed below.

Figure 12:
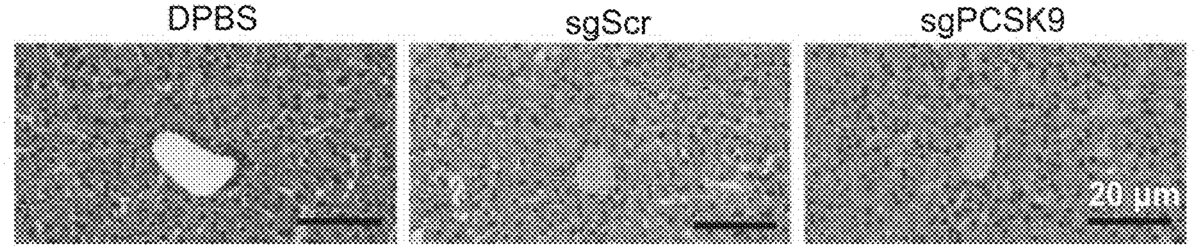
FIG. 12 depicts the histological analysis of the liver at two-day post-injection by haematoxylin and eosin stain. Scale bars, 20 μm.
Figure 13:
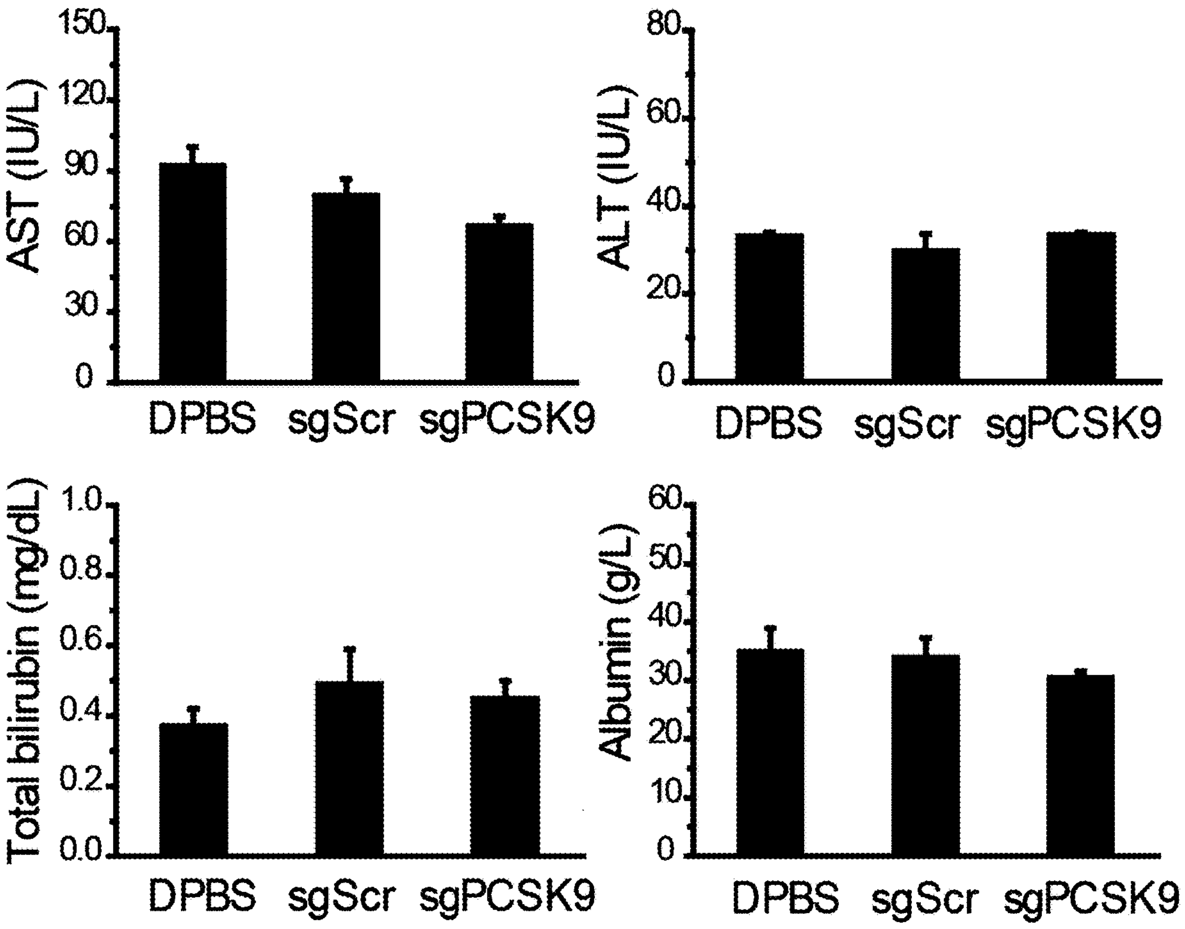
FIG. 13 are bar graphs depicting the liver function tests in BAMEA-O16B/Cas9 mRNA/sgPCSK9 injected mice.
Figure 14:
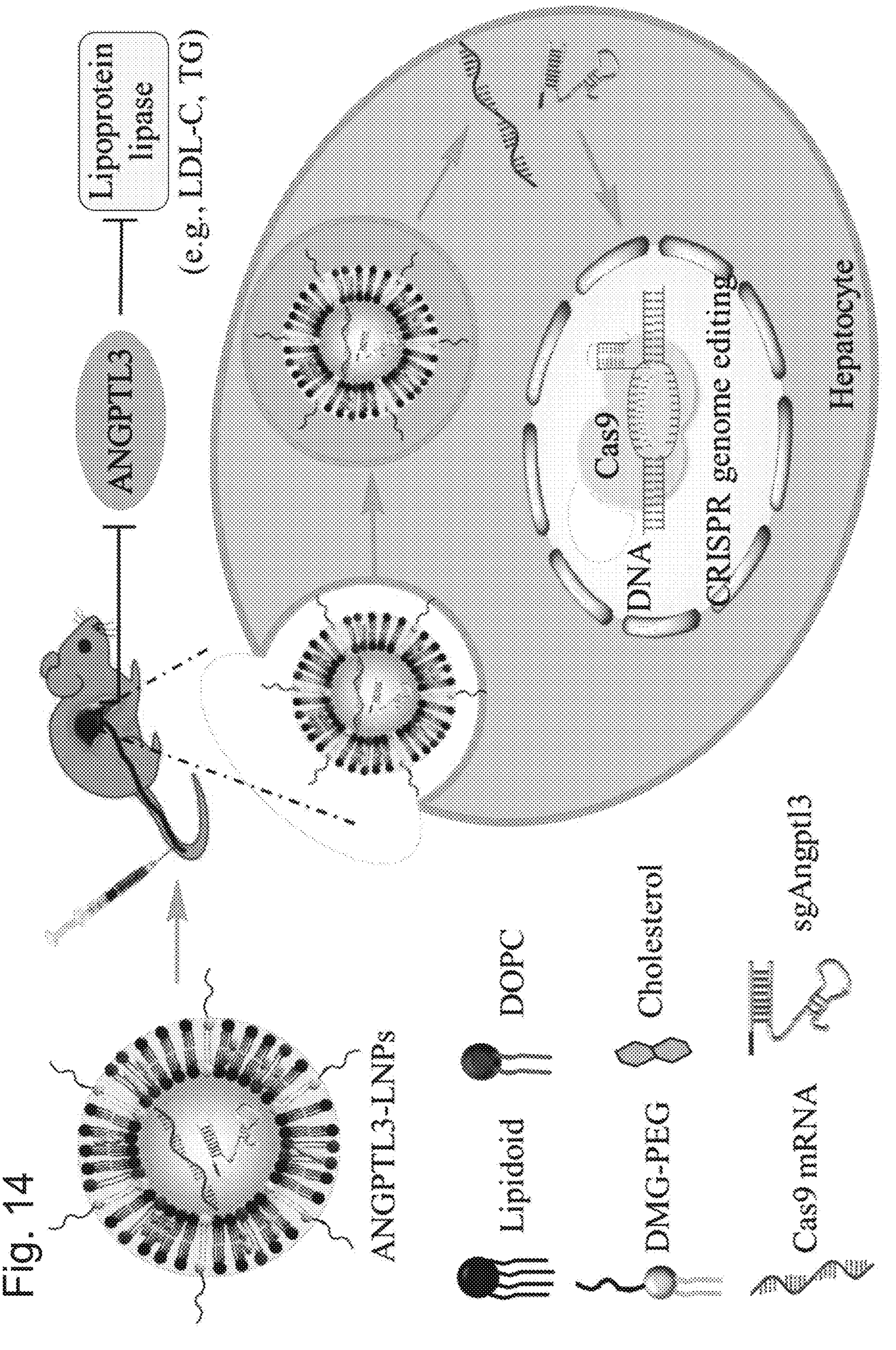
FIG. 14 is a schematic illustration of non-viral lipid nanoparticles (LNPs)-mediated in vivo CRISPR/Cas9-based genome editing to induce loss-of-function mutations in ANGPTL3 to lower blood lipid levels. The Cas9 mRNA and ANGPTL3-specific single guide RNA (sgAngptl3) are encapsulated in the LNPs and delivered to the liver hepatocytes to perform genome editing at the ANGPTL3 target locus, and subsequently lowering low density lipoprotein cholesterol (LDL-C) and triglyceride (TG) levels.

The potential and efficacy of BAMEA-O16B nanoparticle for in vivo genome editing was studied by injecting BAMEA-O16B/Cas9 mRNA/sgPCSK9 nanoparticles into C57BL/6 mice, followed by serum PCSK9 level quantification to evaluate the in vivo genome editing efficacy. As shown in FIG. 5C, the intravenous injection of BAMEA-O16B/Cas9 mRNA/sgPCSK9 nanoparticle reduced mouse serum PCSK9 down to 20% of that with DPBS injection or BAMEA-O16B/Cas9 mRNA/scramble sgRNA nanoparticle injections (FIG. 5C). Meanwhile, histological examination of the mouse liver after BAMEA-O16B/Cas9 mRNA/sgRNA nanoparticle treatment using haematoxylin and eosin (H&E) staining did not show signs of inflammation (FIG. 12). Moreover, the nanoparticle injections did not induce obvious hepatocellular injury, as revealed by the minimal change of serum aspartate transaminase (AST), alanine aminotransferase (ALT), and total bilirubin of mice with all injections (FIG. 13). Altogether, the above results clearly demonstrated the high efficacy and biocompatibility of BAMEA-O16B nanoparticle for in vivo genome editing.

II. Lipid Nanoparticles Mediated Delivery of CRISPR/Cas9 mRNA for In Vivo Genome Editing of ANGPTL3

Materials and Methods

LNPs Formulation

The lipidoids were synthesized as per our previous reports. LNPs were prepared using a NanoAssemblr microfluidic system (Precision Nanosystems). Briefly, lipidoids, cholesterol (Sigma), phospholipids (DSPC, DOPE, and DOPC, Avanti Polar Lipids), and DMG-PEG (Avanti Polar Lipids) were dissolved in 100% ethanol at molar ratios of 50/38.5/10/1.5 at a final lipidoids concentration of 10 mg/mL. Cas9 mRNA and gRNA (either sgANGPTL3 or sgLoxP) were mixed at the appropriate weight ratio in sodium acetate buffer (25 mM, pH 5.2). The mRNA solution and the lipid solution were each injected into the NanoAssemblr microfluidic device at a ratio of 3:1, and the device resulted in the rapid mixing of the two components and thus the self-assembly of LNPs. Formulations were further dialyzed against PBS (10 mM, pH 7.4) in dialysis cassettes overnight at 4° C. The particle size of formulations was measured by dynamic light scattering (DLS) using a ZetaPALS DLS machine (Brookhaven Instruments). RNA encapsulation efficiency was characterized by Ribogreen assay.

In Vivo LNPs Delivery

All procedures for animal experiment were approved by the Tufts University Institutional Animal Care and Use Committee (IACUC) and performed in accordance with the National Institutes of Health (NIH) guidelines for the care and use of experimental animals. All the animals were ordered from Charles River. Female Balb/c mice (6-8 weeks) were used for in vivo firefly luciferase mRNA (fLuc mRNA, TriLink Biotechnologies) encapsulated LNPs screening and formulations optimization. Briefly, fLuc mRNA LNPs were intravenously injected into the mice at a dose of 0.5 mg/kg mRNA. At predetermined time point, mice were injected with 100 μL of D-Luciferin potassium salt (Goldbio) solution (15 mg/mL in PBS), anesthetized under isoflurane anesthesia, and measured by IVIS imaging system (Caliper Life Sciences).

In Vivo Cas9 mRNA/sgLoxP Delivery

Cas9 mRNA (TriLink Biotechnologies) and LoxP-targeted single guide RNA (sgLoxP, sequence: 5'-AAGTAAAACCTCTACAAATG (SEQ ID NO: 5), Synthego) were coloaded into 306-O12B LNPs and intravenously injected into female Ai14 mouse at a dose of 1.65 mg/kg total RNA. At day 7 post-injection, mouse organs were collected and imaged by IVIS to detect the tdTomato expression. The liver tissue was further sectioned.

Immunostaining

Tissue samples were embedded with OCT, frozen completely in liquid nitrogen, and stored at −80° C. until ready for sectioning. The frozen tissue block was sectioned into a desired thickness (10 μm) using the cryotome and placed onto glass slides suitable for immunofluorescence staining. The tissue sections were fixed with pre-cooled acetone (−20° C.) for 10 min, and then washed twice with PBS, 5 min each. The fixed tissue sections were incubated in 10% BSA blocking buffer at room temperature (r.t.) for 1 h, and then washed with PBS. A hepatocyte specific primary antibody (1:100 diluted in 1% BSA buffer, anti-hepatocyte specific antigen (HepParl), Novus) was applied to the sections on the slides and incubated in a humidified chamber at 4° C. overnight. The slides were rinsed with PBS for 2 changes, 5 min each, and then stained with eFlour660 conjugated F(ab')2-Goat anti-mouse secondary antibody (1:50, Invitrogen) s and incubated in a humidified chamber protected from light at room temperature for 1 h, and then washed 3 times with PBS. Fluorescent mounting medium containing DAPI (Sigma) was used to coverslip the slides. Sections were analyzed using a Leica SP8 confocal microscope.

In Vivo Genome Editing of ANGPTL3

Guide RNA sequence targeting ANGPTL3 gene was designed using the Benchling software. Female wild-type C57BL/6 mice were intravenously dosed with Cas9 mRNA and ANGPTL3-targeted single guide RNA (sgAngptl3, sequence: 5'-AGCCCTTCAACACAAGGTCA (SEQ ID NO: 6), Synthego) co-loaded 306-O12B LNPs at a dose of 1.0, 2.0, and 3.0 mg/kg in total RNA. PBS administrated mice were treated as negative control. At day 7 post-injection, mice were sacrificed, blood was collected for circulating ANGPTL3 protein and blood lipids quantitation by ELISA, and liver tissue was collected from the median and left lateral lobe for DNA extraction and next generation sequence (NGS) analysis. In addition, to evaluate the in vivo toxicity and immune response, blood was collected and proceeded to serum from mice 2 days after the injection. Aspartate aminotransferase (AST) and alanine aminotransferase (ALT), and tumor necrosis factor alpha (TNF-alpha) were measured using assay kits for AST (G-Biosciences), ALT (G-Biosciences), and TNF-alpha (R&D Systems) per manufacturer's protocols.

NGS Sequencing Analysis

DNA was extracted from the median and left lateral lobe of the liver using a commercial extraction kit (Qiagen DNEasy Blood & Tissue). PCR primers were designed to amplify the region surrounding the target site in the Angpt13 gene, or the regions surrounding the predicted off-target sites (Table Si). Off-target sites were predicted using the Cas Off Finder software (rgenome.net/cas-offinder/). PCR amplicons were prepared for sequencing on an Illumina MiSeq (Tufts Genomics Core Facility). Sequencing data was analyzed using the OutKnocker 2 software (outknocker.org/outknocker2.htm).

Serum ANGPTL3 Protein, Low Density Lipoprotein Cholesterol (LDL-C), and Triglyceride (TG) Analysis Mouse blood was collected without using an anticoagulant and allow to clot for 2 h at r.t., and centrifuged at 2000×g for 15-20 min at r.t. to collect mouse serum. Serum levels of ANGPTL3 protein, LDL-C, and TG were determined using a Mouse Angiopoietin-like 3 Quantikine ELISA kit (R&D systems), Mouse LDL-Cholesterol kit (Crystal Chem), and Triglyceride Colorimetric Assay kit (Cayman Chemical) as per manufacturer's protocols, respectively.

T7E1 Cleavage Assay

The genomic regions flanking the on-target sites were amplified using extracted genomic DNA template, Platinum SuperFi Green DNA polymerase (Invitrogen), and specific primers (Table 3).

TABLE 3

PCR primers used for these experiments

| ID | SEQ ID NO: | Forward | SEQ ID NO: | Reverse |
|---|---|---|---|---|
| Angpt13 NGS | 7 | CTCCAAAGCCCTGACCTTGT | 18 | TCTGCACCTTCAGAGCCAAA |
| Angpt13 T7E1 | 8 | TTCTGCACCTTCAGAGCCAA | 19 | GCAAAGCAAACCCTGAACTGA |
| Off1 | 9 | ACCTTGGTTAGGATGCCTGC | 20 | TTGCATTCCTGTCAGAGTGAT |
| Off2 | 10 | ACATAGCCATCCCCCAACAA | 21 | GCTGCAACTTGGTGCTACCT |
| Off3 | 11 | TGACATGACTCATTGCCACCA | 22 | GTGAACCATATCTTAATAGCACCAT |
| Off4 | 12 | TCTAAATGCCAGGGTTCTGACT | 23 | CATGCCATGTGGGGTGATACAA |
| Off5 | 13 | TACCCAGCCATATTGTGCAG | 24 | AGAAGACCAGATAGAAGTCAGGATG |
| Off6 | 14 | CGGATGTTTGCATGAGGGGA | 25 | GGTTAGCTGCTGGACACTGA |
| Off7 | 15 | GGTGTCCACTTGTTAAATGTCA | 26 | ACAACAACATGGAAAACTCTA |
| Off8 | 16 | GCCAGCCACAGTTTTCATCG | 27 | GGGAGTCACAGTCATGGGTC |
| Off9 | 17 | GCAGTCATCAGACAGGAGGG | 28 | GCAGCTCTCCAATCCAGACA |

The following cycles were run: 30 s at 98° C., followed by 33 cycles of 10 s at 98° C., 15 s at 65° C., and 30 s at 72° C., followed 10 min at 72° C. The PCR products were purified using the GeneJET PCR Purification Kit (Thermo Scientific). 400 ng of purified PCR products were hybridized in NEBuffer 2 (New England Biolabs) by heating to 95° C.

for 5 min, followed by a 2° C./second ramp down to 85° C. and a 0.1° C./second ramp down to 25° C. on a Applied-Biosystems PCR system (Thermo Fisher Scientific). The annealed samples were digested by T7 Endonuclease I (New England Biolabs) at 37° C. for 15 min, followed by incubating at 65° C. for 5 min to stop the reaction. The products were further purified and run on a 4-20% Novex TBE gel (Invitrogen).

Statistical Analysis

Data were expressed as mean±SD. All data were analyzed using Graphpad Prism software. *p<0.05 was considered significant, and p<0.01, *p<0.001 were considered highly significant.

Example 4. In Vivo Screening of Lipid Nanoparticles for mRNA Delivery

Figure 15A:
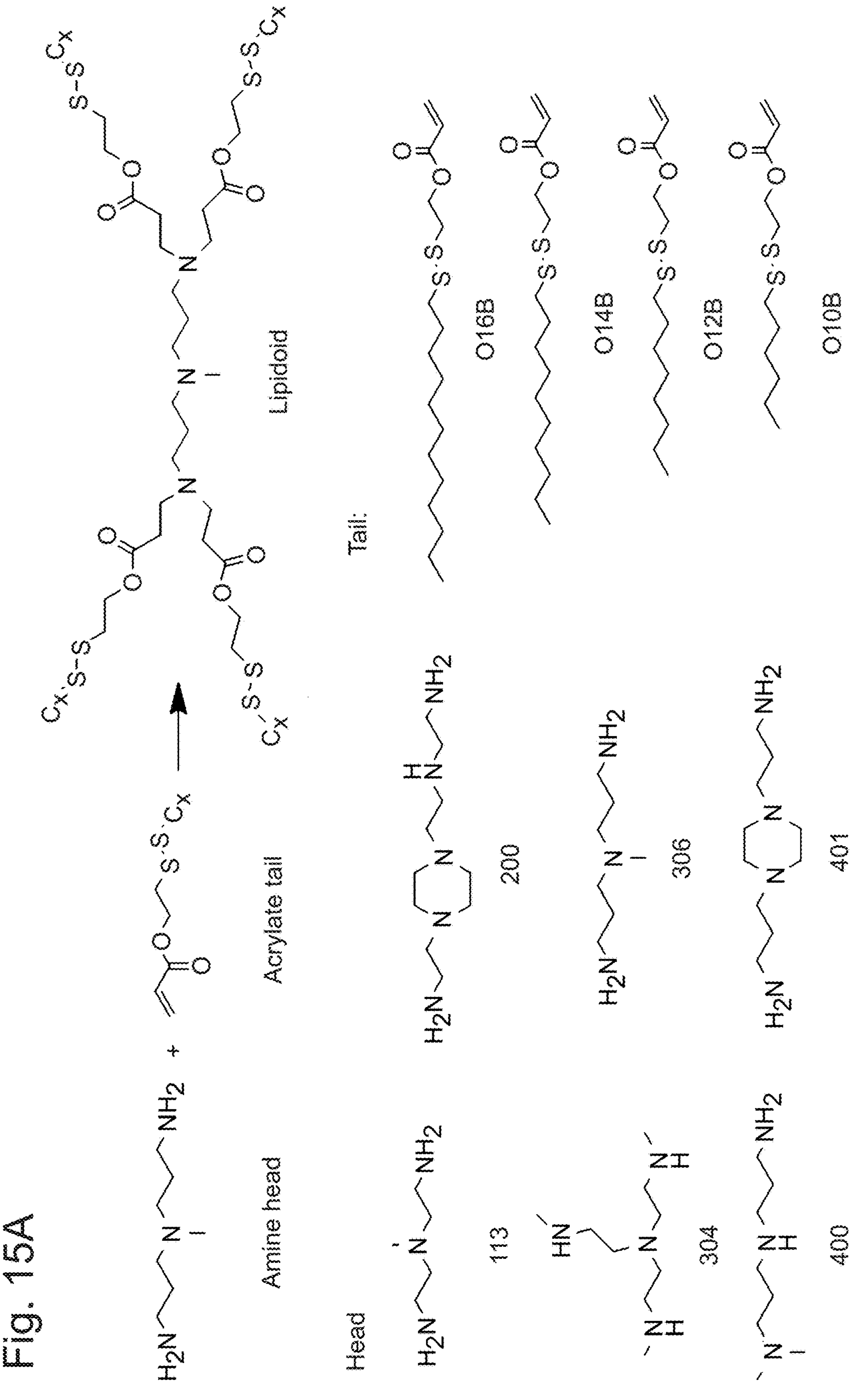
FIG. 15A are the chemical structures of tail-branched bioreducible lipidoids.
Figure 15B:
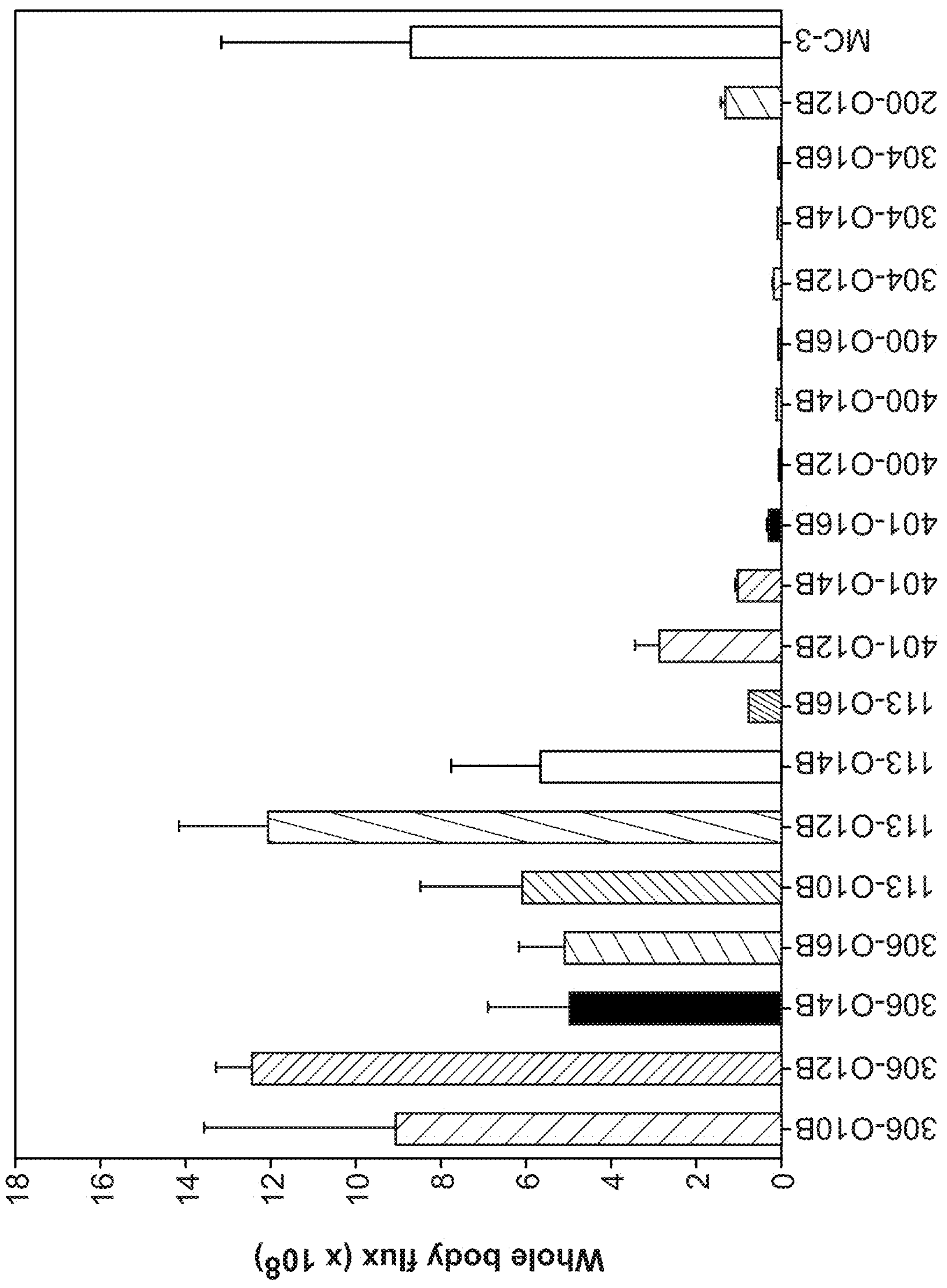
FIG. 15B is a bar graph depicting the whole body luciferase bioluminescence intensity of bioreducible LNPs versus MC3 LNPs measured in Balb/c mice (n=3) at 6 h post-administration at a firefly luciferase (fLuc) mRNA dose of 0.5 mg/kg. Formulation: lipid/cholesterol/DSPC/DMG-PEG=50/38.5/10/1.5 (molar ratio), lipid/mRNA=12.5/1 (weight ratio).
Figure 15C:
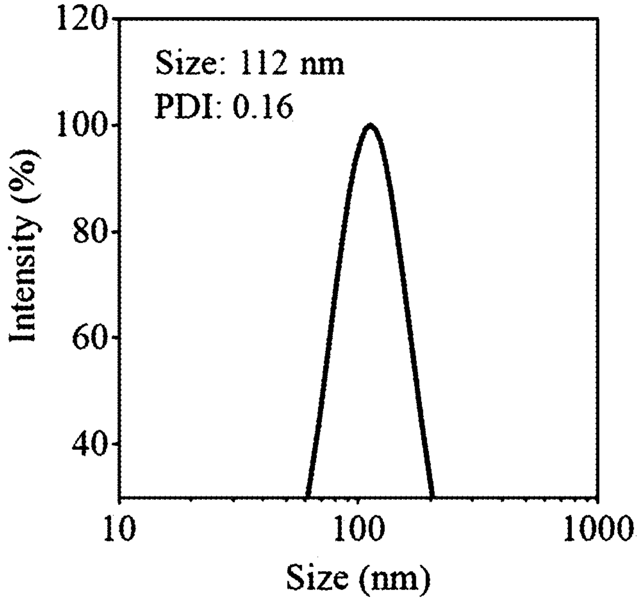
FIG. 15C is a dynamic light scattering graph of size and distribution of 306-O12B LNPs formulated with fLuc mRNA.

FIGS. 15A-15C depict syntheses of lipidoid nanoparticles.

Figure 20A:
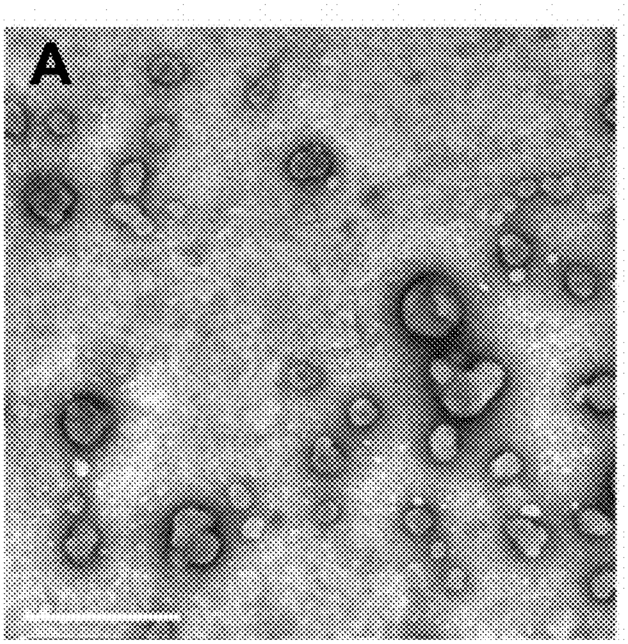
FIG. 20A is a representative TEM image of 306-O12B LNPs before formulated with fLuc mRNA. (Scale bar: 500 nm)
Figure 20B:
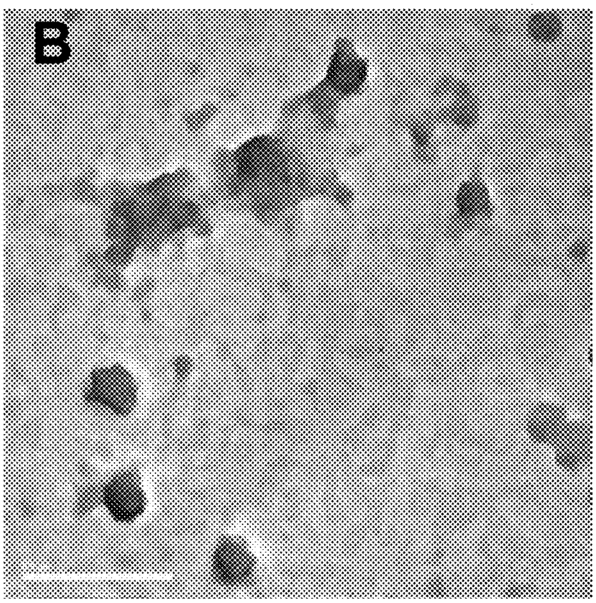
FIG. 20B is a representative TEM image of 306-O12B LNPs after formulated with fLuc mRNA. (Scale bar: 500 nm)
Figure 21:
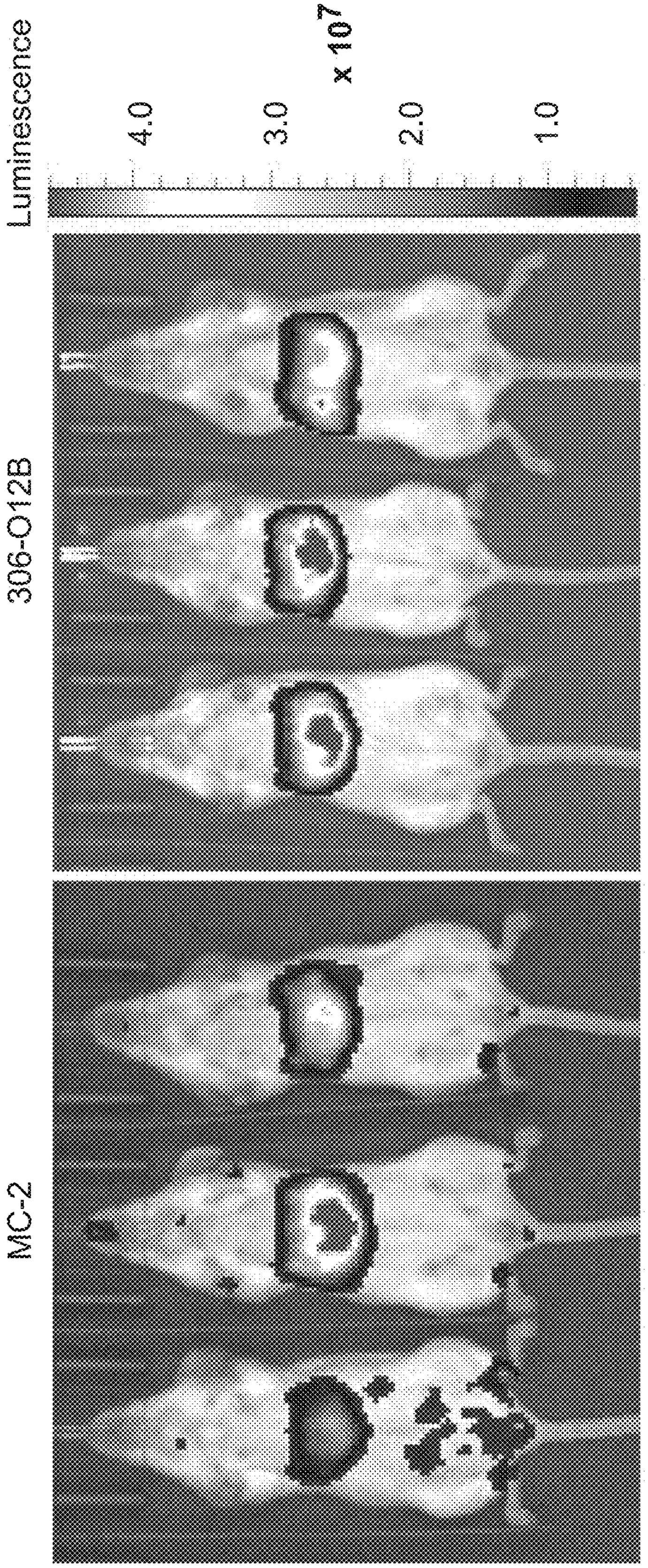
FIG. 21 is an in vivo imaging of mice injected with fLuc mRNA loaded 306-O12B LNPs and MC-3 LNPs. Images were taken by IVIS imaging system at 6 h post-injection.
Figure 22:
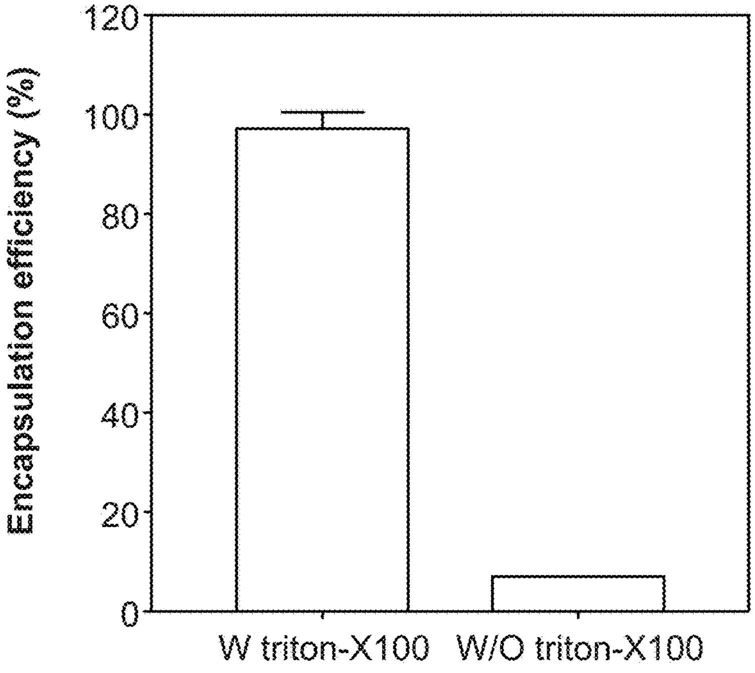
FIG. 22 is a bar graph depicting the encapsulation efficiency of 306-O12B LNPs to fLuc mRNA.

The tail-branched bioreducible lipidoids were prepared via a combinatory solvent free Michael-Addition reaction between disulfide bond-incorporated acrylate lipid tails and amine-containing heads. (FIG. 15A). The in vivo mRNA delivery efficacy of these lipids was first evaluated by encapsulating firefly luciferase mRNA (fLuc mRNA) into LNPs and delivering these LNPs intravenously to female wild-type Balb/c mice. These LNPs were formulated with our synthetic ionizable lipids, along with the excipient compounds cholesterol, DSPC, and DMG-PEG. Representative transmission electron microscopy images of blank (unloaded) and fLuc mRNA-loaded LNPs were shown in FIG. 20A and FIG. 20B. The gold standard MC-3 LNPs was included as a positive control. 6 hours after mRNA delivery, mice were injected intraperitoneally with luciferin substrate, and whole-body fLuc activity was measured using an IVIS in vivo imaging system (PerkinElmer). As shown in FIG. 15B, mRNA delivery with 306-O12B, 113-O12B, and 306-O10B LNPs resulted in comparable or even higher luciferase bioluminescence intensity as compared with MC-3 LNPs delivery. In vivo images of mouse clearly showed that the luciferase protein was mainly expressed in the liver (FIG. 21). 306-O12B was used as the representative lipid for further experiments. The fLuc mRNA could be efficiently encapsulated into the 306-O12B LNPs with an encapsulation efficiency of ~98% (FIG. 22). Following the encapsulation of fLuc mRNA, 306-O12B LNPs had an average diameter of 112 nm (FIG. 15C).

Example 5. Optimization of the Formulation of 306-O12B LNPs

FIGS. 16A-16F depict the optimization of fLuc mRNA 306-O12B LNPs formulations.

In order to further increase the luciferase expression in vivo, we optimized a variety of formulation parameters used for the assembly of these LNPs, including the excipient phospholipid identity, the molar composition ratios of the four-components of the LNPs formulation, and the lipid/mRNA weight ratio of fLuc mRNA encapsulated 306-O12B LNPs.

Figure 16A:
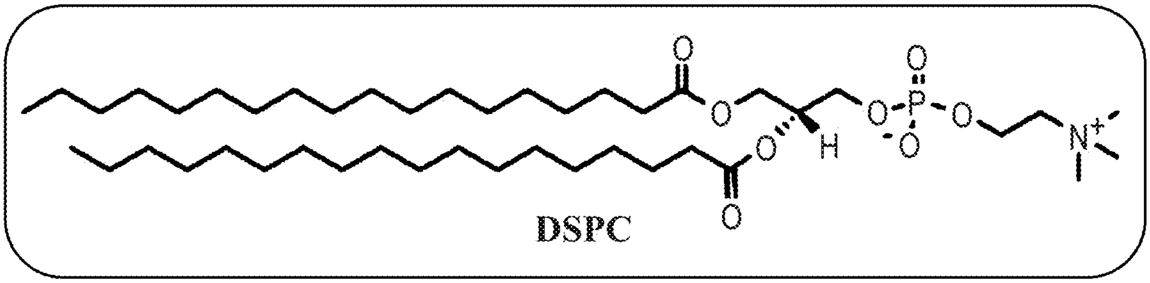
FIG. 16A are chemical structures of three different phospholipids.
Figure 16A:
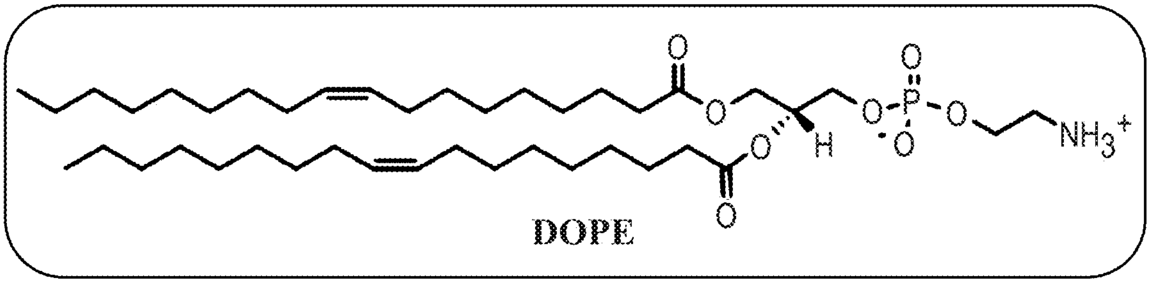
Figure 16A:
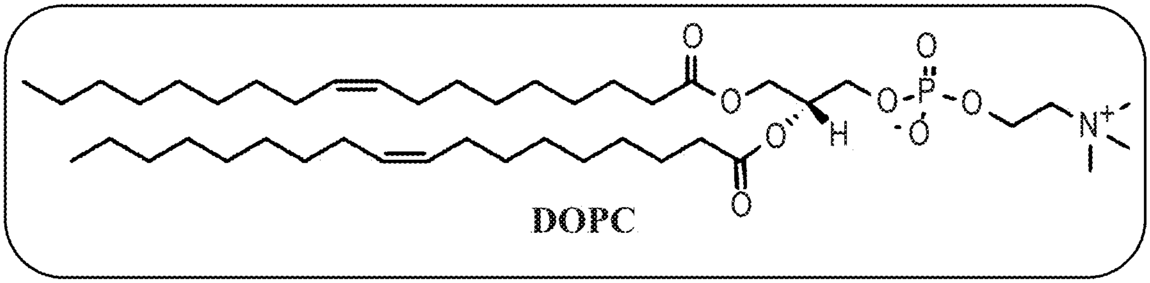
Figure 16B:
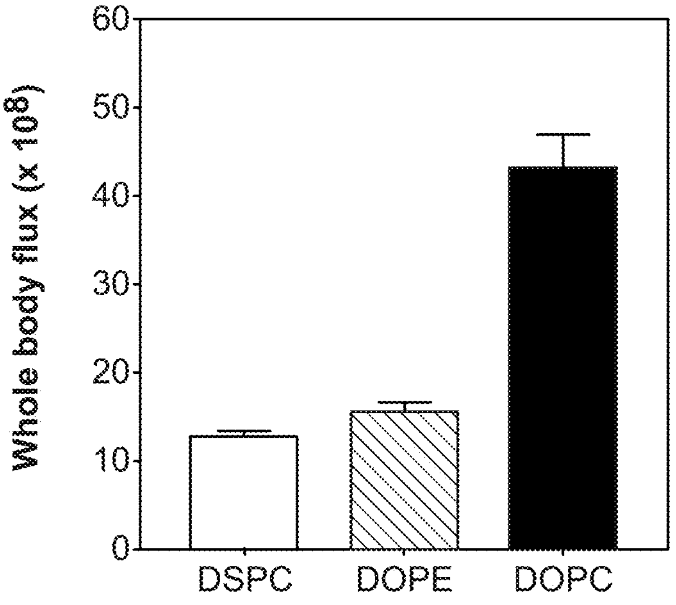
FIG. 16B is a bar graph depicting the efficacy of fLuc mRNA LNPs formulated with Cholesterol, DMG-PEG, and different phospholipid, DSPC or DOPE or DOPC.
Figure 16C:
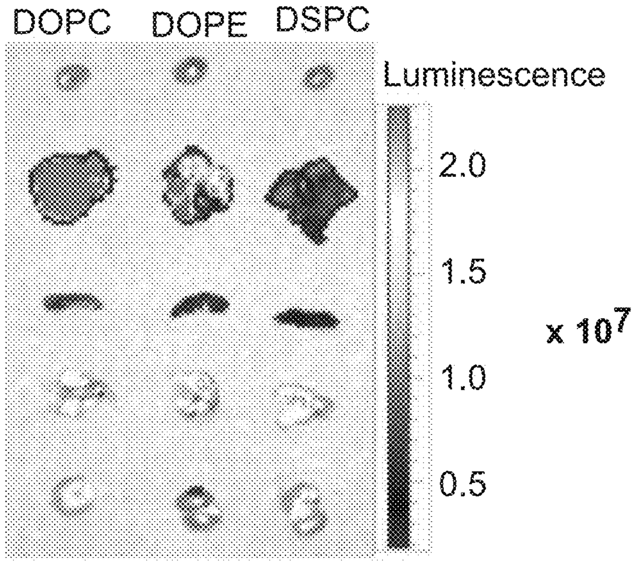
FIG. 16C is an image depicting biodistribution of fLuc mRNA LNPs formulated with Cholesterol, DMG-PEG, and different phospholipid, DSPC or DOPE or DOPC.

First, two additional phospholipids DOPE and DOPC (FIG. 16A) which have similar structure, but differing head groups and tail saturation comparing to the original DSPC phospholipid, were selected to evaluate the effect of phospholipid excipient on the efficacy of luciferase expression in vivo. DOPC and DOPE each contain one degree of unsaturation in the carbon tail, while DSPC is fully saturated. Furthermore, DSPC and DOPE each contain a quaternary amine headgroup, while DOPE contains a primary amine headgroup. Each of these features has been reported to influence LNP delivery efficiency in the literature. It has been reported that quaternized amine head groups show a stronger proton sponge effect than primary amine head, which can facilitate the endosomal escape of the cargo mRNA into cytoplasm, thus increasing translation of the mRNA to protein. Furthermore, the degree of saturation of the lipid tail has been shown to influence membrane fluidity, which may also influence endosomal escape. Unsaturated lipid tails may result in higher membrane fluidity, which may also help to improve endosomal escape via destabilization of the endosomal membrane upon fusion of the LNP with the membrane. Taken together, we would hypothesize that LNPs formed with DOPC, containing a quaternary amine and unsaturated tail, would show the most efficient fLuc delivery. As shown in FIG. 16B and FIG. 16C, fLuc mRNA LNPs formulated with DOPC indeed resulted in significantly higher luciferase expression in the liver than that of formulations with DOPE and the original DSPC phospholipid. fLuc mRNA delivered with DOPC-containing LNPs resulted in approximately 4-fold higher luminescence signal compared with the original DSPC-containing LNPs.

Figure 16D:
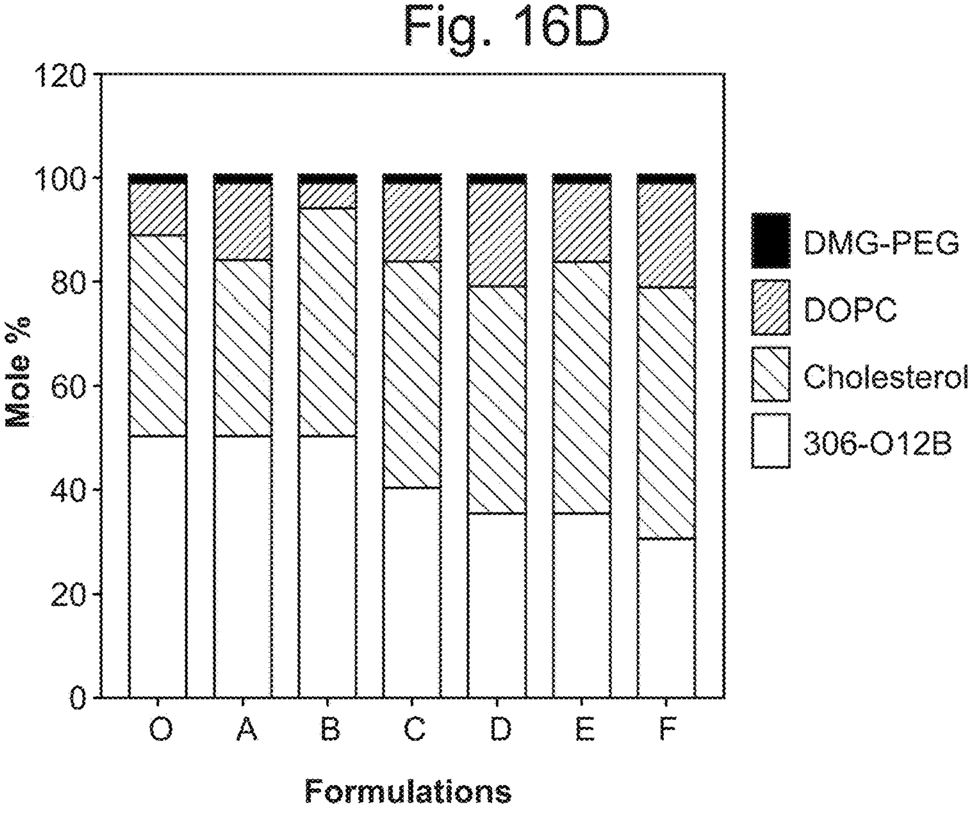
FIG. 16D is a graph depicting the formulation parameters of LNPs formulated with cholesterol, DOPC, DMG-PEG at 7 different mole ratios.
Figure 16E:
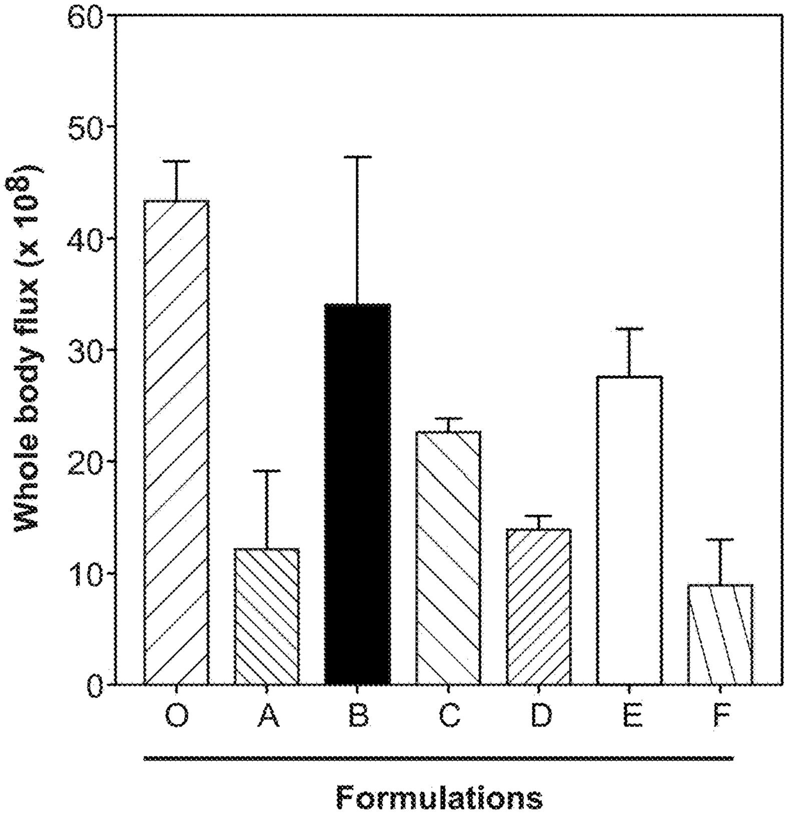
FIG. 16E is a bar graph depicting the whole body luciferase bioluminescence intensity of different formulations in Balb/c mice at 6 h post-injection at a fLuc mRNA dose of 0.5 mg/kg.
Figure 16F:
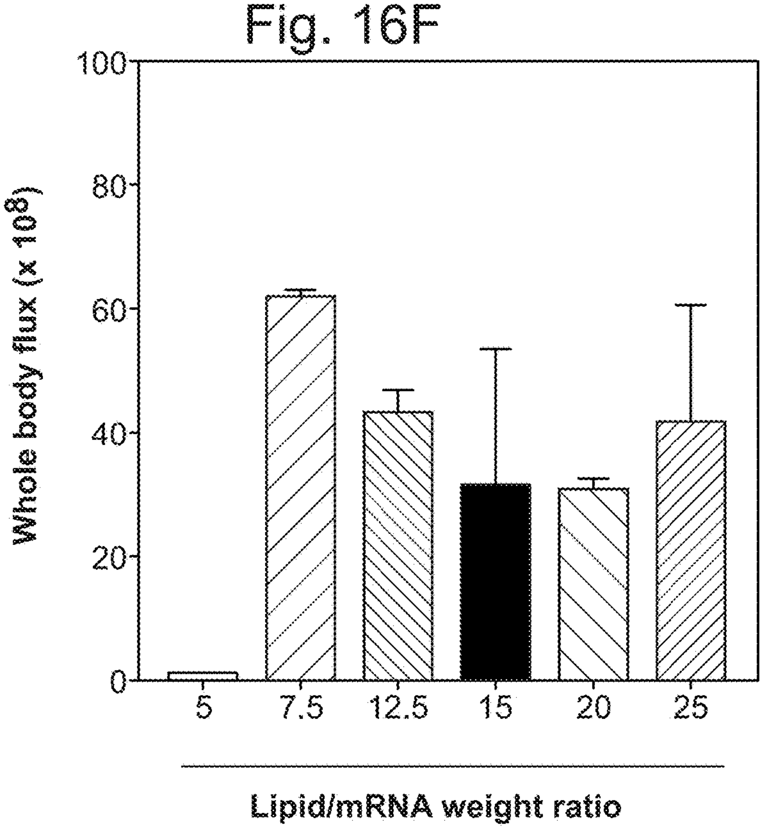
FIG. 16F is a bar graph depicting whole body luciferase bioluminescence intensity 6 h post-injection of 0.5 mg/kg fLuc mRNA for LNPs formulated with cholesterol, DOPC, DMG-PEG at a molar ratio of 50/38.5/10/1.5 with differing 306-O12B/mRNA weight ratios. (n=3)

In initial screenings, the active lipid and excipient components were formulated at a molar ratio of [Lipid:Cholesterol:DSPC:DMG-PEG] of [50:38.5:10:1.5]. After identifying the optimal phospholipid as DOPC, and adjusting the formulation accordingly, LNPs formulated at a variety of molar ratios was tested to identify the optimal parameters (FIG. 16D). As shown in FIG. 16E, the original formulation O (306-O12B:cholesterol:DOPC:DMG-PEG at a molar ratio of 50:38.5:10:1.5) displayed the highest luciferase biolumінenscence intensity; none of the new formulation parameters could surpass the original In an effort to further increase the in vivo efficacy, the LNPs with this optimal ratio of four components were formulated with different weight ratios of active lipid 306-O12B:mRNA ranging from 5:1 to 25:1. Interestingly, it is found that the highest efficacy was achieved when the weight ratio was 7.5:1. It appears as though increasing the amount of lipid beyond this point did not benefit the in vivo delivery efficacy (FIG. 16F). Collectively, these results indicated that the optimized formulation of 306-O12B LNPs had 50% 306-O12B, 38.5% cholesterol, 10% DOPC, and 1.5% DMG-PEG molar composition with a 7.5/1 weight ratio of 306-O12B/mRNA.

Figure 17A:
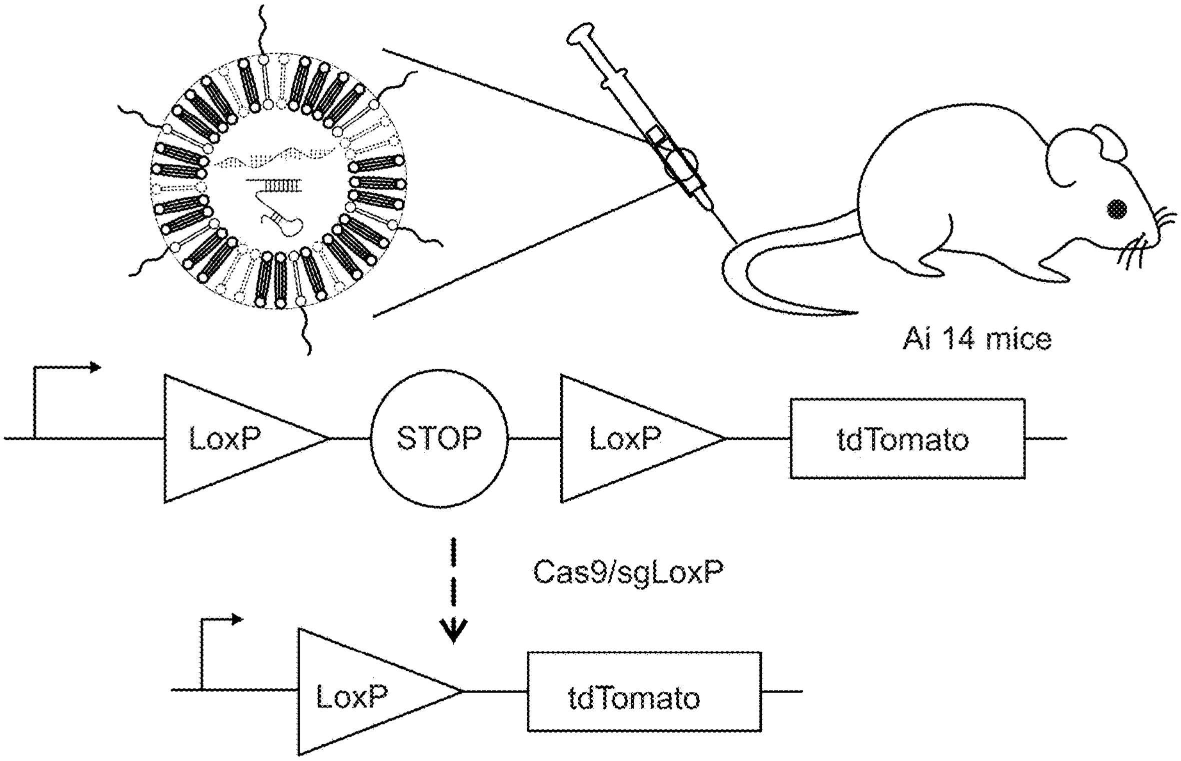
FIG. 17A is a schematic illustration of codelivery of Cas9 mRNA and LoxP-targeted single guide RNA (sgLoxP) to genetically engineered tdTomato reporter Ai14 mice using 306-O12B LNPs.
Figure 17B:
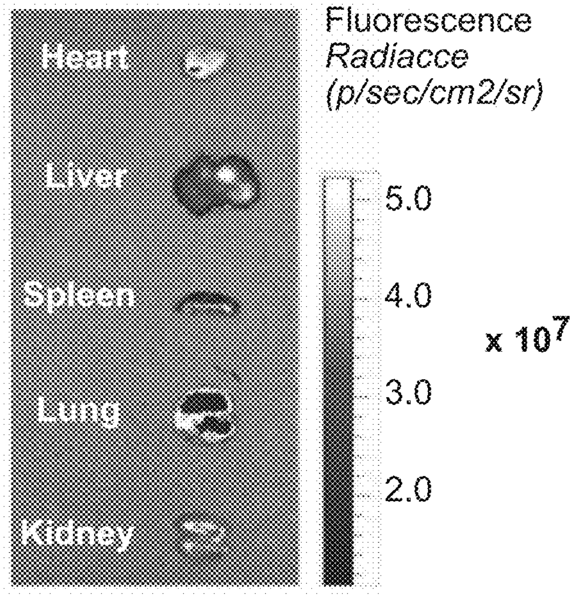
FIG. 17B is an Ex vivo image of organs collected from Ai14 mice administrated with LNPs encapsulating Cas9 mRNA/sgLoxP (1/1.2, wt) at a total RNA dose of 1.65 mg/kg, td Tomato fluorescence was detected by IVIS imaging system.
Figure 17C:
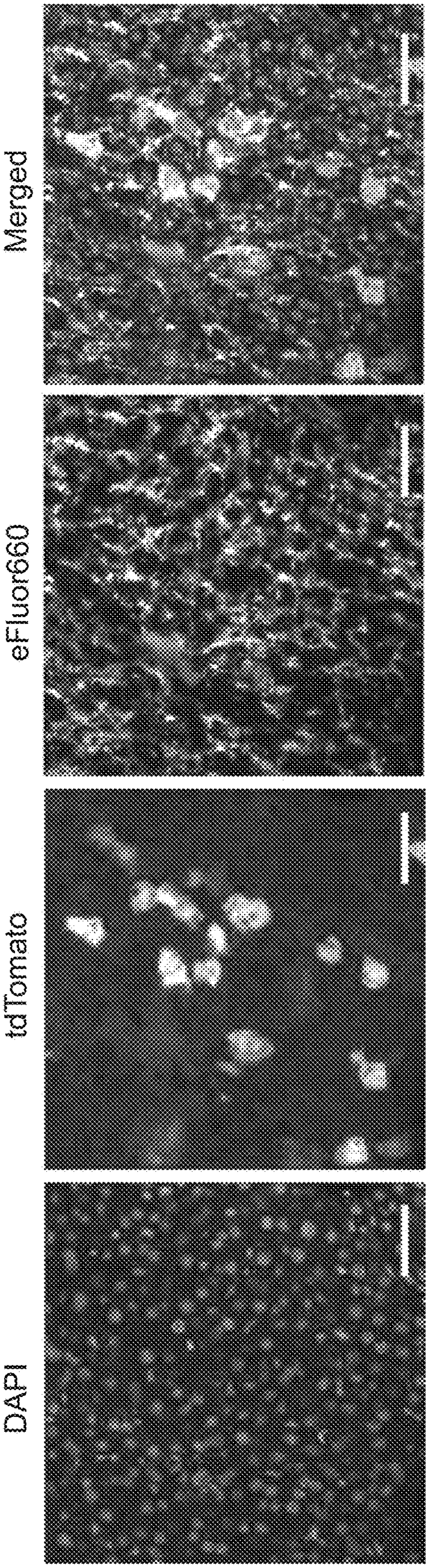
FIG. 17C are confocal fluorescence microscopy images of liver section showed that td Tomato signal was mainly expressed in liver hepatocytes. (Scale bar: 20 μm)

Example 6. In Vivo Hepatocytes Specific Codelivery of Cas9 mRNA and sgRNA with mRNA-Optimized LNPs FIGS. 17A-17C depict 306-O12B LNPs enabled Cas9/sgLoxP-mediated genome editing in Ai14 mice.

Figure 23A:
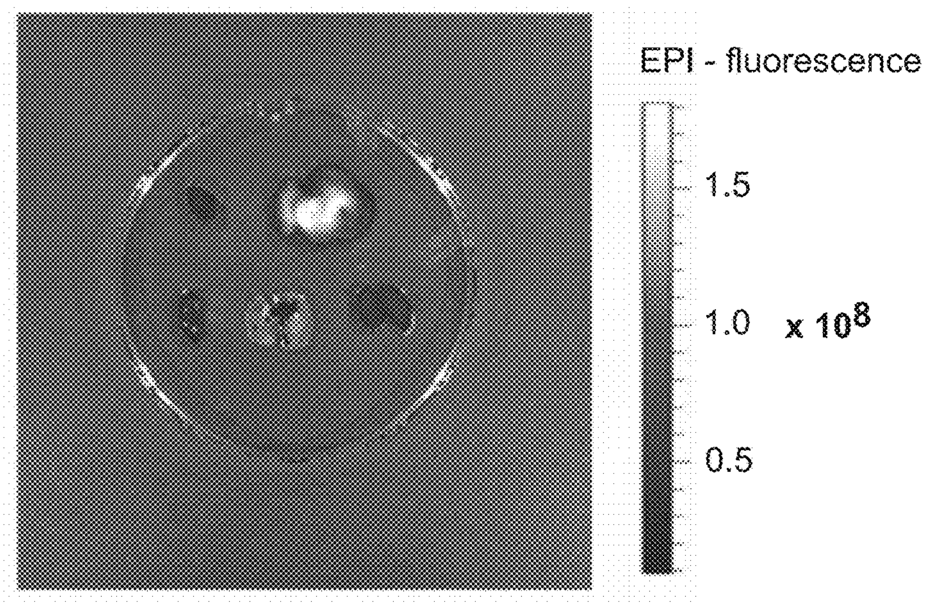
FIG. 23A is an ex vivo image of organs collected from Ai14/Cas9 mice administrated with 306-O12B LNPs encapsulating sgLoxP at a dose of 0.75 mg/kg, tdTomato fluorescence was detected by IVIS imaging system.
Figure 23B:
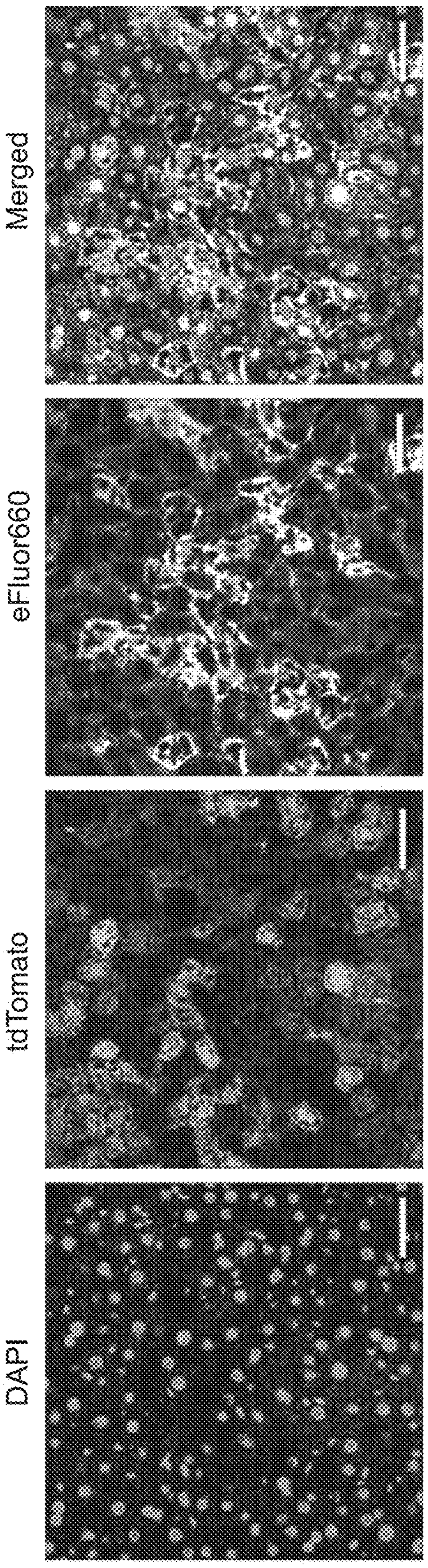
FIG. 23B are confocal fluorescence microscopy of liver section showed that td Tomato signal was mainly expressed in liver hepatocytes. (Scale bar: 20 μm)

FIG. 23A-23B are images that depicts 306-O12B LNPs enabled sgLoxP-mediated genome editing in Ai14/Cas9 crossing mice.

Identification of the specific cell types that are edited by Cas9 mRNA/sgRNA LNPs is of vital importance to predict the potential applications of a CRISPR delivery system. The Ai14 reporter mouse line, which is genetically engineered with a LoxP-Flanked STOP cassette controlling tdTomato expression, was used. While this mouse line is frequently used with Cre recombinase, successful CRISPR-mediated excision of the LoxP-flanked stop codon will also induce the expression of tdTomato. By examining the cells which have tdTomato expression, cell types our LNP delivery system could successfully target can be determined.

To validate this approach, we first used the 306-O12B LNPs to deliver the LoxP-targeted sgRNA (sgLoxP) to mice engineered to express both the Ai14 construct and a constitutively-expressed Cas9 construct (Ai14+/Cas9+ mouse model). As shown in FIG. 23A and FIG. 23B, delivery of sgLoxP with our LNP system resulted in red fluorescence detected specifically in the liver. Interestingly, further histological analysis revealed that the tdTomato signal was mainly observed in the liver hepatocytes, indicating that 306-O12B LNPs can also specifically deliver sgRNA to this therapeutically relevant cell type.

Next, Cas9 mRNA and sgLoxP were co-formulated into one single LNPs and injected into Ai14 mice via tail vein at 1.65 mg/kg total RNA dose (FIG. 17A). Seven days after delivery, organs were harvested and imaged ex vivo using the IVIS system. The ex vivo image of mouse organs analyzed by IVIS system showed that this system could indeed induce red fluorescence, indicating successful functional codelivery of both the mRNA and sgRNA components, and that tdTomato signal was predominantly detected in the liver (FIG. 17B). Immunofluorescent staining with a hepatocyte specific biomarker was further performed, and the confocal images demonstrated that the majority of the tdTomato protein was expressed in the hepatocytes (FIG. 17C). These findings strongly indicated that 306-O12B LNPs can specifically transport the CRISPR machinery to the liver hepatocytes.

Example 7. In Vivo Genome Editing of ANGPTL3

Figure 18A:
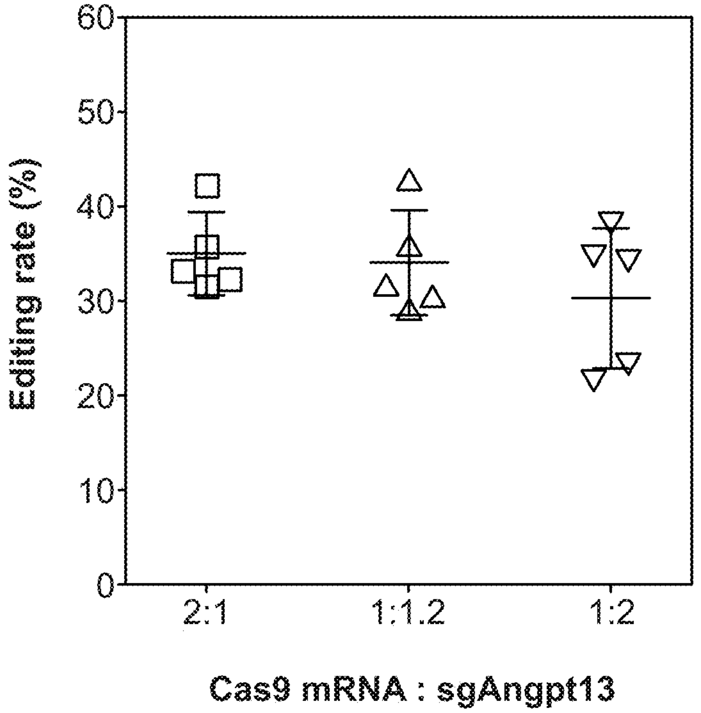
FIG. 18A is a graph depicting the Indels percentage following injections of 306-O12B LNPs formulated with Cas9 mRNA and sgAngptl3 at a mass ratio of 2:1, 1:1.2 and 1:2. (n=5).
Figure 18B:
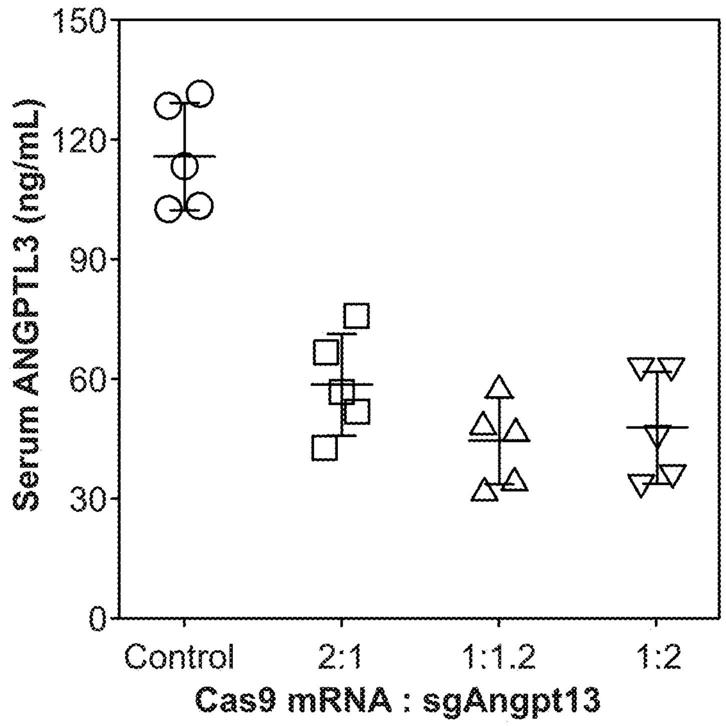
FIG. 18B is a graph depicting serum ANGPTL3 levels following injections of 306-O12B LNPs formulated with Cas9 mRNA and sgAngptl3 at a mass ratio of 2:1, 1:1.2 and 1:2. (n=5)

FIGS. 18A-18B depict 306-O12B LNPs-mediated significant levels of in vivo genome editing of ANGPTL3 in wild-type C57BL/6 mice.

Figure 19A:
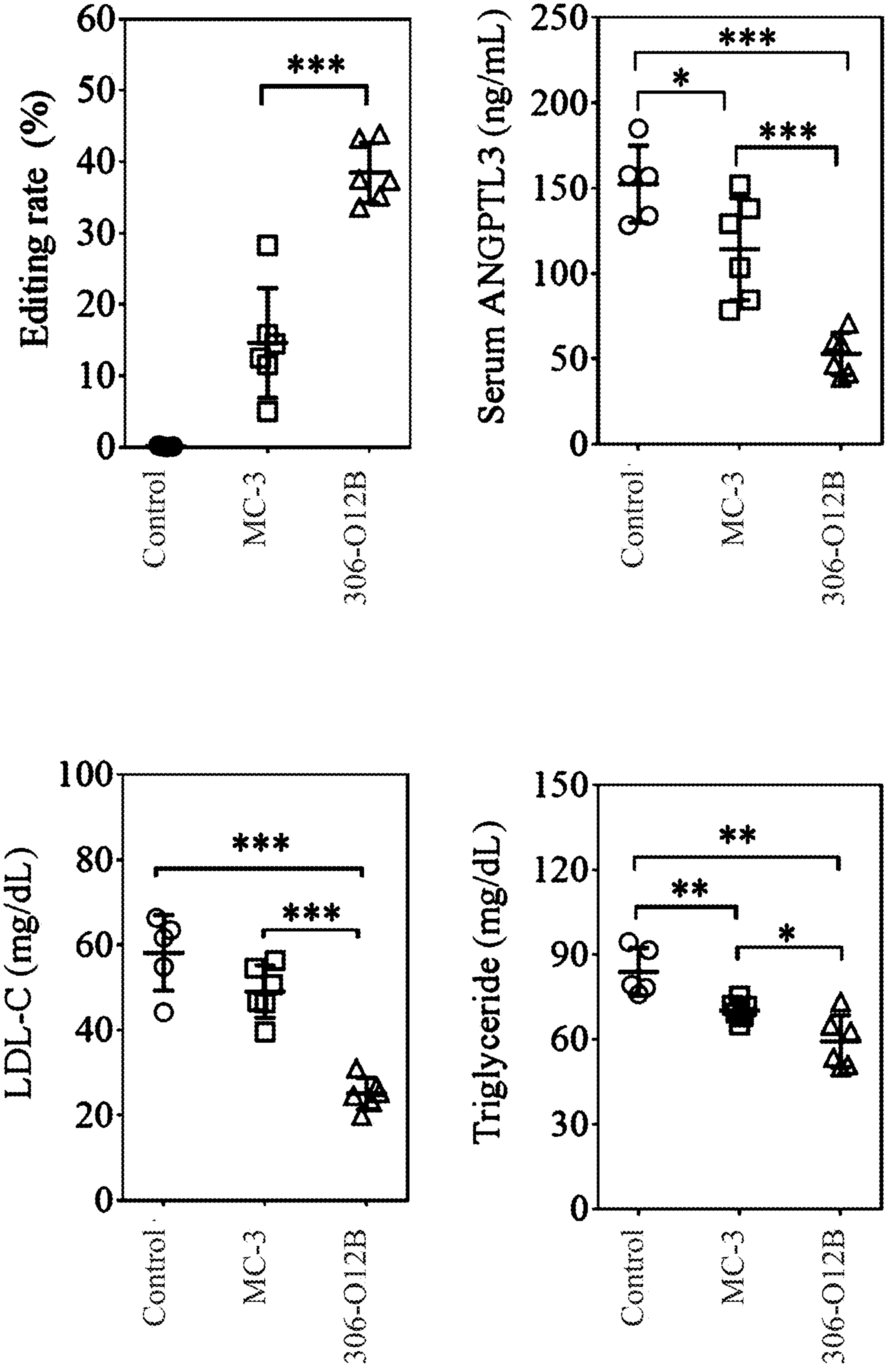
FIG. 19A are graphs depicting the next generation sequence analysis of the indels in liver and serum analyses of ANGPTL3 protein, triglyceride, and LDL-C level of mice at day 7 post administrated with Cas9 mRNA and sgAngptl2 coloaded 306-O12B LNPs at a total RNA dose of 3.0 mg/kg. MC-3 LNPs were used as a positive control. (n=5 or 6). *P<0.05, P<0.01, *P<0.001.

FIGS. 19A-19C show that 306-O12B LNPs is more efficient than MC-3 LNPs in inducing the loss-of-function mutations in ANGPTL3 through CRISPR/Cas9-based genome editing.

Figure 24:
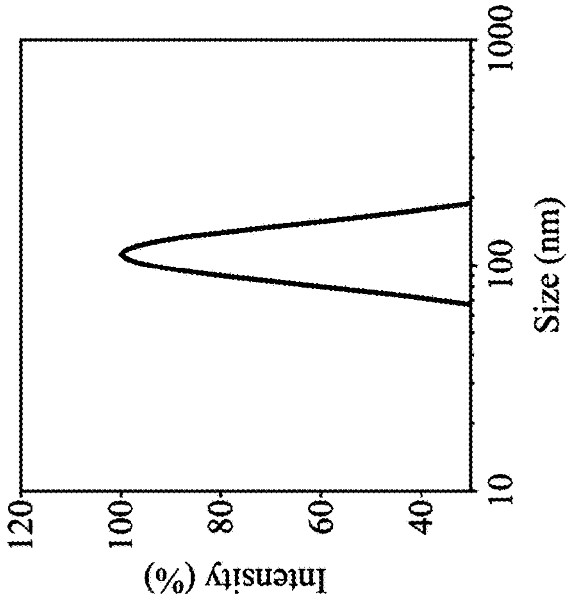
FIG. 24 is a dynamic light scattering graph depicting the size distribution of Cas9 mRNA/sgAngptl3 co-loaded 306-O12B LNPs.

Next, the capability of 306-O12B LNPs to deliver CRISPR/Cas9 mRNA to manipulate the expression of a functional endogenous gene is validated. The ANGPTL3 gene, encoding angiopoietin-like 3 (ANGPTL3), a central regulator of lipoprotein metabolism which inhibits both lipoprotein lipase and endothelial lipase activity, was selected as a target to study. Wild-type C57BL/6 mice were used to study the non-viral Cas9 mRNA/sgAngpt13 LNPs-mediated in vivo genome editing of ANGPTL3. Cas9 mRNA and sgAngpt13 were encapsulated into the 306-O12B LNPs simultaneously. Given that the CRISPR/Cas9 system contains two elements, Cas9 mRNA and sgRNA, the ratio of these two components may affect the in vivo genome editing efficacy. To this end, the mice is injected with 306-O12B LNPs co-formulated with different Cas9 mRNA to sgAngpt13 mass ratios of 2:1, 1:1.2, and 1:2 at a total RNA dose of 3.0 mg/kg. At day 7 after injection, blood serum was collected for ELISA analysis of serum ANGPTL3 protein levels, and liver tissue samples were collected for DNA extraction and NGS sequencing to determine targeted Cas9-mediated genome editing. It is observed genome editing in mice liver and the reduction of serum ANGPTL3 protein level at all Cas9 mRNA/sgAngpt13 ratios, however, no significant differences were observed between these groups (FIG. 18A and FIG. 18B). 1:1.2 Cas9 mRNA/sgAngpt13 ratio was used for the following experiments. The Cas9 mRNA/sgAngpt13 encapsulated 306-O12B LNPs had similar characteristics as fLuc mRNA LNPs with an average size of 110 nm (FIG. 24).

Figure 25:
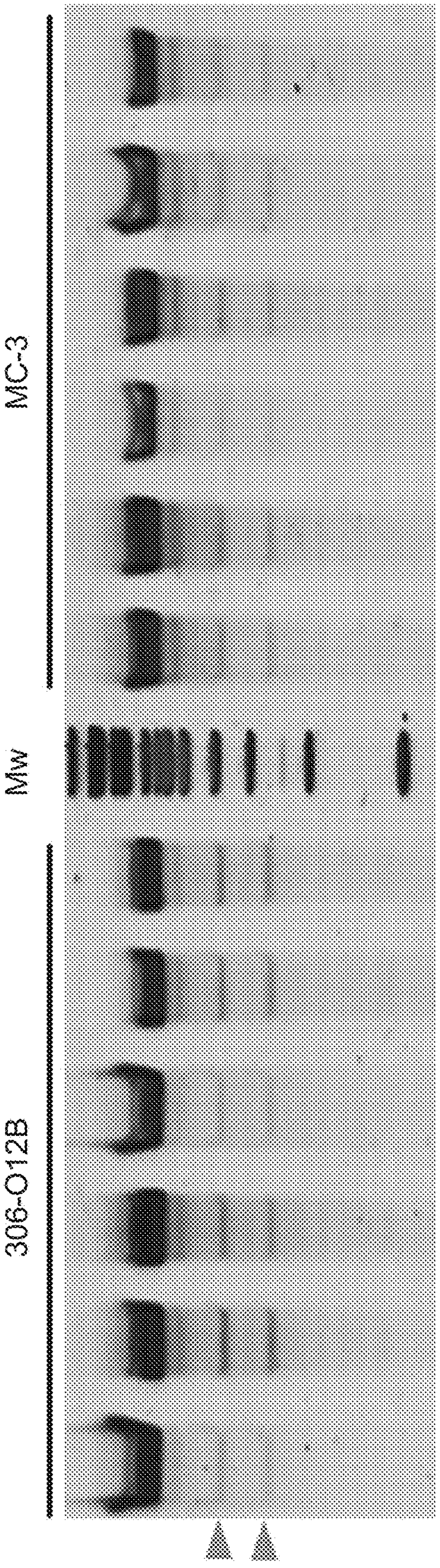
FIG. 25 is a gel electrophoresis image of T7E1 assays performed with genomic DNA from liver samples from mice taken 7 days after receiving the Cas9 mRNA/sgAngptl3 coloaded 306-O12B LNPs and MC-3 LNPs. Arrows show the cleavage products resulting from the T7E1 assays.

Given the significant levels of editing, a more detailed in vivo editing experiment was designed and performed. As a gold standard, we compared our 306-O12B LNPs, encapsulating the RNA components, against LNPs composed of the FDA-approved liver-delivery lipid MC-3, encapsulating the exact same RNA components (MC3-LNPs). It should be noted that the same ratios of excipient lipids were used in both the 306-O12B LNPs and the MC3-LNPs, and that this particular excipient formulation has been previously published for use with MC3-LNPs. Mice were administered with 306-O12B LNPs or MC-3-LNPs at a total RNA dose of 3.0 mg/kg. At day 7 after administration, the editing at the desired site in the liver using a T7E1 assay was observed (FIG. 25). Next generation sequencing (NGS) of the ANGPTL3 target site in liver samples further demonstrated that 306-O12B-LNPs-mediated delivery resulted in a median editing rate of 38.5%, which is significantly higher than that of MC-3-mediated delivery (14.6%) (FIG. 19A). More importantly, the serum analyses revealed that the serum ANGPTL3 protein, LDL-C, and TG levels in 306-O12B LNPs treatment group (65.2%, 56.8%, 29.4% reductions respectively) were significantly lower than that of MC-3 LNPs treated mice (25%, 15.7%, 16.3% reductions respectively) (FIG. 19A). A detailed analysis of the NGS sequencing results revealed that the most frequent editing event was a 1-nt deletion precisely at the predicted Cas9 cut site, followed by a 1-nt insertion at the same location (FIG. 19B). As expected, the same editing events were observed in both MC3 LNP and 306-O12B LNP-treated livers, the main difference was in the frequency of these events. This indicates that the observed serum component reductions were indeed a result of the Cas9-mediated genome editing, and implies that the difference in observed outcomes between the two lipids was solely a result of delivery efficiency, rather than some change in the innate activity of the Cas9 mRNA.

Figure 26:
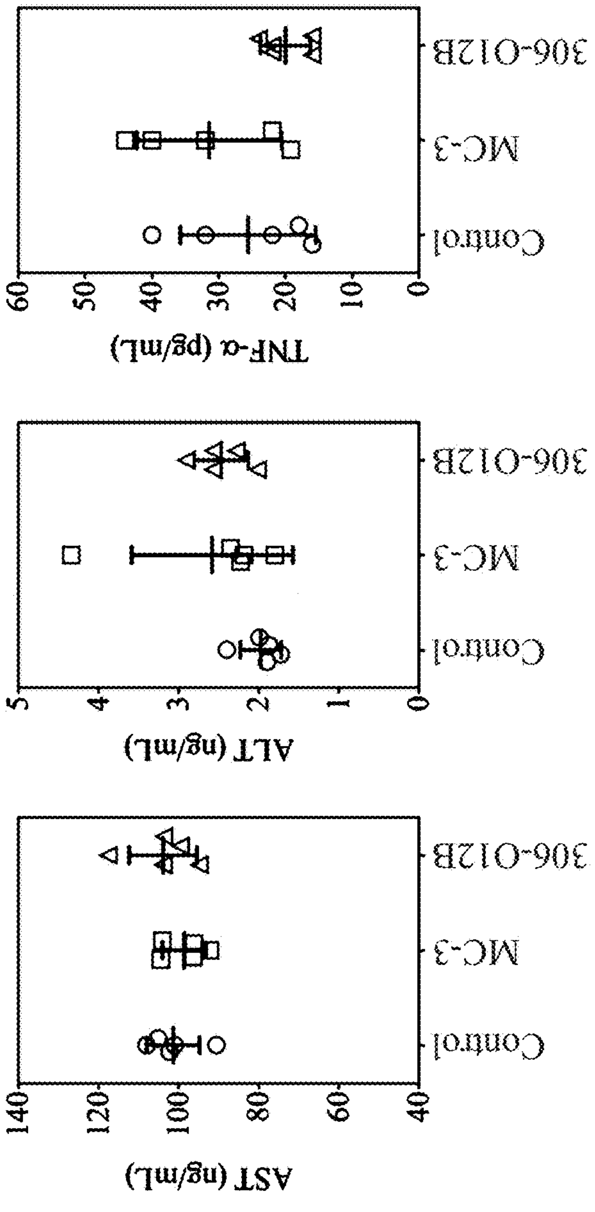
FIG. 26 are graphs that showing the serum levels of AST, ALT and TNF-alpha measured at day 2 post-injection. (n=5).

With any CRISPR delivery system, care must be taken to avoid off-target editing events or delivery-induced toxicity. The top 9 most likely off-target genomic mutagenesis sites were predicted computationally, and these loci were interrogated via NGS sequencing of DNA extracted from the liver. No evidence of editing at any of the 9-top predicted off-target mutagenesis sites was observed (FIG. 19C). To evaluate the in vivo toxicity and potential immunoinflammatory response, serum levels of the liver function markers aspartate aminotransferase (AST) and alanine aminotransferase (ALT), and of the proinflammatory cytokine tumor necrosis factor-alpha (TNF-alpha) were measured (FIG. 26). No significant changes in these parameters were detected after treatment with the CRISPR/Cas9 LNPs, further demonstrating negligible systemic toxicity.

REFERENCES CITED

1. P. D. Hsu, E. S. Lander, F. Zhang, *Cell* 2014, 157, 1262.
2. M. Jinek, K. Chylinski, I. Fonfara, M. Hauer, J. A. Doudna, E. Charpentier, *Science* 2012, 337, 816.
3. L. Cong, F. A. Ran, D. Cox, S. Lin, R. Barretto, N. Habib, P. D. Hsu, X. Wu, W. Jiang, L. A. Marraffini, F. Zhang, *Science* 2013, 339, 819.
4. G. J. Knott, J. A. Doudna, *Science* 2018, 361, 866.
5. H. X. Wang, M. Li, C. M. Lee, S. Chakraborty, H. W. Kim, G. Bao, K. W. Leong, *Chem. Rev.* 2017, 117, 9874.
6. H. Yin, K. J. Kauffman, D. G. Anderson, *Nat. Rev. Drug Discov.* 2017, 16, 387.

7. Z. Glass, M. Lee, Y. Li, Q. Xu, *Trends in Biotechnol.* 2018, 36, 173.
8. H. Yin, C. Q. Song, J. R. Dorkin, L. J. Zhu, Y. Li, Q. Wu, A. Park, J. Yang, S. Suresh, A. Bizhanova, A. Gupta, M. F. Bolukbasi, S. Walsh, R. L. Bogorad, G. Gao, Z. Weng, Y. Dong, V. Koteliansky, S. A. Wolfe, R. Langer, W. Xue, D. G. Anderson, *Nat. Biotechnol.* 2016, 34, 328.
9. M. Wang, J. A. Zuris, F. Meng, H. Rees, S. Sun, P. Deng, Y. Han, X. Gao, D. Pouli, Q. Wu, I. Georgakoudi, D. R. Liu, Q. Xu, *Proc. Natl. Acad. Sci. USA* 2016, 113, 2868.
10. L. Li, L. Song, X. Liu, X. Yang, X. Li, T. He, N. Wang, S. Yang, C. Yu, T. Yin, Y. Wen, Z. He, X. Wei, W. Su, Q. Wu, S. Yao, C. Gong, Y. Wei, *ACS Nano* 2017, 11, 95.
11. W. Sun, W. Ji, J. M. Hall, Q. Hu, C. Wang, C. L. Beisel, Z. Gu, *Angew. Chem., Int. Ed.* 2015, 54, 12029.
12. Q. Liu, K. Zhao, C. Wang, Z. Zhang, C. Zheng, Y. Zhao, Y. Zheng, C. Liu, Y. An, L. Shi, C. Kang, Y. Liu, *Adv. Sci.* 2019, 6, 1801423.
13. W. Zhou, H. Cui, L. Ying, X. F. Yu, Angew. Chem., *Int. Ed.* 2018, 57, 10268.
14. P. Wang, L. Zhang, W. Zheng, L. Cong, Z. Guo, Y. Xie, L. Wang, R. Tang, Q. Feng, Y. Hamada, K. Gonda, Z. Hu, X. Wu, X. Jiang, *Angew. Chem., Int. Ed.* 2018, 57, 1491.
15. K. Lee, M. Conboy, H. M. Park, F. Jiang, H. J. Kim, M. A. Dewitt, V. A. Mackley, K. Chang, A. Rao, C. Skinner, T. Shobha, M. Mehdipour, H. Liu, W. Huang, F. Lan, N. L. Bray, S. Li, J. E. Corn, K. Kataoka, J. A. Doudna, I. Conboy, N. Murthy, *Nat. Biomed. Eng.* 2017, 1, 889.
16. C. D. Sago, M. P. Lokugamage, K. Paunovska, D. A. Vanover, C. M. Monaco, N. N. Shah, M. G. Castro, S. E. Anderson, T. G. Rudoltz, G. N. Lando, P. M. Tiwari, J. L. Kirschman, N. Willett, Y. C. Jang, P. J. Santangelo, A. V. Bryksin, J. E. Dahlman, *Proc. Natl. Acad. Sci. USA* 2018, 115, E9944.
17. C. Xu, Z. Lu, Y. Luo, Y. Liu, Z. Cao, S. Shen, H. Li, J. Liu, K. Chen, Z. Chen, X. Yang, Z. Gu, J. Wang, *Nat. Commun.* 2018, 9, 1.
18. U. Sahin, K. Kariko, O. Tureci, *Nat. Rev. Drug Discov.* 2014, 13, 759.
19. X. Liang, J. Potter, S. Kumar, Y. Zou, R. Quintanilla, M. Sridharan, J. Carte, W. Chen, N. Roark, S. Ranganathan, N. Ravinder, J. D. Chesnut, *J. Biotechnol.* 2015, 208, 44.
20. C. J. McKinlay, J. R. Vargas, T. R. Blake, J. W. Hardy, M. Kanada, C. H. Contag, P. A. Wender, R. M. Waymouth, *Proc. Natl. Acad. Sci. USA* 2017, 114, E448.
21. C. J. McKinlay, N. L. Benner, 0. A. Haabeth, R. M. Waymouth, P. A. Wender, *Proc. Natl. Acad. Sci. USA* 2018, 115, E5859.
22. Y. Li, J. Bolinger, Y. Yu, Z. Glass, N. Shi, L. Yang, M. Wang, Q. Xu, Biomater. *Sci.* 2019, 7, 596.
22. X. Yang, Q. Tang, Y. Jiang, M. Zhang, M. Wang, L. Mao, *J. Am. Chem. Soc.* 2019, 141, 3782.
23. M. Wang, K. Alberti, S. Sun, C. L. Arellano, Q. Xu, *Angew. Chem., Int. Ed.* 2014, 53, 2893.
24. M. Wang, S. Sun, C. I. Neufeld, B. Perez-Ramirez, Q. Xu, *Angew. Chem., Int. Ed.* 2014, 53, 13444.
25. M. Wang, J. A. Zuris, F. Meng, H. Rees, S. Sun, P. Deng, Y. Han, X. Gao, D. Pouli, Q. Wu, I. Georgakoudi, D. R. Liu, Q. Xu, *Proc. Natl. Acad. Sci. USA* 2016, 113, 2868.
26. J. Chang, X. Chen, Z. Glass, F. Gao, L. Mao, M. Wang, Q. *Xu, Acc. Chem. Res.* 2019, 52, 665.
27. J. B. Miller, S. Zhang, P. Kos, H. Xiong, K. Zhou, S. S. Perelman, H. Zhu, D. J. Siegwart, *Angew. Chem., Int. Ed.* 2017, 56, 1059.
28. E. M. Kennedy, A. V. Kornepati, M. Goldstein, H. P. Bogerd, B. C. Poling, A. W. Whisnant, M. B. Kastan, B. R. Cullen, *J. Virol.* 2014, 88, 11965.
29. C. Jiang, M. Mei, B. Li, X. Zhu, W. Zu, Y. Tian, Q. Wang, Y. Guo, Y. Dong, X. Tan, *Cell Res.* 2017, 27, 440.
30. M. Abifadel, M. Varret, J. Rabes, D. Allard, K. Ouguerram, M. Devillers, C. Cruaud, S. Benjannet, L. Wickham, D. Erilich, A. Derre, L. Villeger, M. Farnier, I. Beucler, E. Bruckert, J. Chambaz, B. Chanu, J. M. Lecerf, G. Luc, P. Moulin, J. Weissenbach, A. Part, M. Krempf, C. Junien, N. G. Seidah, C. Boileau, *Nat. Genet.* 2003, 34, 154.
31. F. A. Ran, L. Cong, W. X. Yan, D. A. Scott, J. S. Gootenberg, A. J. Kriz, B. Zetsche, O. Shalem, X. W u, K. S. Makarova, E. V. Koonin, P. A. Sharp, F. Zhang, *Nature* 2015, 520, 186.
32. Raal, F. J. et al. Inclisiran for the Treatment of Heterozygous Familial Hypercholesterolemia. *N. Engl. J. Med.* 382, 1520-1530, (2020).
33. Ray, K. K. et al. Two Phase 3 Trials of Inclisiran in Patients with Elevated LDL Cholesterol. *N. Engl. J. Med.* 382, 1507-1519, (2020).
34. Koishi, R. et al. Angpt13 regulates lipid metabolism in mice. *Nature Genet.* 30, 151-157, (2002).
35. Romeo, S. et al. Rare loss-of-function mutations in ANGPTL family members contribute to plasma triglyceride levels in humans. *J. Clin. Invest.* 119, 70-79, (2009).
36. Tarugi, P., Bertolini, S. & Calandra, S. Angiopoietin-like protein 3 (ANGPTL3) deficiency and familial combined hypolipidemia. *J. Biomed. Res.* 33, 73-81, (2019).
37. Stitziel, N. O. et al. ANGPTL3 Deficiency and Protection Against Coronary Artery Disease. *J. Am. Coll. Cardiol.* 69, 2054-2063, (2017).
38. Musunuru, K. & Kathiresan, S. CARDIOVASCULAR ENDOCRINOLOGY Is ANGPTL3 the next PCSK9? *Nat. Rev. Endocrinol.* 13, 502-503, (2017).
39. Dewey, F. E. et al. Genetic and Pharmacologic Inactivation of ANGPTL3 and Cardiovascular Disease. *N. Engl. J. Med.* 377, 211-221, (2017).
40. Ahmad, Z. et al. Inhibition of Angiopoietin-Like Protein 3 With a Monoclonal Antibody Reduces Triglycerides in Hypertriglyceridemia. *Circulation* 140, 470-486, (2019).
41. Graham, M. J. et al. Cardiovascular and Metabolic Effects of ANGPTL3 Antisense Oligonucleotides. *N. Engl. J. Med.* 377, 222-232, (2017).
42. Hsu, P. D., Lander, E. S. & Zhang, F. Development and Applications of CRISPR-Cas9 for Genome Engineering. *Cell* 157, 1262-1278, (2014).
43. Doudna, J. A. & Charpentier, E. The new frontier of genome engineering with CRISPR-Cas9. *Science* 346, 1077-+, (2014).
44. Chen, X. & Goncalves, M. Engineered Viruses as Genome Editing Devices. *Mol. Ther.* 24, 447-457, (2016).
45. Yin, H., Kauffman, K. J. & Anderson, D. G. Delivery technologies for genome editing. *Nat. Rev. Drug Discov.* 16, 387-399, (2017).
46. Glass, Z., Lee, M., Li, Y. M. & Xu, Q. B. Engineering the Delivery System for CRISPR-Based Genome Editing. *Trends Biotechnol.* 36, 173-185, (2018).
47. Yin, H. et al. Non-viral vectors for gene-based therapy. *Nat. Rev. Genet.* 15, 541-555, (2014).
48. Wang, M., Glass, Z. A. & Xu, Q. Non-viral delivery of genome-editing nucleases for gene therapy. *Gene Ther.* 24, 144-150, (2017).
49. Qiu, M., Glass, Z. & Xu, Q. B. Nonviral Nanoparticles for CRISPR-Based Genome Editing: Is It Just a Simple Adaption of What Have Been Developed for Nucleic Acid Delivery? *Biomacromolecules* 20, 3333-3339, (2019).
50. Wang, M. et al. Efficient delivery of genome-editing proteins using bioreducible lipid nanoparticles. *Proc. Natl. Acad. Sci. U.S.A* 113, 2868-2873, (2016).

51. Finn, J. D. et al. A Single Administration of CRISPR/Cas9 Lipid Nanoparticles Achieves Robust and Persistent In Vivo Genome Editing. *Cell Reports* 22, 2227-2235, (2018).
52. Miller, J. B. et al. Non-Viral CRISPR/Cas Gene Editing In Vitro and In Vivo Enabled by Synthetic Nanoparticle Co-Delivery of Cas9 mRNA and sgRNA. *Angew. Chem.-Int. Edit.* 56, 1059-1063, (2017).
53. Jiang, C. et al. A non-viral CRISPR/Cas9 delivery system for therapeutically targeting HBV DNA and pcsk9 in vivo. *Cell Res.* 27, 440-443, (2017).
54. Liu, J. et al. Fast and Efficient CRISPR/Cas9 Genome Editing In Vivo Enabled by Bioreducible Lipid and Messenger RNA Nanoparticles. *Adv. Mater.* 31, 7, (2019).
55. Chadwick, A. C., Evitt, N. H., Lv, W. J. & Musunuru, K. Reduced Blood Lipid Levels With In Vivo CRISPR-Cas9 Base Editing of ANGPTL3. *Circulation* 137, 975-977, (2018).
56. Akinc, A. et al. The Onpattro story and the clinical translation of nanomedicines containing nucleic acid-based drugs. *Nat. Nanotechnol.* 14, 1084-1087, (2019).
57. Wang, M. et al. Enhanced Intracellular siRNA Delivery using Bioreducible Lipid-Like Nanoparticles. *Adv. Healthc. Mater.* 3, 1398-1403, (2014).
58. Zhi, D. F. et al. Transfection Efficiency of Cationic Lipids with Different Hydrophobic Domains in Gene Delivery. *Bioconjugate Chem.* 21, 563-577, (2010).
59. Wang, M., Sun, S., Alberti, K. A. & Xu, Q. B. A Combinatorial Library of Unsaturated Lipidoids for Efficient Intracellular Gene Delivery. *ACS Synth. Biol.* 1, 403-407, (2012).
60. Kauffman, K. J. et al. Optimization of Lipid Nanoparticle Formulations for mRNA Delivery in Vivo with Fractional Factorial and Definitive Screening Designs. *Nano Lett.* 15, 7300-7306, (2015).
61. Sedic, M. et al. Safety Evaluation of Lipid Nanoparticle-Formulated Modified mRNA in the Sprague-Dawley Rat and Cynomolgus Monkey. *Vet. Pathol.* 55, 341-354, (2018).
62. Madisen, L. et al. A robust and high-throughput Cre reporting and characterization system for the whole mouse brain. *Nat. Neurosci.* 13, 133-U311, (2010).
63. Tabebordbar, M. et al. In vivo gene editing in dystrophic mouse muscle and muscle stem cells. *Science* 351, 407-411, (2016).
64. Platt, R. J. et al. CRISPR-Cas9 Knockin Mice for Genome Editing and Cancer Modeling. *Cell* 159, 440-455, (2014).
65. Mout, R., Ray, M., Lee, Y. W., Scaletti, F. & Rotello, V. M. In Vivo Delivery of CRISPR/Cas9 for Therapeutic Gene Editing: Progress and Challenges. *Bioconjugate Chem.* 28, 880-884, (2017).
66. Tong, S., Moyo, B., Lee, C. M., Leong, K. & Bao, G. Engineered materials for in vivo delivery of genome-editing machinery. *Nat. Rev. Mater.* 4, 726-737, (2019).
67. Komor, A. C., Badran, A. H. & Liu, D. R. CRISPR-Based Technologies for the Manipulation of Eukaryotic Genomes. *Cell* 168, 20-36, (2017).
68. Liang, X. Q. et al. Rapid and highly efficient mammalian cell engineering via Cas9 protein transfection. *J. Biotechnol.* 208, 44-53, (2015).
69. Ramaswamy, S. et al. Systemic delivery of factor IX messenger RNA for protein replacement therapy. *Proc. Natl. Acad. Sci. U.S.A* 114, E1941-E1950, (2017).
70. Sabnis, S. et al. A Novel Amino Lipid Series for mRNA Delivery: Improved Endosomal Escape and Sustained Pharmacology and Safety in Non-human Primates. *Mol. Ther.* 26, 1509-1519, (2018).
71. Hou, X. C. et al. Vitamin lipid nanoparticles enable adoptive macrophage transfer for the treatment of multidrug-resistant bacterial sepsis. *Nat. Nanotechnol.* 15, 41−+, (2020).
72. Fenton, O. S. et al. Bioinspired Alkenyl Amino Alcohol Ionizable Lipid Materials for Highly Potent In Vivo mRNA Delivery. *Adv. Mater.* 28, 2939-2943, (2016).
73. Bae, S., Park, J. & Kim, J. S. Cas-OFFinder: a fast and versatile algorithm that searches for potential off-target sites of Cas9 RNA-guided endonucleases. *Bioinformatics* 30, 1473-1475, (2014).
74. Schmid-Burgk, J. L. et al. Out Knocker: a web tool for rapid and simple genotyping of designer nuclease edited cell lines. *Genome Res.* 24, 1719-1723, (2014).

We claim:

1. A method of treating a human lipoprotein metabolism disorder or a cardiovascular disease, comprising administering to a subject in need thereof a lipidoid nanoparticle comprising a lipid, a CRISPR/Cas9 mRNA, and a single guide RNA (sgRNA);

wherein the sgRNA is single guide Angiopoietin-like 3 (sgANGPTL3) or single guide proprotein convertase subtilisin/kexin type 9 (sgPCSK9);

the human lipoprotein metabolism disorder is associated with loss-of-function mutations in ANGPTL3 gene;

the cardiovascular disease is associated with proprotein convertase subtilisin/kexin type 9 gene (PCSK9); and the lipid is represented by formula I:

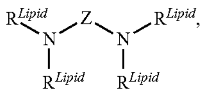

(I)

or a pharmaceutically acceptable salt thereof, wherein Z is

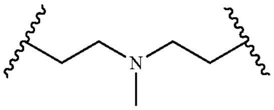

or

-continued

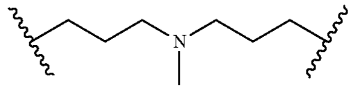

and each $R^{Lipid}$ is independently:

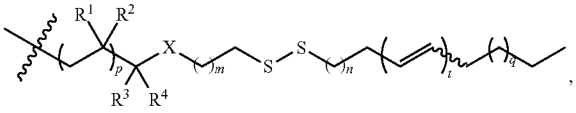

, wherein:

each $R^1$ is H or OH;

each $R^2$ is H;

$R^3$ and $R^4$ are taken together to form an oxo (═O) group;

X is $CH_2$ O, or NH;

m is an integer selected from 1-3;

n is an integer selected from 1-14;

p is 0 or 1;

q is an integer selected from 1-10; and t is 0, 1, or 2.

2. The method of claim 1, wherein X is O.

3. The method of claim 1, wherein $R^{Lipid}$ each independently is selected from the group consisting of

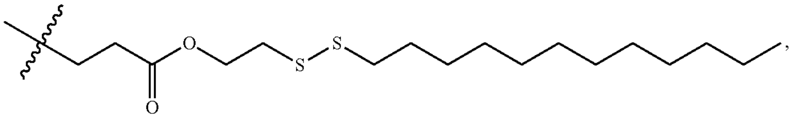

,

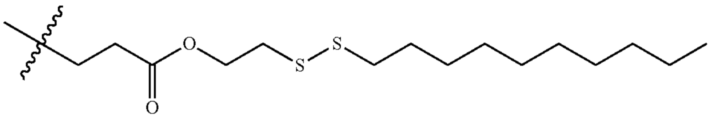

,

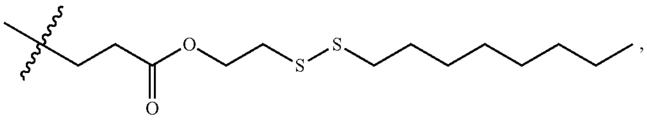

,

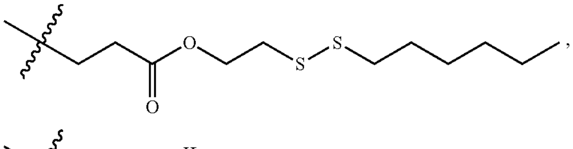

,

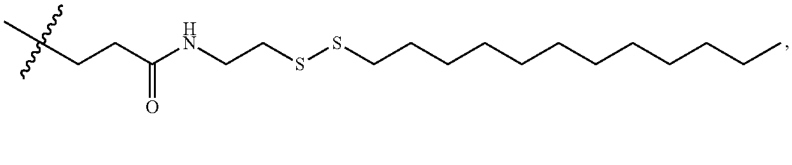

,

-continued
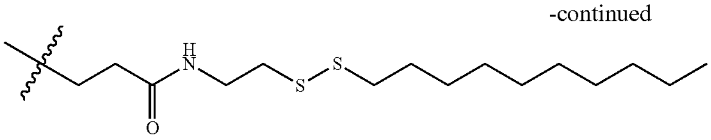,
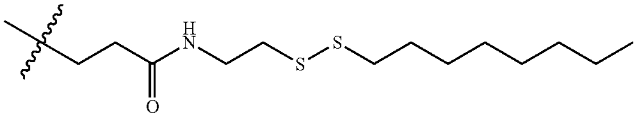,
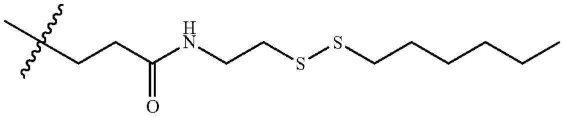,
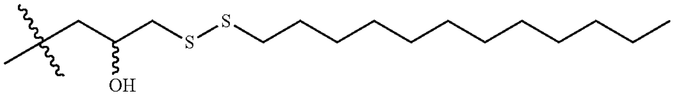,
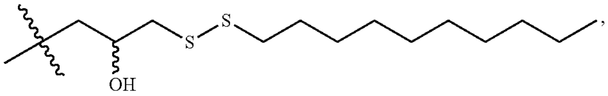, 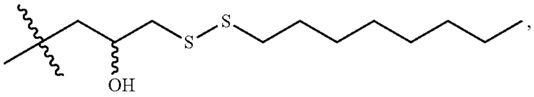, and
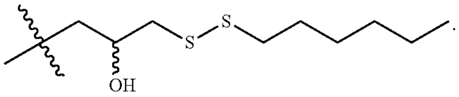.
4. The method of claim 1, wherein the lipid is selected from the group consisting of
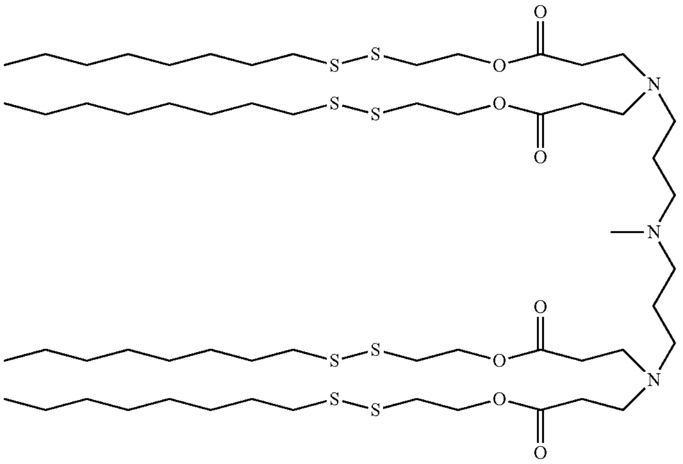 and
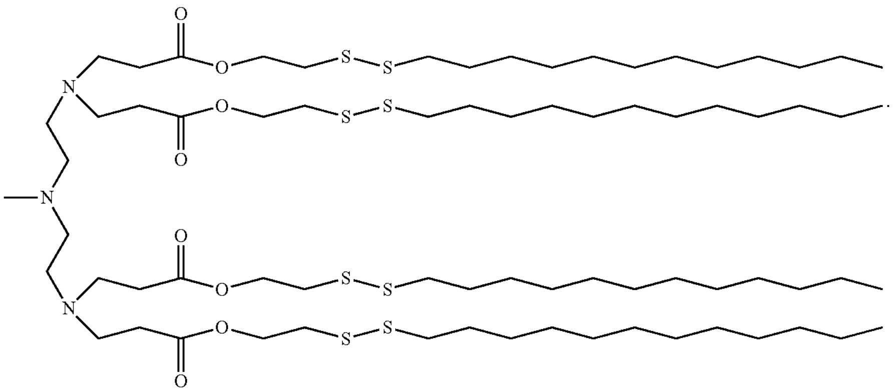.

5. The method of claim 1, wherein the weight ratio of the lipid to the CRISPR/Cas9 mRNA is about 3:1 to about 15:1.

6. The method of claim 5, wherein the weight ratio of the lipid to the CRISPR/Cas9 mRNA is about 7.5:1.

7. The method of claim 1, wherein the lipidoid nanoparticle further comprises cholesterol.

8. The method of claim 7, wherein the molar ratio of the lipid to the cholesterol is about 1:1 to about 2:1.

9. The method of claim 1, wherein the lipidoid nanoparticle further comprises DOPE, DSPC, or DOPC; and DMG-PEG2K; wherein DSPC has the structure:

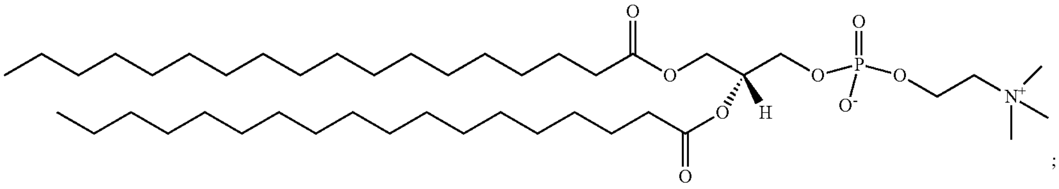 [SMILES: CCCCCCCCCCCCCCCCCC(=O)OC[C@H](COP(=O)([O-])OCC[N+](C)(C)C)OC(=O)CCCCCCCCCCCCCCCCC]

;

DOPE has the structure:

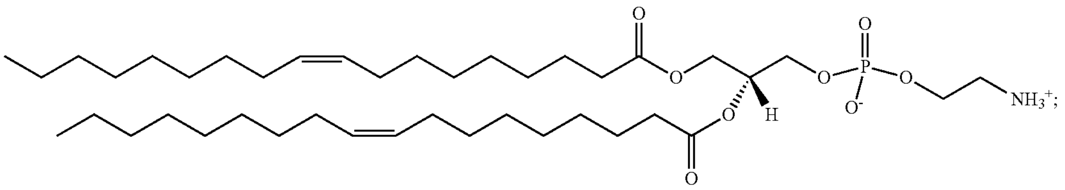

DOPC has the structure:

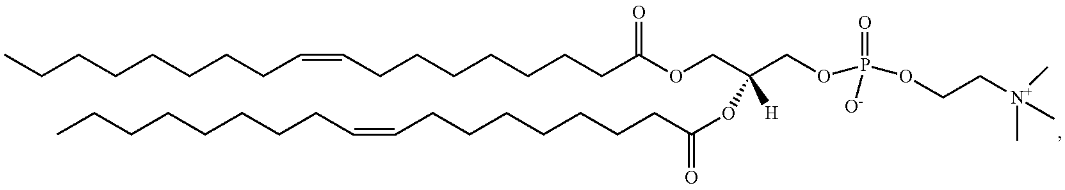 [SMILES: CCCCCCCC/C=C\CCCCCCCC(=O)OC[C@H](COP(=O)([O-])OCC[N+](C)(C)C)OC(=O)CCCCCCC/C=C\CCCCCCCC]

, and

DMG-PEG2K has the structure:

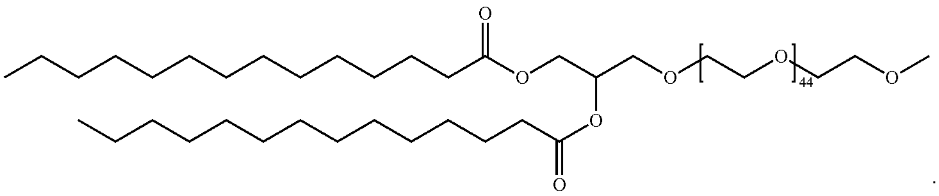

.

10. The method of claim 9, wherein the lipidoid nanoparticle comprises DOPC and DMG-PEG2K.

11. The method of claim 10, wherein the molar ratio of the lipid to the DOPC is about 4:1 to about 6:1; and the molar ratio of the lipid to the DMG-PEG2K is about 4:1 to about 100:1.

12. The method of claim 1, wherein the lipidoid nanoparticle has a particle size of about 25 nm to about 1000 nm.

13. The method of claim 1, wherein the method is for treating a human lipoprotein metabolism disorder and the human lipoprotein metabolism disorder is associated with loss-of-function mutations in ANGPTL3 gene.

14. The method of claim 1, wherein the method is for treating a cardiovascular disease and the cardiovascular disease is associated with proprotein convertase subtilisin/kexin type 9 gene (PCSK9).

15. The method of claim 13, wherein the human lipoprotein metabolism disorder is associated with low levels of plasma high density lipoprotein cholesterol, high levels of serum low density lipoprotein cholesterol, or high levels of triglycerides.

16. The method of claim 15, wherein the cardiovascular disease is selected from the group consisting of homozygous familial hypercholesterolemia, and hypercholesterolemia.

17. The method of claim 1, wherein the lipid is

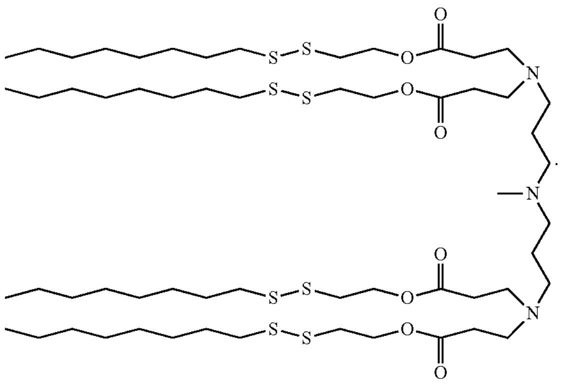 [SMILES: CCCCCCCCSSCCOC(=O)CCN(CCCN(C)CCCN(CCC(=O)OCCSSCCCCCCCC)CCC(=O)OCCSSCCCCCCCC)CCC(=O)OCCSSCCCCCCCC]

18. The method of claim 1, wherein the lipid is

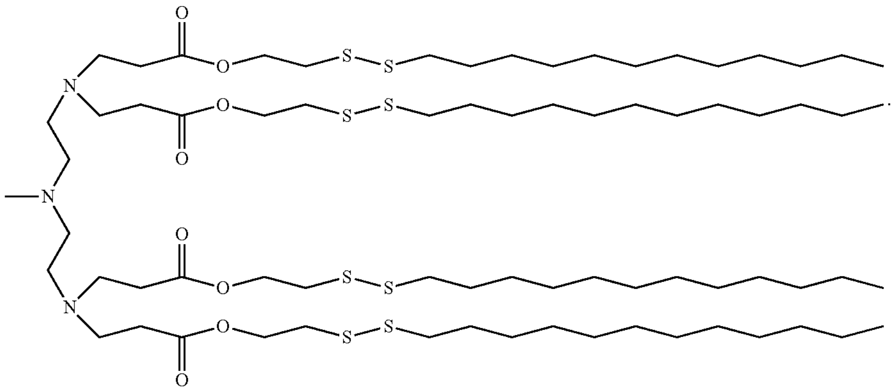 [SMILES: CCCCCCCCCCCCSSCCOC(=O)CCN(CCC(=O)OCCSSCCCCCCCCCCCC)CCN(C)CCN(CCC(=O)OCCSSCCCCCCCCCCCC)CCC(=O)OCCSSCCCCCCCCCCCC]

19. The method of claim 1, wherein Z is

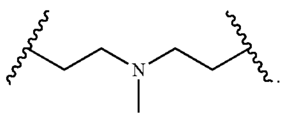 [SMILES: *CCN(C)CC*]

20. The method of claim 1, wherein Z is

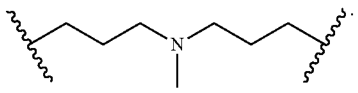 [SMILES: *CCCN(C)CCC*]

* * * * *

SEQUENCE LISTING

```
<160> NUMBER OF SEQ ID NOS: 41

<210> SEQ ID NO 1
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 1

gggcacgggc agcuugccgg                                                  20


<210> SEQ ID NO 2
<211> LENGTH: 21
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 2

gauaaauaac gcgcccaaca c                                                21
```

<210> SEQ ID NO 3
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 3
gggcgcuuug aggauccaac a 21

<210> SEQ ID NO 4
<211> LENGTH: 21
<212> TYPE: RNA
<213> ORGANISM: Artificial Sequence
<220> FEATURE:
<223> OTHER INFORMATION: Description of Artificial Sequence: Synthetic oligonucleotide

<400> SEQUENCE: 4
cccaugugga guacauuggu u 21

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 5
aagtaaaacc tctacaaatg 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 6
agcccttcaa cacaaggtca 20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 7
ctccaaagcc ctgaccttgt 20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 8
ttctgcacct tcagagccaa 20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 9
accttggtta ggatgcctgc 20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 10
acatagccat cccccaacaa 20

<210> SEQ ID NO 11
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 11
tgacatgact cattgccacc a 21

<210> SEQ ID NO 12
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 12
tctaaatgcc agggttctga ct 22

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 13
tacccagcca tattgtgcag 20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 14
cggatgtttg catgagggga 20

-continued

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 15
ggtgtccact tgttaaatgt ca 22

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 16
gccagccaca gttttcatcg 20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 17
gcagtcatca gacaggaggg 20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 18
tctgcacctt cagagccaaa 20

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
gcaaagcaaa ccctgaactg a 21

<210> SEQ ID NO 20
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 20
ttgcattcct gtcagagtga t 21

<210> SEQ ID NO 21

<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 21
gctgcaactt ggtgctacct 20

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 22
gtgaaccata tcttaatagc accat 25

<210> SEQ ID NO 23
<211> LENGTH: 22
<212> TYPE: DNA
<213> ORGANISM: Artificial Sequence
<220> FEATURE:
<223> OTHER INFORMATION: Description of Artificial Sequence: Synthetic primer

<400> SEQUENCE: 23
catgccatgt ggggtgatac aa 22

<210> SEQ ID NO 24
<211> LENGTH: 25
<212> TYPE: DNA
<213> ORGANISM: Artificial Sequence
<220> FEATURE:
<223> OTHER INFORMATION: Description of Artificial Sequence: Synthetic primer

<400> SEQUENCE: 24
agaagaccag atagaagtca ggatg 25

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 25
ggttagctgc tggacactga 20

<210> SEQ ID NO 26
<211> LENGTH: 21
<212> TYPE: DNA
<213> ORGANISM: Artificial Sequence
<220> FEATURE:
<223> OTHER INFORMATION: Description of Artificial Sequence: Synthetic primer

<400> SEQUENCE: 26
acaacaacat ggaaaactct a 21

<210> SEQ ID NO 27
<211> LENGTH: 20

<212> TYPE: DNA
<213> ORGANISM: Artificial Sequence
<220> FEATURE:
<223> OTHER INFORMATION: Description of Artificial Sequence: Synthetic
primer

<400> SEQUENCE: 27
gggagtcaca gtcatgggtc 20

<210> SEQ ID NO 28
<211> LENGTH: 20
<212> TYPE: DNA
<213> ORGANISM: Artificial Sequence
<220> FEATURE:
<223> OTHER INFORMATION: Description of Artificial Sequence: Synthetic
primer

<400> SEQUENCE: 28
gcagctctcc aatccagaca 20

<210> SEQ ID NO 29
<211> LENGTH: 20
<212> TYPE: DNA
<213> ORGANISM: Mus sp.

<400> SEQUENCE: 29
cgtttttaac ttgtagtgta 20

<210> SEQ ID NO 30
<211> LENGTH: 19
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 30
cgttttaact tgtagtgta 19

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 31
cgttttttaa cttgtagtgt a 21

<210> SEQ ID NO 32
<211> LENGTH: 18
<212> TYPE: DNA
<213> ORGANISM: Artificial Sequence
<220> FEATURE:
<223> OTHER INFORMATION: Description of Artificial Sequence: Synthetic
oligonucleotide

<400> SEQUENCE: 32
cgtttaactt gtagtgta 18

<210> SEQ ID NO 33
<211> LENGTH: 22
<212> TYPE: DNA
<213> ORGANISM: Mus sp.

<400> SEQUENCE: 33
aacactacaa ttaaaaacgt gg 22

<210> SEQ ID NO 34
<211> LENGTH: 22
<212> TYPE: DNA
<213> ORGANISM: Mus sp.

<400> SEQUENCE: 34
tacactaaaa ttaaaaacgt gg 22

<210> SEQ ID NO 35
<211> LENGTH: 24
<212> TYPE: DNA
<213> ORGANISM: Mus sp.

<400> SEQUENCE: 35
ttcactacaa gttagaaaac aggg 24

<210> SEQ ID NO 36
<211> LENGTH: 24
<212> TYPE: DNA
<213> ORGANISM: Mus sp.

<400> SEQUENCE: 36
tacactacga aattaaaacc gagg 24

<210> SEQ ID NO 37
<211> LENGTH: 24
<212> TYPE: DNA
<213> ORGANISM: Mus sp.

<400> SEQUENCE: 37
tacactacaa gttcaaatac atgg 24

<210> SEQ ID NO 38
<211> LENGTH: 22
<212> TYPE: DNA
<213> ORGANISM: Mus sp.

<400> SEQUENCE: 38
tacactaaag ataaaaacat gg 22

<210> SEQ ID NO 39
<211> LENGTH: 22
<212> TYPE: DNA
<213> ORGANISM: Mus sp.

<400> SEQUENCE: 39
tacagtcaag ttaaaaacca gg 22

<210> SEQ ID NO 40
<211> LENGTH: 22
<212> TYPE: DNA
<213> ORGANISM: Mus sp.

<400> SEQUENCE: 40
tcactactag ataaaaacgt gg 22

<210> SEQ ID NO 41
<211> LENGTH: 22
<212> TYPE: DNA
<213> ORGANISM: Mus sp.

-continued

```
<400> SEQUENCE: 41

cacactacaa gtaaaaacag gg                                    22
```